Figure 1:
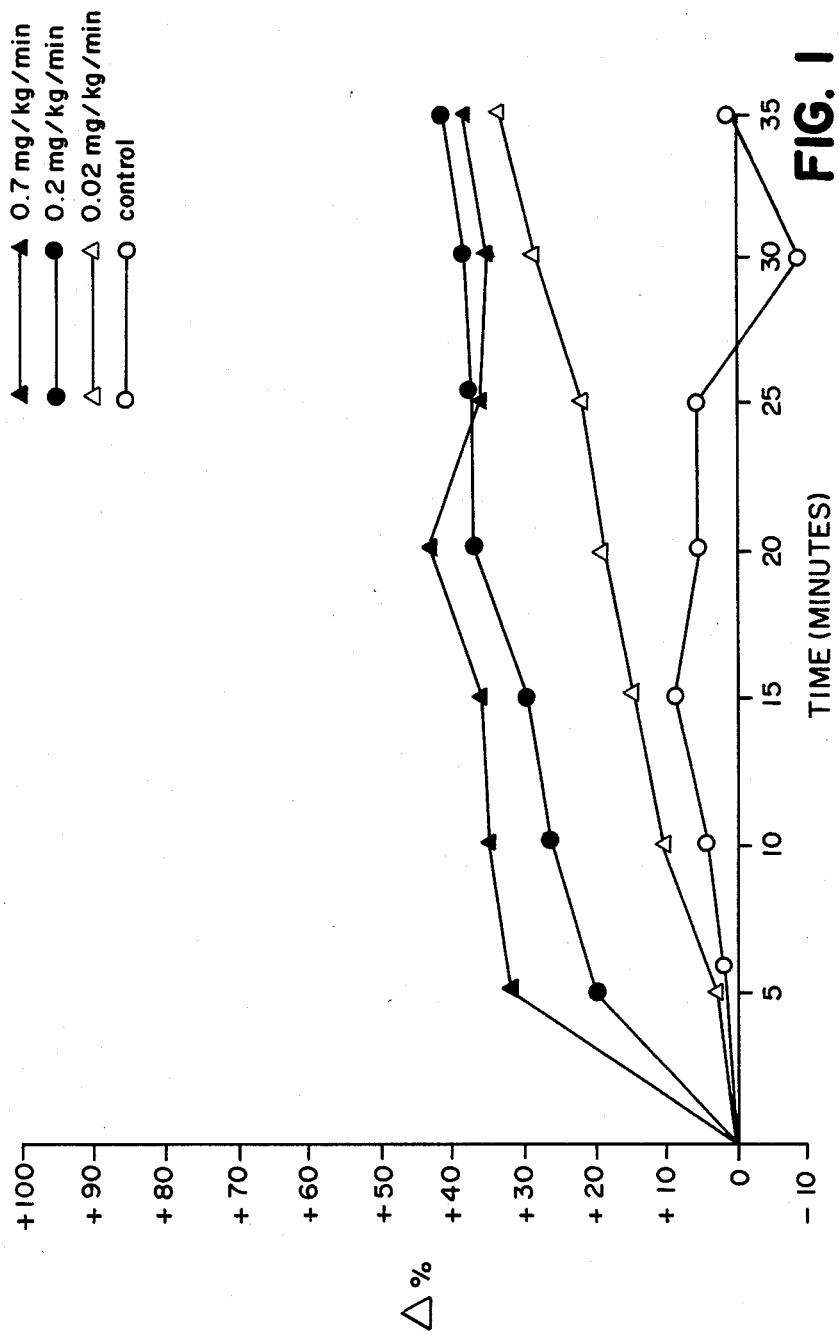

United States Patent [19]

Maroko

[11] Patent Number: 4,761,417

[45] Date of Patent: Aug. 2, 1988

[54] COMPOUNDS, COMPOSITIONS AND METHOD OF TREATMENTS FOR IMPROVING CIRCULATORY PERFORMANCE

[76] Inventor: Peter R. Maroko, 1765 Garwood Dr., Cherry Hill, N.J. 08003

[21] Appl. No.: 788,507

[22] Filed: Oct. 18, 1985

Related U.S. Application Data

[63] Continuation of Ser. No. 378,122, May 14, 1982, abandoned.

[51] Int. Cl.$^4$ .................... A61K 31/44; A61K 31/705
[52] U.S. Cl. ........................ 514/284; 514/280
[58] Field of Search .................... 514/280, 284, 26

[56] References Cited

U.S. PATENT DOCUMENTS

| | | | |
|---|---|---|---|
| 3,326,920 | 6/1967 | Stanaback et al. | 546/71 |
| 3,346,582 | 10/1967 | Brown et al. | 546/71 |
| 3,933,826 | 1/1976 | Kametani | 424/258 |
| 4,013,666 | 3/1977 | Lenz | 546/71 |

FOREIGN PATENT DOCUMENTS

| | | | |
|---|---|---|---|
| 37976 | 4/1967 | Japan | 546/71 |
| 105699 | 7/1972 | Japan | 546/71 |
| 1187733 | 4/1970 | United Kingdom | 546/71 |

OTHER PUBLICATIONS

Soto et al—Rev. Assoc. Med Argent, 41:3062–3068 (1933).
Soto et al—Rev. Assoc. Med Argent 47: 2494–2501, (1933).
Chopra—Ind. Jour. Med. Res., XIX, 4, Apr. 1932, pp. 1193–1203.
Williams—Jour. A.M.A., Jan. 4, 1908.
Kulkarni et al—*Japan J. Pharmacol.* 22, 11–16 (1972).
*Chemical & Pharmaceutical Bulletin*, vol. 18, No. 7, Jul. 1970, pp. 1299–1304—Fukuda et al.
*J. Pharmacol. Exp. Ther.*, 71: 178–186 (1941), Jang.
Mercier et al—Comptes Rendus Societe de Biologie, 127: 1022–1024, (1938).

*Primary Examiner*—Frederick E. Waddell
*Attorney, Agent, or Firm*—Weiser & Stapler

[57] ABSTRACT

A method of increasing the contractility of the mammalian heart as shown by a positive inotropic affect is disclosed, employing protoberberine alkaloids such as berberrubine or tetrahydropalmitane, alone or in combination with cardiac glycosides such as ouabain, digoxin, digitoxin or delanoside.

18 Claims, 17 Drawing Sheets

COMPOUNDS, COMPOSITIONS AND METHOD OF TREATMENTS FOR IMPROVING CIRCULATORY PERFORMANCE

This application is a continuation of application Ser. No. 378,122 filed May 14, 1982, now abandoned.

This invention relates to berberine-type alkaloids, particularly protoberberine drug compositions and their use in the treatment and diagnosis of circulatory disorders. The compounds of the invention are of special interest in prophylactic, therapeutic and other applications to prevent, minimize, control, alleviate, corect, remedy and so on, various disorders or symptoms of circulatory disorders, including cardiovascular origins or types. The invention relates in terms of subjects (or patients) to the field of mammals, i.e. human and veterinary fields.

The invention also encompasses distinct and valuable embodiments like compositions (and compounds and methods of use) for chronic and acute heart failure and other pathologic states that will benefit from an improvement in cardiac performance; for the treatment of shock (cardiogenic and non-cardiogenic shock); for the treatment of arrythmias (whether of natural causes or caused by a drug); for increasing the usefulness of cardiac glycosides (like of the digitalis types) including broadening their usually limited therapeutic index; for controlling or correcting A-V (atrio-ventricular blocks, to be defined later herein) block in mammals.

The unique, unobvious and remarkable aspects of the invention are quite numerous and will become apparent hereinafter, but at the outset it is most noteworthy that the compounds of the invention are antiarrhythmogenic, a remarkable utility in and by itself. Another aspect, is that the compounds of the invention have a remarkable combination of beneficial properties, such as, concurrently, having a positive inotropic effect and being antiarrythmogenic. Another unusual aspect is that the compounds of the invention are useful both in acute ventricular failure and also in chronic congestive heart failure. These aspects are of course described in greater detail hereinafter.

The invention also relates to other biochemical or biomedical applications. The other aspects, to which the invention relates, will become apparent to one of average skill in the art from the teaching herein.

One important, but not the only important field to which the invention relates is the cardiovascular field, both in humans and animals. Today cardiovascular diseases, which have reached epidemic proportions, account for a very high proportion of all deaths in the world, especially in industrialized nations. Approximately one of every five persons has some form of cardiovascular ailment such as heart disease, cerebrovascular disease or hypertension.

Cardiovascular disease not only is fatal but causes prolonged suffering and disability in even a larger proportion of the population. In the United States alone, cardiovascular disease was responsible for almost one million fatalities in 1979, well over one-half of all reported deaths. Almost 5 million persons afflicted with cardiovascular disease are hospitalized annually. The cost of this disease in terms of human annual costs due to morbidity amount to over 8 billion dollars. Braunwald, *Heart Disease, A Textbook of Cardiovascular Medicine,* W. B. Saunders Company, Philadelphia, 1980 ("Braunwald") which is incorporated herein by reference. For further details relating to disorders of the heart, reference is made to *Harrison's Principles of Internal Medicine,* Thorne, Adams, Braunwald, Isselbacher and Petersdorf, McGraw-Hill Book Company, 8th Ed., Part 7, ("Harrison's") *Disease of the Organ Systems, Disorder of the Heart,* Chap. 231 through 248, which are referred to specifically herein and incorporated herein by reference.

Reference shall also be made herein to the following clinical books, namely *Veterinary Pharmacology and Therapeutics,* Jones, Booth and McDonald, Iowa State University Press, 4th Ed., 1977; Physicians' Desk Reference "PDR" Medical Economics Company, 36th Ed. 1982; and *Veterinary Pharmaceuticals and Biologicals,* "VPB", 1980/1981, Aronson, Harwal Publishing Company, Media, Pa., 1980.

The direct cardiac action of drugs may be divided into four major areas: (1) an effect on contractility (inotropic effect), reflecting alterations in the myocardial force-velocity relation at any given initial muscle length; (2) an effect on heart rate expressed as an alteration in the rhythmicity, i.e., the frequency of discharge of normal pacemaker tissue, generally in the sinoatrial node; (3) an effect on conductivity, i.e., on the velocity with which the depolarization wave travels through the myocardium and the atrial ventricular conduction system; (4) an effect on irritability, i.e. the tendency to provoke ectopic pacemaker activity, which is dependent on the rate of diastolic depolarization and the threshold potential.

One of the most serious consequences of all types of cardiovascular diseases involves the pathophysiological state in which the heart fails in its prime function as a muscle acting as a pump. In general, heart failure is the result of severe primary depression of myocardial contractility or extreme ventricular hemodynamic overload combined with secondary diminution of the contractile state. For a description of the basics and disorders of the myocardial function, especially cardiac contraction see Harrison's, chapter 236.

Knowledge of the biochemical and physiological changes in heart failure has advanced considerably in recent years. Unfortunately, the development of pharmacological agents with clinically useful positive properties on cardiac contractility (positive inotropic agents) has not kept pace. Nearly two centuries have passed since W. Withering described the cardiovascular effects of *Digitalis purpurea* in 1787. Since then, the basic treatment of congestive heart failure remains with the cardiac glycosides as is described in greater detail herein. Although literally hundreds of cardiac glycosides have been investigated, not one has been found with a wide therapeutic index. The most commonly used cardia glycosides digoxin and digitoxin, have a very narrow therapeutic index of less than 2, with life-threatening cardiac arrhythmias as the first manifestation of toxicity. It is clear that a cardiotonic agent with a wide therapeutic index is needed, especially one that does not have the drawbacks of the glycosides at all or has them at least to a milder extent.

For the treatment of vascular diseases and the pharmacology of cardiac glycosides, reference is made here to Braunwald, Chapter 16, pages 515–538; Harrison, chapter 239, pages 1207–1210 and Goodman and Gilman, *The Pharmacological Basis of Therapeutics,* MacMillan Publishing Co., Inc., 5th Ed. which is incorporated herein by reference, 1975, Section VI, pages 653–682, ("Goodman").

Because the cardiac glycosides are the classical most common positive inotropic agents, a further discussion is presented below.

The catecholamines like norepinephrine, isoproterenol, dopamine and dobutamine have a limited role in the treatment of patients with chronic congestive heart failure. They are inactive orally and have a short duration of action when given intravenously. Their major use is in the treatment of acute ventricular failure such as a low cardiac output state after cardiac surgery and shock associated with sepsis or acute myocardial infarction. The arrhythmogenic and calorigenic properties of the catecholamines and lack of activity in patients pretreated with beta-adrenergic blocking agents, such as propranolol further limit the use of these agents.

The positive inotropic activity of glucagon was first demonstrated by Farah and Tuttle more than 15 years ago. Since then there has been interest in the possible role of this agent in the treatment of congestive heart failure. Although the initial clinical studies with glucagon were promising, further evaluation indicated that the clinical role of glucagon as a cardiotonic agent was limited. Glucagon was found to be inactive in patients with chronic congestive heart failure.

Other drugs which play a role in the treatment of heart diseases are the beta-adrenergic blocking agent, often used as antiarrhythmic agents. The most commonly used is propanolol, Goodman, chapter 26 and pages 609-704. Recently it was reported that Timolol, a beta-blocker was approved by the Food and Drug Administration ("FDA") as preventive against recurrence in patients who had suffered a first heart attack. *The Wall Street Journal,* Nov. 27, 1981.

Amrinone, a 5-amino-[3,4'-bipyridin]-6(1H)-one, a non-glycoside and non-catechol in nature, has been reported to have positive inotropic effects. Farah, Alousi, New Cardiotonic Agents: A Search For Digitalis Substitute *Life Sci.,* 1978; 22: 1139-48; Alousi, Farah, Lesher, Opalka Jr., Cardiotonic activity of amrinone— Win 40680 (5-amino-3,4'-bipyridin-6(IH)-One)), *Circ. Res.* 1979; 45: 666-77; DeGuzman, Munoz, Palmer, Davolos, Alousi, Clinical evaluation of amrinone—a new inotropic agent (abst), *Circulation* 1978; 58 (Suppl II): 11-183; Benotti, Grossman, Braunwald, Davolos, Alousi, Hemodynamic assessment of amrinone, a new inotropic agent, *New Engl. J. Med.* 1978, 299: 1373-7, LeJemtel, Keung, Sonnenblick, Ribner, Matsumoto, Davis, Schwartz, Alousi, Davolos, Amrinone: a new non-glycosidic, non-adrenergic cardiotonic agent effective in the treatment of intractable myocardial failure in man, *Circulation* 1979, 59: 1098-104.

It was recently reported that an application for a NDA has been filed with the FDA for Inocor, a brand of amrinone. Previously, clinical trials had been suspended because the drug promoted blood platelet aggregation, *The Wall Street Journal,* Oct. 28, 1981.

Recent calcium antagonists, like verapamil and nifedipine have been proposed to affect coronary perfusion, primarily by direct action on the coronary vasculature. They too have hemodynamic features which are not desirable. For instance, verapamil is known to reduce contractility and may induce atrio-ventricular block.

Diuretics are also used for the management of heart failure. Such duretic therapy is not without complications. Braunwald, page 544 and seq.

It is evident, from the state of the art, that there is a serious need for a effective drug for the treatment of heart and vascular diseases, especially for a positive inotropic drug.

There is no teaching or recognition in the prior art of a berberine alkaloid which is cardiotonic, positive inotropic, and which has the spectrum of cardiovascular properties of the compounds or compositions disclosed herein. Nor is there such teaching or recognition of the therapeutic treatments disclosed herein. There is no teaching or disclosure of compounds (or compositions -or methods of use-) like those of the invention which have the combination of properties disclosed herein or of certain specific properties disclosed herein or which naturally flow or result from these properties.

A review of the state of the art shows the following:

1. Akhter, Sabir, Bhide: "Possible Mechanism of Antidiarrheal Effect of Berberine", *Indian J. Med. Res.* 70: 233-241, 1979. Possible mechanism of the antidiarrheal effect of berberine was studied. Subjects were dogs and rats.

2. Creasy, W. A.: "Biochemical Effects of Berberine", *Biochem. Pharmacol.* 128: 1081-1084, 1979. Berberine inhibits the biosynthesis of DNA, RNA, proteins and lipids, as well as the oxidation of glucose to $CO_2$ when incubated with S180 cells in vitro. Also tested for inhibitory activity: thalicarpine and d-tetradrine.

3. Cohen, H. G. Seifen, E. E., Straub, K. D., Tiefenbach, C., Stermitz, F. R.: "Structural Specificity of the NaK-ATPase Inhibition by Sanguinarine, an Isoquinoline Benzophenanthridine Alkaloid", *Biochem. Pharmacol.* 27: 2555-2558, 1978. Discussion of structural specificity of the NaK-ATPase inhibition by sanguinarine, an isoquinoline benzophenanthridine alkaloid by comparing the compound to other quinolines and isoquinolines including berberine. Berberine is inactive with respect to inhibition of NaK-ATPase activity. Study of acridine, acriflarine chloride, protopine, capaurine, corycavine oxalate, coralyne chloride, corydaline, ethidium bromide, d-tetrahydropalmatine, boldine, chelidonine, laudanosine, hydrastine, emetine hydrochloride, nitidine and fagaronine yielded varied results.

4. Davidson, M. W., Lopp, I., Alexander, S., Wilson, W. D.: "The Interaction of Plant Alkaloids with DNA. II. Berberinium Chloride", *Nucl. Acid Res.* 2697-2712, 1977. Other substances studied include quinacrine, quinoline methanol, mefloquine, putrescine, coralyne and proflavine. Systems studied include cows and chickens. Data suggests that a large portion of the berberinium ring system intercalcates into DNA.

5. Sheppard, H., Brughardt., C. R.: "The Dopamine-sensitive Adenylate Cyclase of the Rat Caudate Nucleus. The effect of Aporphines and Protoberberines", *Biochem. Pharmacol.* 27: 1113-1116, 1978. Protoberberines are fairly potent as inhibitors of the DA-cyclase with little effects on the beta system. Aporphine analogues were tested.

6. Kovar, J., Skursky, L: "Fluorescence Study of Liver-Alcohol-Dehydrogenase Complexes with Berberine and Other Ligands", *Eur. J. Biochem,* 40: 233-244, 1973. Dissociation constant of liver-alcohol-dehydrogenase-berberine complex was determined. Composition study of complex made with NAD, NADH, o-phenanthroline, pelargonic and capric acids. Fluorescence of berberine found to be typical for hydrophobic probes, indicating that berberine interacts with a hydrophobic site of the liver-dehydrogenase enzyme.

7. Kulkarni, S. K. Dandiya, P. C., Varandanu, N. L.: "Pharmacological Investigations of Berberine Sulfate", *Japan. J. Pharmacol.* 22: 11–16, 1972. Berberine sulfate found to have anti-amoebic action as well as antiacetylcholine, anti-histamine and dose-related spasmolytic effects in comparison study with vioform and carbarsone. Systems tested include rats, rabbits, guinea pigs, frogs and dogs.

8. Dutta, N. K., Marker, R. P. Rao, N. R.: "Berberine in Toxin-Induced Experimental Cholera", *Br. J. Pharmacol.* 44: 153–159, 1972. In tests performed in rabbits, berberine found to be both vibriostatic and effective against choleragenic toxin.

9. Desai, A. B., Shah, K. M. Shah, D. M.: "Berberine in Treatment of Diarrhea", *Indian Pediatr.* 8: 462–465, 1971. Berberine found to be an effective tool against acute-gastroenteritis caused by different organisms.

10. Shanbhag, S. M., Kulkarni, H. J., Gaitonide, B. B.: "Pharmacological Actions of Berberine on the Central Nervous System", *Japan. J. Pharmacol.* 20: 482–487, 1970. In tests on mice, rats and cats, berberine found to act as a sedative, potentiating pentobarbitone sleeping time. Berberine found to be devoid of tranquilizing, anticonvulsant and analgesic properties, nor does it modify morphine analgesia or barbiturate hyperalgesia.

11. Fukuda H., Watanabe K., Kudo T., "Some Observations on the Cardiovascular Effects of 9-Substituted Berberines", *Chem. Pharmaceut. Bull.* 18: 1299–1304, 1970 is a report on a study of certain active principle extracted from the plant *Coptis japonica*. This type of berberine and the 9-substituted alkoxy derivatives were tested for cardiovascular effect in rats, toads and muscle preparations. No change in blood pressure from normal pressure after short transient hypotension (with a minimum dose of 0.1 mg/kg in rats) was observed. No change in heart rate was observed (as shown by the ECG recordings). The hypotension was attributed to depression or decrease of contractility of the heart. Where the substitution in the 9-position is —OH, a transient hypertension is caused. For compounds with O—n—$C_8H_{17}$ and O—n—$C_{12}H_{25}$ substituents no transient (hypo- or hypertension) or other effect on blood pressure were observed. This type of compound generally had no effect or decreased in blood flow, thus suggesting a general increase in peripheral resistance. At 30 mg/Kg, (i.p.) this type of berberine extract was lethal.

12. Homma, N., Kono, M., Kadohira, H., Yoshihara, S., Masuda, S.: "The Influence of Berberine Chloride on the Intestinal Flora in Infants", *Arzneimittel-Forsch* 11: 450–454, 1961.

13. Schein, F. T., Hanna, C.: "The Absorption, Distribution and Excretion of Berberine", *Arch. Int. Pharmacodyn.* 126: 317–325, 1960. In studies in the rat, berberine is found to initially concentrate in the animal's pancrease, heart, liver, omental fat and kidney.

14. Jang, C. -S.: "The Action of Berberine on Mammalian Hearts," *J. Pharmacol. Exp. Ther.* 71: 78–186, 1941. Studies on cat, rabbit and dog hearts show that berberine in low and moderate dosages increases heart rate and coronary flow. Little effect on cardiac output was observed. In large doses it depresses the heart. The cardio-inhibitory action of acetylcholine is potentiated by small doses of berberine but antagonized by moderate and large doses. Doses of berberine which are antagonistic to acetylcholine are also antagonistic to pilocarpine but not to KCl.

15. Mercier, F., Delphaut, J., Blache, P.: "Effects Pharmacodynamiques Compares de la Papaverine, de la Cryptopine et de la Berberine", *Comptes Rendus. Soc. Biol.* 127: 1022–1024, 1938. Study of effects of berberine, cryptopine and papaverine on blood pressure the nervous system, respiration, the heart and intestine, undertaken in dogs and rabbits. The three compounds exhibited comparable effects on blood pressure, respiration and the heart. In the intestine and nervous system, berberine and cryptopine acted similarly, and opposite to papaverine, which results were attributed to the chemical similarity of berberine and cryptopine. In small doses, berberine had a positive inotropic and chronotropic effect on the heart which was suppressed by the vagus section but was not modified by the injection of sparteine or yohimbine. In larger doses berberine depressed heart's contractility.

16. Soto, M., Sivori, P. N.: "Accion del Sulfato de Berberina Sobre el Corazon de Maniferos," *Rev. Assoc. Med. Argent.* 47: 3062–3068, 1933.

17. Soto, M., Sivori, P. N.: "Accion Sobre el Aparato Circulatorio y Sobre la Respiracion del Sulfato de Berberina," *Rev. Assoc. Med. Argent.* 47: 2492–2501, 1933.

18. Chopra, R. N. Dikshit, B. B., Chowhan, J. S.: "Pharmacological Action of Berberine", *Indian J. Med. Res. 19: 1193–1203, 1932.* Study of berberine, its toxicity, absorbability by G.I. tract, effect on movement of G.I. tract, effect on cardiovascular system, vasomotor center, respiratory system, urogenital system; and its effectiveness against malaria and oriental sore are discussed. Systems studied include cats, dogs, rabbits, frogs and rats. Berberine effects a sharp fall of blood pressure associated with an increase in the volume of the system, intestines and kidneys as well as dilation of blood vessels.

19. Perkin: "Epiberberine", *J. Chem. Soc.* 113: 503–505, 1918. Nomenclature and structure of berberine and epiberberine.

20. Williams, W. W.: "The Effects of Hydrastis and Its Alkaloids on Blood Pressure". *J. Amer. Med. Assn.* 50: 26–30, 1908. Study of hydrastine, berberine and hydrastinine on dogs, turtles and frogs. Discussion on drugs' effects on blood pressure, the heart, kidney and spleen volume, and respiration.

21. Trendelburg, P.: "Bestimmung des Adrenalingehaltes in noronalem Blut sowie Abklingen der Wirkung einer ennalegen intravenosen Adrenalininjektion mittels physialogisher messmethods." *Arch. Exp. Pathol. Pharmacol.* 63: 161–176, 1910.

22. Mani, R. S., Noronha, O. P. D.: "Preparation of Radioiodinated/131I/Berberine," *Radiochem. Radioanal Letters* 5: 119–123, 1970 Radioioiodinated/131I/-Berberine has been prepared by the carefully controlled iodination of berberine sulphate using carrier-free sodium iodide/131I/and hydrogen peroxides followed by ion-exchange purification.

23. DAS Gupta, Dikshit: "Berberine in the Treatment of Oriental Sore" *The Indian Medical Gazette*, pages 67–70, February 1929. Berberine sulphate inhibits Leishmania tropica.

24. Kamat, S. A. "Clinical Trials with Berberine Hydrochloride For the Control of Diarrhea in Acute Gastroentenitis. *J. Assoc. Phys. India* 15: 525–529, 1967. Berberine hydrochloride was found to be effective in arresting diarrhea.

25. Skinner, Basil, "The Isomerization of Berberine and Cotarnine Bases in Presence of Alkali. *J. Chem. Soc.*, 823–827, 1950. Study of aqueous and alcoholic solutions of berberine.

26. Bevalot, E, Leboeuy, M., Bouquet, A., Cave, A.: "Alcaloides des Annonacees: Alcaloides des Ecorces de Tiges et de Racines de Pachypodanthium confine, Engler et Diels." *Annales Pharmaceutiques Francaises,* Vol. 35, No. 1–2: 65–72 (1977). Study of alkaloid content of stem and root-barks of *Pochysodanthium confine.* The authors disclose six alkaloids: three tetrahydroprotoberberines, and three, 7-hydroxy aporphines.

27. Schewe, T., Muller, W. "Hemonung der Atmungskette durche die Alkaloide Berberinsulfat, Alpinigen und Tetrahydropalmatin." *Acta Biol. Med. Germ.,* Vol. 35, 1019–1021, (1976). Study of alkaloidal inhibition of the NADH oxidase system of electron transfer particles in beef heart.

28. Benotti, J. R., Grossman, W., Braunwald, E., Davolos, D. D., Alousi, A. A.: "Hemodynamic Assessment of Amrinone", *The New England J. of Med.,* Vol. 299, Nov. 25, 1978. Amrinone, a new bipyridine derivative, exhibits a positive inotropic action in experimental preparations and is effective when administered orally to dogs. Amrinone was further discussed above.

29. Miller, R. R., Vismara, L. A. Williams, D. O., Amsterdam, E. A. Mason, D. T.: "Pharmacological Mechanisms for Left Ventricular Unloading in Clinical Congestive Heart Failure. Differential Effects of Nitroprusside, Phenotalamine, and Nitroglycerin on Cardiac Function", *Circulation Res.* 39: 127–133, 1976.

30. Arentzen, C. E. Rankin, J. S., Anderson, P. A. W., Feezor, M. D., Anderson, R. W.: "Force Frequency Characteristic of the Left Ventricle in the Conscious Dog", *Circulation Res.* 42: 64–71, 1978. Study of three systemic vasolidators, nitroprusside, phenotalamine, and sublingual nitroglycerin. The three produced disparate modifications of LV function by their differing alterations of preload and impedance.

United States and foreign patents found which discuss berberine type compounds are the following.

U.S. Pat. No. 3,894,027 discloses a process for resolving racemic reticuline which is useful as a precursor of pallidine, sinoacutine, coreximine and the berberine alkaloids.

U.S. Pat. No. 3,884,911 discloses a derivative of berberine formula wherein RCO represents a cinnamoyl group which may be substituted with chloro, acetoxy, methoxy, or methylenedioxy which inhibit transplanted sarcoma strain in mice.

U.S. Pat. No. 3,865,830 thiophosphamide derivatives of isoquinoline alkaloids which have pharmacological activity.

U.S. Pat. No. 3,272,707 discloses quinolizine derivatives having tranquilizing, antidepressant and antiemetic activities.

U.S. Pat. No. 3,420,834 discloses berberine derivatives having tranquilizing and analgesic properties. The compound is obtained as a mixture with analogs.

U.S. Pat. Nos. 3,426,027 and 3,267,107 disclose berberine derivatives having anticonvulsant, analgesic and tranquilizing activities.

U.S. Pat. Nos. 3,910,938, 3,884,911, 3,920,665 and 4,033,966 disclose berbine derivatives which inhibit transplanted sarcoma strain in mice.

U.S. Pat. No. 4,087,426 discloses berberine and protoberberine analogs for treating uterine hemorrhage.

U.S. Pat. No. 4,200,629 deals with a process for extracting berberine from plants which contain the alkaloid. A product results which has activity for inhibiting the growth of fungi.

U.S. Pat. Nos. 3,943,251 and 3,903,282 disclose the use of berberine for dilating human eye pupils.

U.S. Pat. Nos. 2,003,204, 2,052,150, 2,486,937 and 3,023,147 disclose digitalis derivatives and methods for their production.

Japanese disclosure No. 39-21529 discloses 9-substituted berberine derivatives which have a stronger enterobacterial action than berberine. Japanese disclosure No. 45-4992 discloses 13-alkyl substituted berberine derivatives which have antiulcer activity.

French Pat. No. 1,568,738 discloses a new process for the preparation of tetracyclic bases including 2,3,9,10,11-pertomethoxy berberine.

British Pat. No. 1,265,627 discloses 13-methyl-7,8,13,13a-tetradehydro-2,3,9,10-tetramethoxy berberine as an anti-peptic ulcer ingredient.

This list is not represented to be complete but it contains those patents and articles which are presently available.

A discussion of cardiac glycosides follows as an introduction to the compounds of the invention and of a discussion of relevant properties and biological effects.

Cardiac glycosides of clinical importance vary in structure—and in cardiac effects—depending upon the botanical source from which they are extracted. Indeed, it has been reported that the terminology employed in the literature is confusing and awkward because the names refer to botanical origins rather than to exact chemical structures. Goodman, pages 654, 655. It has been shown that cardiac glycosides exist in plants as precursors called "native", "natural", or "genuine" glycosides. The three major botanical sources of cardiac glycosides of clinical importance are digitalis, strophanthus and scilla (squill). *Digitalis purpurea* and *digitalis lanata* are the recognized source for Digitoxin, Gitoxin and Gitalin. *Digitalis lanata* is the recognized source for Digotoxin, Gitoxin and Digoxin. *Strophanthus gratus* is the recognized source for ouabain.

Official preparations available for clinical use in the United States are the following: digitoxin, digoxin, lanatoside C, deslanoside, acetyldigotixin, powdered digitalis and ouabain. See Goodman, pages 672–676. See the PDR, pages 211, 310.

Likewise, alkaloids vary considerably depending upon the origin of the plant. See the Isoquinoline Alkaloids, Chemistry and Pharmacology, Shamma, Academic Press, New York 1972, Chapter 10 and the Chemistry of Isoquinoline Alkaloids, Tetsuji Kametani, Elsiver Publishing Co. New York, 1996.

The invention which has several embodiments to which some were referred to above; others are briefly described below; others will become apparent as the description proceeds.

An embodiment of the invention relates to isoquinoline, especially protoberberine alkaloids, their compositions which have a biological effect, especially in the treatment of cardiovascular disorders, heart failure, cardiac arrhythmias, shocks of circulatory nature, increasing contractility of the heart of mammals, improving aortic blood flow, and decreasing heart rate and systemic arterial pressure, reducing afterload of the left ventricle, decreasing preload in the left ventricle, decrease in calculated vessel peripheral resistance, decrease in mean arterial pressure and decreasing arrhythmias. These effects may be obtained to varying degrees, concurrently or not, with the individual compounds (compositions and methods of use) of the invention.

Of course, contemplated by the invention are compositions using one or more of the compounds of the invention, in which event, certain of the properties or effects can be synergistic or otherwise.

With respect to the embodiment of the invention which relates to the treatment of cardiovascular disorders, the protoberberine type alkaloids of the invention are useful in the treatment of congestive (or chronic) heart failure. Moreover, the protoberberine type alkaloids of the invention are useful in acute heart failure (cardiogenic shock being its more severe manifestation). This is an important distinction over the digitalis type glycosides which are known to be ineffective for treatment of cardiogenic shock. This is also an important advantage of the compounds of the invention in that the treatment of a patient can be continued with the same drug (one of the compounds of the invention) whereas in traditional therapy with digitalis or others, this is not possible.

The present invention relates to protoberberine alkaloids and their use both in the pharmacological treatment of cardiovascular disorders and as a diagnostic tool. The compounds of the invention have a strong positive inotropic effect, increase the aortic blood flow, decrease the calculated total peripheral resistance of vessels and are free of the drawbacks of digitalis, as has been mentioned above. The compounds also have a broad therapeutic index; that is a very small amount is effective for the desired effect and very large dosages are not toxic.

The compounds and biologically active compositions of the invention are useful for the treatment of congestive or chronic heart failure and also acute heart failure and/or cardiogenic shock. Moreover, states of systemic arterial hypotension, low cardiac output and shock of other origins with increased peripheral vascular resistance and/or decreased cardiac output will also benefit from this therapy.

Another embodiment of the invention relates to the use of the compounds of the invention on the control of arrhythmias. The compounds and biologically active compositions of the invention are useful in the treatment of cardiac arrhythmias. The scope (and types) of cardiac arrhythmias in which they are active is very ample, since they are active in arrhythmias provoked by acute coronary artery occlusions as well as pharmacologically produced or stimulated or induced arrhythmias by arrhythmogenic drugs. They may be arrhythmias provoked by "reentry" or of the "automatic" types. The compounds of the invention are effective both in preventing and in interrupting (including arresting or stopping) arrhythmias. They are effective on ventricular arrhythmias and on supraventricular arrhythmias. In the former category, they were active on premature ventricular ectopic beats, bigemini, ventricular tachycardia and ventricular fibrillation. In the latter category, they were active in atrial fibrillation and atrial paroxysmal tachycardia. The effect of the compounds of the invention as antiarrhythmogenics is a remarkable effect.

With respect to cardiac disorders, depression of ventricular function is the principal cause of heart failure, and improvement of myocardial contractility by means of cardiacally active glycosides have been the keystone in the management of this pathologic condition in humans and animals. These glycosides are typically represented by digitalis glycosides since these are the most commonly used, although other glycosides are equally active such as ouabain which is a stophantic glycoside. However, normally the generic term used (albeit somewhat incorrectly) is digitalis. Indeed, despite the value of diuretics and afterload-reducing agents, the glycosides remain the principal positive inotropic agents useful in long-term management of patients with congestive heart failure. Other drugs, known to act through stimulation of myocardial beta-adrenergic receptors such as the catecholamines and sympathomimetic agents, are very potent cardiac stimulants but for the most part may have serious adverse effects such as tachycardia, ventricular irritability and intensification of myocardial ischemia. Their use is restricted mainly to in-hospital intravenous treatment of cardiac shock and they are not given orally for chronic congestive heart failure. A major therapeutic advance in the medical treatment of congestive heart failure awaits discovery; namely, an effective, non-toxic drug that increases myocardial contractility without adverse effects such as increase in peripheral vascular resistance, decrease in coronary flow arrhythmias and a treatment that is free of the adverse effect of digitalis.

In accordance with the invention, a group of protoberberine alkaloids and derivatives has been discovered which are found to exert a strong positive inotropic action, decreases peripheral vascular resistance, raises cardiac output, and is virtually free of the drawbacks of digitalis such as arrhythmias. The compounds of the invention have a significantly broader therapeutic ratio than digitalis type cardiac glycosides.

For a better understanding of the invention, a review of the pharmacological and cardiovascular properties of digitalis is provided below which will facilitate the comparison with the protoberberine alkaloids and derivatives of and used in accordance with the invention.

A large number of compounds have as their major pharmacological action the ability to alter cardiovascular function. The therapy of cardiac diseases, independently of the ethiology of these diseases, is aimed either to compensate the mechanical dysfunction of the heart which is the deterioration of the function of the heart as a pump (and is called heart failure); or treatment of the abnormal electrical stimuli (i.e. arrhythmias) which may cause a life threatening condition. The therapy of the latter is antiarrhythmic treatment. The most commonly used drugs are quinidine and procainamide. The treatment of cardiac arrhythmias can also be performed by propranolol, a beta-adrenergic blocking agent. Some other new antiarrhythmic agents are being either introduced or tested now. To treat the former condition (i.e. any form of heart pump failure) digitalis and certain other structurally closely allied drugs have in common a specific and powerful action on the myocardium that is unrivaled for the treatment of congestive heart failure.

More recently vasodilators have been proposed (perhaps to overcome or compensate a principal shortcoming of digitalis), to treat heart failure in a different manner, i.e. by reducing the afterload and thus improving performance not through a positive inotropic mechanism. These agents also reduce the preload (generally measured by left ventricular end diastolic pressure or pulmonary wedge pressure) which is generally elevated in patients with with congestive heart failure.

It is known that the main pharmacodynamic property of cardiac glycosides like digitalis is its ability to increase the force of myocardial contraction. The beneficial effects of the drug in congestive heart failure—increased cardiac output; decreased heart size, venous pressure, and blood volume—are explained on the basis of increased contractile force, that is, a positive inotropic action. Because digitalis often significantly slows the ventricular rate in atrial fibrillation, it was believed that the main effect of the drug was to slow the heart rate. However, it is reasonably well-established now that digitalis is principally effective in congestive heart failure, in contrast to non-congestive heart conditions, regardless of cardiac rhythm and it is thought that relief is not by virtue of cardiac slowing but by its direct action to increase the force of myocardial contraction. Cardiac glycosides are known to exert their inotropic stimulation by increasing the rate at which tension or force is developed. It is also known that the positive inotropic effect of digitalis is not dependent on catecholamine liberation or potentiation, for this has been demonstrated in chronically reserpinized dogs and in the presence of beta-adrenergic blocking agents.

It is believed that the action of digitalis on the "cardiac tone" is due to the fact that digitalis does increase the tone of the muscle during systole, that is, the force of systolic contraction is increased. But it is known that digitalis does not increase the resistance to stretch of the ventricles in diastole, not even in high concentrations. Digitalis is known to reduce the size of the failing heart because it increases the contractile power.

More recent studies have shown that digitalis improves performance at any given filling pressure of the heart. Digitalis increases cardiac output in patients with congestive heart failure and with "latent" heart failure, that is in subjects who had heart disease but were not yet in overt failure. But it has also been reported that in normal subjects digitalis causes an increase in total peripheral vascular resistance, mean arterial blood pressure, reduction in forearm blood flow and increases in venomotor tone. This is caused by combination of a moderate, direct vasoconstrictor action on both arteriolar and venous smooth muscle and a centrally mediated increase in sympathetic tone. This opposes the effects of increased cardiac contractility by increasing impedance to ventricular ejection. The two effects thus counteract each other, and there is essentially no change in cardiac output. As explained further below, the compounds of the invention differ markedly and advantageously in that respect. In contrast to normal subjects, in congestive heart failure, varying degrees of sympathetically mediated peripheral vasoconstriction already exist as part of the compensatory response. Thus, in patients with congestive heart failure, cardiac output increases, there is a reduction of peripheral resistance, an increase in blood flow, and a reduction of venomotor tone. Frequently there is no increase in arterial pressure. The effects of digitalis upon arterial pressure in patients with congestive failure are variable.

Digitalis is known to exert a negative chronotropic action, which in part is a vagal effect and in part is due to a direct action on the sinus pacemaker. The apparent suppression of pacemaker activity which may take place following high doses of digitalis is probably due not to the arrest of the pacemaker but rather to a sinoatrial block related to a depression of conduction. This is the reason why in patients with second degree atrioventricular block, digitalis may be harmful by inducing complete (third degree) block. The increase in the A-H interval is a well documented property of this drug which is the cause of these atrioventricular blocks. In patients who need this therapy for heart failure, digitalis frequently provokes abnormal rhythms due to its low therapeutic index. Practically all types of existing arrhythmias have been reported to appear as a result of digitalis intoxication: atrial premature beats, atrial tachycardia with block, nodal premature beats, junctional tachycardia, ventricular premature beats isolated or in different cyclical patterns being bigemini the most frequent, ventricular tachycardia, "bidirectional" ventricular tachycardia, finally ventricular fibrillation. It increases the duration of the P-R interval which when exaggerated is a toxic manifestation and constitutes first degree A-V block, thereafter, there may occur second degree A-V block, Wenckeback or Mobitz type, and the advanced 2nd degree A-V block may evolve to complete (3rd degree) A-V block.

The protoberberines of the invention do not show an increase in the duration of the A-V interval which is the basis of all the more advanced (and serious) A-V blocks. It will be also shown that the protoberberines did not increase spontaneously neither the A-H nor the H-V intervals which constitute the A-V interval while digitalis typically prolongs the A-H interval. Digitalis very characteristically depresses the S-T segments and shortens the corrected QT intervals (QTc). The protoberberines of the invention contrary to digitalis (and to beta adrenergic agonists) increase the QTc intervals and do not depress the S-T segments.

Many other side effects may occur with digitalis, the most common being those related to the gastrointestinal system: anorexia, nausea, vomiting, diarrhea. Neurological side effects are well known including coma.

Other drawbacks from the use of digitalis are headache, fatigue, malaise and drowsiness. Other neuropsychiatric effects have been noted. Vision has often been reported to be blurred. Experimental observation in animals suggests that digitalis preparations increase blood coagulability and heparin (in sodium or calcium form) has been recommended to be used to reduce the toxicity of digitalis and ouabain.

Digitalis, as had been noted above, is of little hemodynamic or clinical benefit in cardiogenic shock but is usually moderately effective in pulmonary edema and milder forms of heart failure secondary to myocardial infarction. Digitalis has variable effects on angina pectoris, reducing this symptom in the presence of cardiomegaly and heart failure but tending to increase it in their absence.

For more information regarding the pharmacology of digitalis and other similar cardiac glycosides, reference is made to "Goodman" pages 653 et seq.

An important problem arises in the diagnosis and treatment of digitalis intoxication. Digitalis is often used in situations where the toxic effect of the drug are difficult to distinguish from the effects of the cardiac disease.

The choice of the digitalis glycoside is important. The two main criteria in selection are speed of on-set and duration of cardiac action. Yet all of the digitalis products have approximately the same narrow therapeutic index. That is, the therapeutic dose is approximately 50–60% of the toxic dose. For maintenance therapy, prolonged duration of action is often desirable such as afforded by digitoxin; when more rapid elimination is required, then digoxin or lanatoside C are considered. Where emergency therapy and rapid on-set of action may be imperative ouabain, deslanoside and digoxin may also be used for this purpose. Digoxin is the most common preparation used in the United States.

Digitalis is reported to be the fourth most frequently prescribed drug in the United States. But it also has one of lowest margins of safety. A most serious shortcoming of digitalis is its narrow therapeutic range which is about 40 to 50%. It has been reported that there is no "non-toxic" cardiac glycoside.

Recently the first randomized trial of the effects of digoxin was conducted in 25 patients with heart failure (Lee D. C. S., Johnson, R. A., Bingham, J. B., Leahy, M., Dinsmore, R. E., Goroll, A. H., Newell, J. B., Strauss, H. W. and Haber, E. Heart Failure in Outpatients. A randomized trial of digoxin versus placebo. *New England Journal of Medicine,* 306: 799–705, (1982). It was found that based on a clinical scoring system, fourteen patients improved while eleven did not improve. Only patients with a third heart sound showed improvement independent of the severity of the heart failure. It is also of interest that there was a failure to increase the ejection fraction (done by multigated nuclide ventriculography) in these patients.

It is evident from the above discussion of the effects of digitalis that the drug does have a number of important shortcomings.

Since the compounds of and used in accordance with this invention are different from digitalis and allied cardiac glycosides, the above description of these glycosides is useful to set the compounds of the invention apart and show their differences over the prior art.

It is an object of this invention to provide a class of compounds which have a combination of advantageous properties over digitalis (and other cardiac glycosides).

It is a further object of the invention to provide a new class of compounds which may be designated generically as protoberberine alkaloids which are positive inotropic agents which are accompanied with other desirable properties. Other objects of the invention have been referred to above and others will become apparent from the following disclosure.

It is another object of the invention to provide a berberine-type compound (and pharmaceutical compositions which include same) which act on the mammal cardiac system differently or have different effects, than reported previously with natural or other "berberine".

A composition aspect of the invention comprises a biologically or pharmaceutically acceptable carrier and as the active component thereof, one or more of the isoquinolines alkaloids which are positive inotropes and have one or more of the therapeutic properties described (and the biologically acceptable salts of these compounds). The invention discloses also preferred compositions.

In a method aspect of the invention, the invention relates to a therapeutic method for increasing cardiac contractility, preferably accompanying this effect by one or more other therapeutic effects improving aortic blood flow, decreasing heart rate, decrease in arterial pressure, decrease in afterload of the left ventricle, decrease in the preload of the left ventricle, decrease in diastolic arterial pressure, decrease in total peripheral resistance and freedom of arrythmias which comprises administering at least one compound of the invention to an animal (e.g. a mammal), preferably a human (male or female) in a dose sufficient to cause a positive inotropic effect. Thus, as can be seen, the invention does encompass several embodiments, particularly the compounds of the invention that improve cardiac performance and minimize heart failure while they also are antiarrhythmics. Also the invention encompasses compounds which are antiarrhythmics that improves cardiac performance and minimize heart failure. Generally, drugs that are positive inotropic do not possess antiarrhythmic properties and antiarrhythmic drugs generally do not possess positive inotropic properties.

A compound which is both a positive inotrope while concurrently being antiarrhythmic, is, as far as could be determined, not known. Conversely, an antiarrhythmic which concurrently is a positive inotrope, is, as far as could be determined, not known. Thus, such a compound where both of these advantageous properties are coupled is not known. In addition, the invention encompasses interrupting (also stopping) and preventing digitalis-induced arrhythmias and concurrently improving the contractility of the mammalian heart, another unique aspect of the invention.

In one aspect of the invention, the administration is performed on a patient having congestive heart failure. In another aspect it is performed on a patient under cardiogenic shock. In another aspect of the invention, the therapy is given sequentially to a patient under cardiogenic shock and thereafter for cardiac maintenance therapy. In situations where a patient may be under therapy with a compound of the invention for congestive heart failure and then is subjected to congestive heart failure, appropriate therapy with a compound of the invention may be continued with a compound of the invention. Another embodiment of the invention encompasses the administration of the compounds of the invention together with digitalis to have additive action (or synergistic) on the positive inotropic effect and on treatment of heart failure.

Another embodiment of the invention encompasses the administration of the compounds of the invention together with digitalis to increase further contractility to treat heart failure and to prevent digitalis induced arrhythmias, thus improving the therapeutic ratio of digitalis and allowing a higher dose with less toxic (arrhythmic) effects.

Another embodiment is the administration of a compounds of the invention with the main objective to treat arrhythmias to prevent their occurrence or to interrupt (or stop) them in the acute or chronic phases, both of supraventricular and ventricular origins in all patients, especially in those patients who will benefit by the hemodynamic effects of the compounds of the invention, such as the positive inotropic effect or decrease in peripheral vascular resistance and increase in cardiac output; or in those patients in which the negative inotropic effects of the commonly used antiarrhythmic agents is disadvantageous or contraindicated. The versatility of the compounds of the invention and the unusual aspects of the invention are well illustrated by the above.

The compounds of the invention have a combination of beneficial properties generally associated or described as properties or effects on the cardiovascular system of mammals, both humans and animal. These properties may include a positive inotropic effect which can to varying degrees, in accordance with the invention, be associated (or accompanied by) other beneficial effects on the cardiovascular system like decrease in diastolic arterial pressure, decrease in total peripheral resistance and others described above.

Other effects of the compounds of the invention are physiologically distinct from the other beneficial properties; for instance the antiarrhythmic effect, the capability of controlling, minimizing, alleviating or preventing circulatory shock in a mammal (such shock having as its symptom a decrease on blood flow and/or oxygen supply).

In a further aspect of the invention it has been discovered that the compounds of the invention control atrial arrhythmias and reverses atrial fibrillation to sinus rhythm. Atrial fibrillation is detrimental to cardiac performance and also increases the risk of embolism.

The traditional therapy has been electric shock, quinidine and digitalis, all not as satisfactory as the therapy now made available here.

Other objects are or will become apparent from the disclosure.

TABLES AND FIGURES

The following are the Tables and Figures which further illustrate the invention.

| Number | Title |
|---|---|
| | TABLES |
| I | LV dP/dt (Protocol M) |
| II | Aortic Flow (Protocol M) |
| III | df/dt (Protocol M) |
| IV | Heart Rate (Protocol M) |
| V | Left Atrial Pressure (Protocol M) |
| VI | Left Ventricular End Diastolic Pressure (Protocol M) |
| VII | Systolic Pressure (Protocol M) |
| VIII | Diastolic Pressure (Protocol M) |
| IX | Effect of Ouabain on Aortic flow and peripheral resistance |
| X | Multiple Infusion of Berberine in a Dog Prepared as in Protocol M |
| XI | Systolic Pressure (Protocol RK) |
| XII | Diastolic Pressure (Protocol RK) |
| XIII | Comparison of Berberine, Berberrubine Tetrahydropalmatine, and Coreximine |
| XIV | Effect of Berberine on Ejection Fraction |
| XV | Effect of Berberine (0.2 mg/Kg/min) on Ejection Fraction (as done by MUGR) in Conscious Dogs with Acute Left Ventricular Failure |
| XVI | Effects of Berberine and Ouabain on Hemodynamics in Dogs with Acute Heart Failure |
| XVII | Effect of Berberine, Ouabain and the Combination of Both Peak LV dP/dt (numbers are percent increase compared to before treatment) |
| | FIGURES |
| I | Changes in LV dP/dt max During Continuous Intravenous Infusion of Berberine Hydrochloride |
| II | Changes in Pulse Pressure During Continuous Infusion of Berberine Hydrochloride |
| III | Changes in Aortic Flow During Continuous Infusion of Berberine Hydrochloride |
| IV | Changes in Heart Rate During Continuous Infusion of Berberine Hydrochloride |
| V | Effects of Continuous Intravenous Administration of Berberine Hydrochloride |
| VI | Effect of Berberine Hydrochloride on Ejection Fraction on the Conscious Dog |
| VII | Effect of Berberine Hydrochloride on Left Ventricular dP/dt in Heart Failure |
| VIII | Effect of Berberine on End Diastolic Pressure (LVEDP) in Heart Failure |
| IX | Effect of Berberine Hydrochloride on Total Peripheral Resistance in Heart Failure |
| X | Effect of Berberine Hydrochloride on Cardiac Output (CO) in Heart Failure |
| XI | Effect of Berberine Hydrochloride on Stroke Volume (SV) in Heart Failure |
| XII | Effect of Berberine Hydrochloride on "Frank-Starling Curve" in Heart Failure. Comparison of CO to LVEDP |
| XIII | Effect of Berberine Hydrochloride on "Frank-Starling Curve" in Heart Failure. Comparison of SV and LVEDP |
| XIV | Abnormalities of Circulatory Function. Schematic Representation from "Braunwald" |
| XV | ECG Wave and Intervals. Schematic Representation from "Braunwald" |
| XVI | Effect of Continuous Intravenous Administration of Berberine Hydrochloride on PR Interval In Anesthethized Dogs. |
| XVII | Effect of Continuous Intravenous Administration of Berberine Hydrochloride (0.7 mg/kg/min) on QRS Interval in Anesthetized Dogs. |

The compounds of the invention are berberines, more specifically protoberberines, as further described herein. The term protoberberine also herein includes the protoberberines known as tetrahydroprotoberberines and retroprotoberberines, quaternery amonium protoberberine dihydrobeberines, tetrahydropseudoberberines and dihydroprotoberberines. In the protoberberine alkaloids of the invention, substituents can be present at C-2 and C-3 and either at C-9 and -10 or at C-10 and -11 position. In certain instances, a hydroxyl or methoxyl may be present at C-1. A methyl group can be found at C-13, while in other cases an alcoholic hydroxyl is located at C-13 or at C-5.

The preferred compounds of and used in the invention may be represented by the following Formula I.

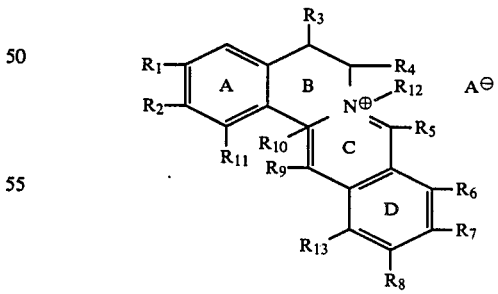

in which:

$R_1$ and $R_2$ may be the same or different and represent hydrogen, hydroxy, preferably a lower alkyl like methyl or a lower alkoxy like methoxy or ethoxy, aryloxy containing generally no more than 12 carbons but preferably 6 or 7 carbons like phenyloxy or benzyloxy, or when taken together $R_1$ and $R_2$ form an alkylene dioxy like a methylene dioxy group;

$R_3$ represents hydrogen, hydroxyl, preferably a lower alkoxy like methoxy or ethoxy or an aryloxy as described for $R_1$ or $R_2$;

$R_4$ represents hydrogen or preferably a lower alkyl like methyl;

$R_5$ represents hydrogen, preferably a lower alkyl like methyl, aryl like phenyl or arylalkyl (preferably alkyl where the alkyl preferably a lower alkyl) like benzyl;

$R_6$ and $R_7$ may be the same or different and represent hydrogen, hydroxy, preferably a lower alkoxy like methoxy or ethoxy, aryloxy containing no more than 12 carbons but preferably 6 or 7 carbons like phenyloxy or benzyloxy, carbamoyl —O(CO)NR$_{13}$R$_{14}$ when $R_{13}$ and $R_{14}$ are the same or different and represent hydrogen, preferably lower alkyl like methyl or ethyl, or aryl like phenyl, or when taken together $R_6$ and $R_7$ form an alkylene group like a methylene dioxy group;

$R_8$ represents hydrogen, hydroxyl, preferably a lower alkoxy like methoxy or ethoxy, aryloxy containing no more than 12 carbons but preferably 6 or 7 carbons like phenyloxy or benzyloxy;

$R_9$ represents hydrogen, preferably a lower alkyl like methyl, ethyl, lower alkyl substituted with methyl like $CH_2OH$, or hydroxyl;

$R_{10}$ represents hydrogen or an alkyl, like lower alkyl, like methyl;

$R_{11}$ represents hydrogen, hydroxyl, preferably lower alkoxy like methoxy or ethoxy;

$R_{12}$ represents hydrogen or preferably lower alkyl like methyl; and $R_{13}$ represents —CHO or an hydroxy alkyl, like hydroxy methyl.

Ring B may be unsaturated between carbons 5 and 6.

Ring C may be saturated between carbon 8 and the nitrogen or it may be saturated between carbon 13 and 14 to yield a tetrahydroberberine. Other degrees of positions of the saturation or unsaturation are possible.

The isomers are considered within the generic formula and the specific embodiments contemplates either the d,l-racemic mixture of the compounds or the specific d- or l-resolved form of the compound. It is contemplated that all forms of these racemates must be always of the same potency in all respects.

A— in the formula represents a biologically acceptable, especially a therapeutically acceptable anion such as to form salts of the compounds illustrated including the quaternary ammonium salts and the addition salts of organic or inorganic acids. Illustrative acids are inorganic strong acids like sulfuric, nitric, ethanedisulfonic, phosphoric, mono-, di- or tri-organicacids like citric, acetic, lactic, tartaric, sulfamic, succinic, fumaric, maleic, hydrochloric, hydrobromeric, alipatic or aromatic acids like benzoic and numerous others.

Following traditional nomenclature the rings are identified from A to D and the numbering of the carbon atoms as illustrated for canadine ((—)-tetrahydroberberine) below in Formula II.

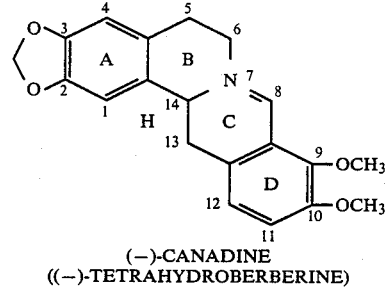

FORMULA II (—)-CANADINE
((—)-TETRAHYDROBERBERINE)

It will be noted that it is also within the contemplation of the invention that biological metabolite(s) resulting from the compounds of the invention, are also within the invention, which metabolites are responsible for the positive inotropic effect and at least one of the beneficial properties disclosed here. The definition of compounds of the invention includes such metabolites.

Within the general formula of compounds of the invention, certain classes are identifiable which are specifically interesting from the objectives of the invention. These are the classes which have a methylene dioxy group on ring A; those having one or two lower alkoxy substituents on ring D, those having a lower alkyloxy and a hydroxyl group on ring D, those having one or more, especially two lower alkoxy (like methoxy) substituents on both rings A and D and wherein $R_{10}$ is hydrogen, or the class represented by $R_1$ and $R_7$ being concurrently lower alkoxy, like methoxy while $R_2$ and $R_8$ are concurrently hydroxyl.

The invention also contemplates adding to the ring(s) or elsewhere or replacing one or more of the above named substituents by one or more halogens, like chlorine or other therapeutically beneficially active substituents which enhance or otherwise potentiate one or more of the desired properties of the compounds of the invention. Likewise, any of the above substituents can be an ester, an amido, amino, or other functional group which will have a desired therapeutic effect. Such a group may be inert, decrease one of the therapeutic effects (if this is desired) or a side effect (if one is noted which may be less desirable) or increase a particularly desirable one. All such compounds are intended and are contemplated and in the compounds of the invention.

It will be noted that certain subgroups or classes of compounds are preferable if certain therapeutic effects are specially sought after, whereas other classes or subclasses will be preferred if other therapeutic effects are especially sought after. Since the compounds of the invention have several types of therapeutic effects it will be apparent to one skilled in the art that the selection of the special species will depend in a certain measure on what effect is sought after most.

It will also be noted that the compounds of the invention (or the composition thereof) are used in a amount which brings about a positive beneficial therapeutic effect. These amounts will vary depending on the effect sought and on the particular species used. It will also depend on whether the compound is used for prophylactic or curative or maintenance therapy purposes; the first reason usually calling for a smaller amount, and the last, intermediate amounts. One skilled in the art, such as a physician or a veterinarian, will readily be able to prescribe the appropriate dosage for the particular purpose. Since the compounds of the invention have such a remarkably wide therapeutic ratio and low toxicity, the latitude available for appropriate dosage is large. Amounts as modes as 0.0001 mg/Kg of body weight of a compound of the invention can give a positive therapeutic effect; generally amounts over 1 g/Kg may be unnecessary, unless the clinician or physician deems it advisable. It is evident that the mode of administration influences also the dosage administered whether it is for instance by injection, oral or infusion, and if by ingestion or whether subcutaneous, intravenous or otherwise. None of these considerations will present an undue expermentation or problem for the physician or veterinarian.

The description of the synthesis of many of the compounds of the invention can be found in the literature. Examples of these include the synthesis of copistine (A. Klasek et al, *Tetrahedron Lett.*, p. 4549 (1969)), berberine (Kametani et al, *J. Chem. Soc.* (c) p. 2036 (1969)) and palmatine (Feist, Dschu, *Arch. Pharm.*, 263, 301 (1925)) where the C-ring is aromatic and there are 2, 1 or no methylenedioxy groups present in the molecule. Where the C-ring has been reduced, representative examples of synthesis include those for 1-tetrahydrocopistine (Klasek et al, *Tetrahedon Lett.* p. 4549 (1969)), cariadine (Russell, *J. Am. Chem. Soc.* 78, 3115 (1936)), tetrahydropalmatine (Brasher, Dietta, *J. Org. Chem.*, 26, 2231 (1961)) and coreximine (Kametani et al, *J. Chem Soc C*, 112 (1968). General syntheses for the aromatic protoberberines are disclosed in U.S. Pat. No. 3,910,938 and for the tetrahydro compounds in U.S. Pat. Nos. 3,272,707 and 3,426,027. The synthesis of tetrahydropalmatine methiodide, a typical quaternary amimonium salt is described by Narosimham and Bhide, *Chem. Ind.* (London), p. 621 (1969). Among the acceptable salts are the sulfate, nitrate, phosphate, citrate, acetate, maleate lactate, tartrate, succinate, chloride, bromide, iodide, benzoate and the like. The salts are prepared by methods known in the art.

Of interest, if further details with respect to synthesis or other aspects are needed for one skilled in the art, reference is made to *Shamma Isoquinoline Alkaloids Chemistry and Pharmacology*, Academic Press, New York, 1972 ("Shamma") and Tetsuji Kametani, *The Chemistry of Isoquinoline Alkaloids*, 1969, Hirokawa Publishing Co, Tokoy, Elsiver Publishing Co., New York, (especially chapter 10), both books being incorporated herein by reference.

Amongst the isoquinoline compounds of particular interest are the following classes: the protoberberines and retroprotoberberines, the protopines which are identifiable by $R_9$ representing an oxygen as illustrated in Shamma, chapter 18; the rhoedines and papaverrubines, the homoprotoberberines, as shown in Shamma, chapter 27. for purposes of this invention, the term berberine is generic to proto- and to homoberberines.

It is also contemplated in accordance with the invention that certain chemical functions or structures may be combined with the protoberberine structure of the compound of the invention to give compounds of promising cardiovascular, in particular, positive inotropic propertiesor the other desired effects disclosed herein. It is contemplated for instance, that one or more sugars (glycoside) be linked to the protoberberine structure. In this manner the resulting compound is capable of having enhanced potency and duration of action whether or not caused by increasing solubility. The sugar residue is capable of enhancing the stability of the protoberberine alkaloid in the biological system, e.g. in a patient, when used for treatment of cardiovascular or other disorders.

A preferred compound of the invention is berberine which has the properties described herein. For best reproducibility of properties, the synthetic, non-naturally occurring protoberberine products are preferred. Preferably, the protoberberines which have a purity of at least about 90%, most preferably at least about 99% pure.

A class of particular interest are the dehydroberberines which are not naturally occurring, i.e. synthetic, especially of a purity of over about 90%, more preferably of at least 99% purity. A particularly favored species is the dehydroberberine (synthetic) of at least 90%, preferably at least 99% purity. A species used was the hydrate ($2.5H_2O$). The anhydrous form is reported to have a molecular weight of 371.8.

It is to be noted that the premium placed on lack of side effects, purity, and other desirable properties discussed above (and herein) is specially desirable when human species are treated, whereas such strict requirements may be somewhat less necessary when animal species are treated, especially of the non-edible type. Typically bovine, equine, feline and swine and other animals are contemplated.

Included in the terms used above, (i.e. berberine, protoberberine, dehydroberberine, etc.) are the biologically, and especially the pharmaceutically or therapeutically acceptable salts of the above. Illustrative salts are described elsewhere herein. Salts generally used quite satisfactorily where the hydrochlorides, the sulfates and others.

Most preferred species are the berberrubine(s) (formula III below), berberine (formula IV below), tetrahydropalmatine (formula V, below) and coreximine (formula VI) below.

FORMULA III

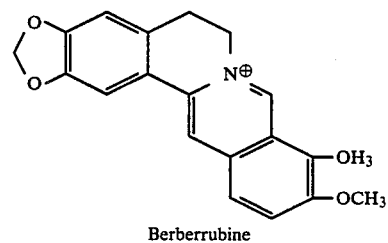

Berberrubine

FORMULA IV

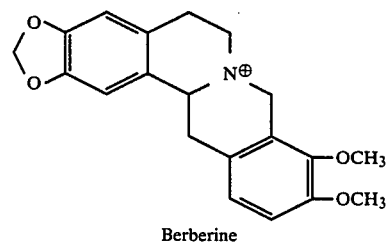

Berberine

FORMULA V

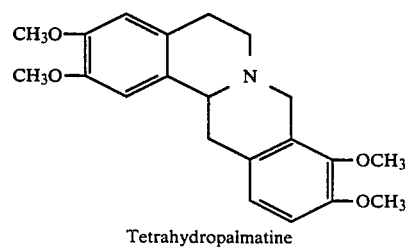

Tetrahydropalmatine

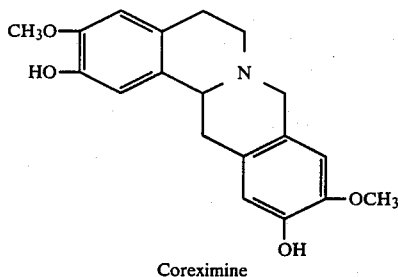

FORMULA VI

Coreximine

The favored isomer of tetrahydropalmatine is d-tetrahydropalmative but the d,l, mixture or l-tetrahydropalmatine is also useful. The favored isomer of coreximine is (−)-coreximine but the (±)-or (+)-coreximine is likewise useful.

Other typical compounds of and used in accordance with the invention are the following: berberrubine, berberine (umbellatine), d-tetrahydropalmatine, discretine, xylopinine(1-norcoarlydine), stepharotine, capaurimine, capurine, ophiocarpine, dehydrothalictrifoline, dehydrocorydaline, thalictricavine, thalictrifoline, (base II), isocorybulbine and alborine, and others disclosed herein.

The salts are generally a more convenient form for use. In practice the use of the salt form amounts to use of the base form. Pharmaceutically or biologically acceptable salts are salts whose anions are relatively innocuous to the animal organism in dosages used so that the cardiotonic or other desirable effect of the free base is not vitiated by the effects of the anions.

Mixtures of the compounds of the invention and of their salts may also be used as is contemplated within the invention. It is not within the contemplation of the invention that one skilled in the art should be able to avoid the spirit and scope of the invention by the use of a different salt or a different compound.

In clinical practice said compound or salt thereof will normally be administered orally or parenterally in a wide variety of dosage forms.

Solid compositions for oral administration include compressed tablets, pill, powders, and granules. In such solid compositions, at least one of the active compounds is admixed with at least one inert diluent such as starch, calcium carbonate, sucrose or lactose. These compositions may also contain additional substances other than inert diluents, e.g., lubricating agents, such as magnesium stearate, talc and the like.

As is known in the art, liquid compositions for oral administration include pharmaceutically-acceptable emulsions, solutions, suspensions, syrups and elixirs containing inert diluents commonly used in the art, such as water and liquid paraffin. Besides inert diluents such compositions may also contain adjuvants, such as wetting and suspending agents, and sweetening, flavoring, perfuming and preserving agents. According to the invention, the compounds for oral administration also include capsules of absorbable material, such as gelatin, containing said active component with or without the addition of diluents or excipients.

As is known in the art, preparations according to the invention for parenteral administration include sterile aqueous, aqueous-organic, and organic solutions, suspensions and emulsions. Examples of organic solvents or suspending media are propylene glycol, polyethylene glycol, vegetable oils such as olive oil and injectable organic esters such as ethyl oleate. These compositions can also contain adjuvants such as stabilising, preserving, wetting, emulsifying and dispersing agents.

As is known in the art, they can be sterilized, for example by filtration through a bacteria-retaining filter, by incorporation of sterilising agents in the compositions, by irradiation or by heating. They can also be manufactured in the form of sterile solid compositions which can be dissolved in sterile water or some other sterile injectable medium immediately before use.

As has been discussed above, the percentages of active components in the said composition and method for increasing cardiac contractility and the other properties can be varied so that a suitable dosage is obtained. The dosage administered to a particular patient is variable, depending upon the clinician's judgment using the following as criteria: the route of administration, the duration of treatment, the size and condition of the patient, the potency of the active component and the patient's response thereto. An effective dosage amount of active component can thus only be determined by the clinician considering all criteria and utilizing his best judgment on the patient's behalf. Like criteria shall guide the veterinarian.

It is within the contemplation of the invention as already referred to above, to selectively substitute or add to the rings, selected substituents which favorably influence the desired properties of the compounds and compositions used in the instant invention.

In summary, what is contemplated by the invention are those protoberberines, preferably of the one of the classes described which have a positive inotropic action (both in congestive (or chronic) heart failure and in cardiogenic shock in mammals (human or animals) (female or male), which inotropic action is preferably (but not necessarily), accompanied to at least to some degree, by one or more of the following cardiovascular effects: vasodilation or at least no increase in calculated peripheral vascular resistance, no increase in heart rate, increase in blood flow in the aorta, decrease of aortic pressure caused by peripheral vasodilation, reduction of afterload and freedom of arrhythmias and antiarrhythmic effect.

A preferred class of compounds are those which are antiarrhythmogenic, whether or not that effect is accompanied by other beneficial therapeutic effect like positive inotropic effect.

Preferred are those compounds which have a wide therapeutic index and those which differentiate themselves by one or more therapeutic properties from digitalis glycosides.

A typical compound of the invention, such as the type of berberine used, possesses a combination of advantageous properties. Berberine, in subjects without latent or overt heart failure, increases myocardial contractility and accelerates the blood flow in the aorta. Berberine also decreases the heart rate and diastolic aortic pressure by peripheral vasodilation.

Digitalis is known to contract blood vessels, increasing peripheral vascular resistance; also to cause centrally mediated increase in sympathetic tone. In contrast, the berberine used does not cause peripheral vascular constriction but causes a decrease in calculated peripheral resistance.

Berberine causes mean arterial pressure to decrease because the diastolic pressure is decreased. With digitalis, arterial pressure is increased.

In further contrast to digitalis, berberine is virtually free of cardiac side effects noted above for digitalis. Berberine does not cause any type of arrhythmia within the dosages administered. There is no premature ventricular beats or atrio-ventricular block.

Berberine is also different from beta-adrenergic agonists; these increase contractility but also increase heart rate. The invention therefore provides an important new class and use of positive inotropic agents.

Apart from and distinct from their cardiovascular inotropic effect, the compounds of the invention—and their compositions—are also useful in the treatment not only of cardiac shock, but also in certain stages of other types of shock (due to other initiating causes), like anaphylactic shock (for which epinephrine remains a primary therapeutic agent), hemorrhagic shock, non-hemorrhagic oligemic shock, distributive shock, septic shock, or shock due to metabolic, toxic or endocrine failures. These types of shock are generally the consequences of diminished blood volume, i.e. decreased cardiac output and decrease systemic arterial pressure generally accompanied by vaso or venoconstriction and tachycardia. Thus, the compositions of the invention by its positive inotropic effects and/or decrease in peripheral constrictions, provide an appropriate therapy to alleviate or control such shock situations.

The compounds of the invention also are useful as cardiac imaging agents. The compounds of the invention can be used for studies of the heart, anatomically and functionally. This effect of the compounds of the invention will be further discussed below.

The pharmacological and cardiovascular data of the compounds of the invention was obtained following the protocols described below, which are generally of the standard traditionally accepted types.

Certain terms are commonly used to describe the mechanical properties of cardiac muscle. For definition reference is invited to Braunwald, pages 431–452, which is incorporated herein by reference.

The usefulness of the compounds of the invention as positive inotropic agents, (and other uses as disclosed) is demonstrated by effectiveness in standard pharmacological test procedures, for instance in causing a significant increase in the cardiac contractile force in the anesthesized dog with virtually no increase or decrease in heart rate and blood pressure. Protocols used are described herein or by reference to standard medically accepted publications.

The term "contractility" or "inotropic state" has a different meaning than performance.

The term "contractility" is useful to identify a change in contractility (or inotropic state) of the heart as an alteration in cardiac performance that is independent of changes resulting from variations in preload or afterload. When loading conditions remain constant, an improvement in contractility will augment cardiac performance (a positive inotropic effect) while a depression in contractility will lower cardiac performance (a negative inotropic effect). The basal level of contractility is reduced in chronic myocardial failure.

The experimental work was carried out as follows: Twelve healthy adult mongrel dogs (20–30 kg) of both sexes were anesthetized with intravenous sodium pentobarbital (25 mg/kg). A left thoracotomy was performed through the fifth intercostal space. Catheters were placed to record left atrial, left ventricular and aortic pressures. Descending aortic blood flow was measured with an electromagnetic flowmeter. Heart rate (HR) was calculated using electrocardiographic recording, lead aVF. All parameters were recorded on a Gould polygraph.

The dogs were randomly assigned either to the control or to the treated group. Six of the dogs were in the control group and these dogs were infused with a placebo, namely the vehicle used for the drug tested.

The berberine used was a synthetic berberine (of a purity of 99%), HCl salt and 2.5 $H_2O$.

Berberine (as the hydrochloride salt) was administered to six anesthesized dogs (barbiturate). The dose was 0.7 mg/kg/min. intravenously infused during 5 minutes. This dose was repeated after 45 minutes.

Systolic arterial pressure was maintained at a constant rate using a reservoir full of blood under constant pressure connected to the femoral artery. Whenever the arterial pressure was not maintained constant in the work reported (and allowed to drop) appropriate reference is made herein to that fact.

Systemic arterial pressure was maintained at a constant rate in order to obtain accurate dP/dt since this parameter is of extreme importance in these studies. However, as a consequence, the vascular peripheral resistance, when described as a function of mean aortic pressure, was higher than if the pressure would be allowed to fall with the administration of the compound. Therefore, the reduction calculated total peripheral resistance is underestimated. Also dP/dt is less increased when bradycardia (lower heart rate) occurs and since heart rate was allowed to fall (which is the effect of the drug), the increase in dP/dt reported here is actually underestimated as compared to preparations in which heart rate would have been maintained constant.

The tables which follow (tables I through IX) are briefly summarized below.

Table I (Protocol M) shows the left ventricular maximum rate of pressure change (LV dP/dt) measured in $mmHg \times sec^{-1}$.

Table II (Protocol M) shows aortic blood flow velocity measured in $ml \times m^{-1}$.

Table III (Protocol M) shows the maximum rate change of aortic flow velocity (i.e. maximum flow acceleration) (maximum dF/dt) measured in $ml \times min^{-2}$.

Table IV (Protocol M) shows the heart rate (HR) calculated from the recordings of lead aVF of the electrocardiogram measured in $beat \times min^{-1}$.

Table V (Protocol M) shows the mean left atrial pressure (LAP) values measured in mmHg.

Table VI (Protocol M) shows the left ventricular end-diastolic pressure (LVEDP) measured in mmHg.

Table VII (Protocol M) shows the systolic aortic pressure (SAP) measured in mmHg.

Table VIII (Protocol M) shows the diastolic aortic pressure (DAP) measured in mmHg.

Table IX shows the effect of ouabain on aortic flow and calculated peripheral resistance.

Table X (Protocol M simile) shows hemodynamic changes in a dog following repetitive infusions (16 successive infusions, over five minutes of 3.5 mg/Kg of berberine) measurements taken at fifteen minute intervals at constant pressure.

For further details on the statistical method used here, see Snedecor, G. W. and Cochran, W. F.: *Statisti-* cal Methods, 6th ed., Ames, Iowa State University Press, 1967.

In Tables I through IX the results of these experiments are presented. The first two lines presents the studied parameter in absolute values, the third line representing the "t" values used in Student's t test for group observation, between the treated and control groups. The fourth line presents the level of significance. The next four lines give the values as changes ($\Delta$) from the value before treatment to the value after treatment. The third set of values represent the changes in percent.

The last two sets of two lines represent the paired t-test values and the derived p values obtained by analyzing the data from before the infusion of the drug (last set of two lines) or the placebo (next to last set of two lines), in the subsequent time interval (i.e. after infusion). Therefore, each dog serves as his own control, thus increasing the statistical value of the tests. In the control group it shows whether the value changes with time. Most importantly it shows whether berberine caused any changes in the treated dogs.

Table I represents dP/dt maximum of the left ventricle. The dP/dt values at constant systolic left ventricular pressure assess cardiac contractility. An increase in dP/dt indicates positive inotropic drugs.

The table summarizes the data of maximum dP/dt in mmHg/sec. Both groups of dogs started at the same level of dP/dt. A small increase in the dP/dt in the control group was observed. In the treated group a much more marked increase was observed.

As can be observed from the table, the difference between the control group and the berberine-treated group at the end of the experiment was 50%, which is statistically significantly higher. The difference in dP/dt, 2009±132 mmHg/sec in the control group and 2974±121 mmHg/sec in the berberine treated group shows that this index (dP/dt) of myocardial contractility was augmented by 50%. Both differences between the two groups as well as in the increase in this index of contractility in the berberine treated group at each time interval when compared to its value before administration of berberine was statistically significant with the p level of less than 0.01; thus there is a chance smaller than 1 per 100 that this difference is attributable to random occurrence.

The increase in myocardial contractility shown is a very remarkable for a drug which is not a beta-adrenergic agonist since it is not dependent on catecholamine increase in catecholamines in the blood or in the myocardial tissue.

Table II shows the data relative to the peak aortic blood flow velocity in the descending aorta measured with an electromagnetic flowmeter. Stroke volume (the amount of blood ejected by the left ventricle) is the area and the flow curve when measured in the ascending aorta. The performance characteristics of this flow meter have been described by McDonald in *Flow Meters for Pulsatile Flow in Blood Flow in Arteries* by McDonald, Williams & Wilkins, Baltimore, 1974, pages 209–237. In the data analysis, 0 blood flow was assumed at the end diastole.

As is observed from the last four lines in the control group, peak blood flow velocity did not change significantly; in the berberine-treated group, peak blood flow velocity increased significantly. The increase was nearly 50%.

The increase in blood flow is the most sought after effect in patients with heart failure since blood flow indicates an increase in cardiac performance. Indeed, the goal of the treatment is to increase the blood flow which as a consequence of heart failure is reduced.

For the role of aortic blood flow in the assessment of cardiac performance, see Braunwald, chapter 14, pages 472–484, incorporated herein by reference.

It is to be noted that since the systolic arterial pressure of the dogs was maintained constant, the data referring to aortic flow suggests berberine is not a vasoconstrictor. In contrast as has been noted herein before, it has been reported that digitalis and like cardiac glycosides have a vasoconstricting effect in the non-failing heart.

Table III shows the rate of aortic blood flow velocity change per unit of time, i.e. acceleration of flow. The parameter dF/dt is a measure of the acceleration of blood flow in the aorta and is measured in ml/sec$^2$. It is a parameter that indirectly indicates ventricular contractility. The heart expels the blood with more vigor since with stronger contractions the acceleration of the blood is faster in the aorta. As is observed from the Table in the six control dogs, no significant change in the dF/dt is seen but in the berberine-treated dogs a significant change in dF/dt occurred ($p<0.01$). This can be observed from the last four lines of Table III. The increase in the acceleration of blood flow was in the order of 65% (comparison of first and last columns).

Table IV shows the data obtained on the heart rate (HR) expressed in beats/minutes. In the control group (next to last set of two lines), no significant change in the heart rate occurred; in the berberine-treated group the change was significant. The data shows a reduction in HR of 9 beats/min. This decrease in HR is important since if the increase in contractility were due to adrenergic stimuli, heart rate would have increased (thus it is neither a compound that acts like a catecholamine nor it acts by releasing catecholamine or increasing their concentration in blood or myocardial tissue by other means). Moreover, heart rate, per se, does influence dP/dt. Increases in HR augment dP/dt while fall in HR reduces dP/dt. Thus, normally a decrease in HR is associated with a decrease in dP/dt. The marked increase in dP/dt of the compounds tested accompanied with fall (rather than increase) in HR demonstrated again the potency of berberine.

Table V shows the mean left atrial pressure (LAP). The initial blood pressure was low (i.e. normal) averaging 1 or 2 mmHg, which is as expected in good preparations of non-failing hearts. Under these circumstances no significant change can be expected and there was no change in LAP.

Table VI shows the analysis of the left ventricular end diastolic pressure (LVEDP). LVEDP was normal, averaging 3 mmHg, which is as expected in good preparations without heart failure and similarly to mean left atrial pressure (Table V), it was not expected to change. Indeed no change was shown in that parameter.

In Tables V and VI, no paired t-test analysis was done since it would have been redundant.

Table VII shows an analysis of the aortic systolic pressure. As described above, it was maintained at constant rate. Therefore this parameter showed no change.

Table VIII is a record of the diastolic aortic pressure (DAP). In the control group, diastolic pressure did not change (84 mmHg and 82 mmHg). In the berberine-treated group, the DAP fell from 84 to 62 mmHg. This drop of 20 mmHg is statistically significant. It shows that there was a peripheral vasodilatation.

The change in diastolic pressure in the non-failing heart contrasts with the effect of digitalis type cardiac glycosides which in the non-failing heart produce vasoconstriction or increase systemic vascular resistance. As shown in the above data, as a result of this vasodilation, an influx of blood from the reservoir to the dogs took place.

In 11 dogs at the end of the above-mentioned 90 minute experiments, ouabain 0.03 mg/Kg was given intravenously in a bolus (Table IX). As shown in Table IX, the administration of ouabain did not change significantly diastolic aortic pressure but decreased significantly the flow in the descending aorta by 15% from $1195 \pm 89$ to $1018 \pm 93$ ml/min ($P < 0.01$). Thus, the calculated peripheral resistance increased by 18% ($P < 0.02$). This shows that contrary to berberine which acted favorably reducing peripheral resistance and increasing aortic blood flow, digitalis increased peripheral resistance and reduced aortic blood flow.

Both vasodilation and increase in contractility improve cardiac performance. The former by decreasing peripheral resistance and therefore afterload, and the latter by increasing contractility. The action of both will, therefore, augment cardiac output and the delivery of blood to the organs which is the main function of the heart.

Drugs that increase contractility generally increase myocardial oxygen consumption. In addition, tachycardia and increase in afterload increase further oxygen consumption. The increase in contractility does not necessarily increase oxygen consumption if heart size is at the same time reduced significantly (Laplace Law). See Maroko, P. R., Braunwald, E., and Ross, J. Jr.: The metabolic costs of positive inotropic agents. Chapter 33, *Myocardial Infarction*, Corday, E. and Swan, H. J. C., Editors, Baltimore, Williams & Wilkins Publishing Company, 1973, pp. 244-250, which is incorporated here by reference. Since the increase in contractility due to the compounds of the invention was found to be accompanied by a decrease in afterload (i.e. decreased peripheral resistance) and a reduction in heart rate, the effect of the compounds of the invention on oxygen consumption will be more favorable than that of beta adrenergic agonists that increases heart rate or that do not reduce peripheral resistance (as digitalis). This desirable property of the compounds of the invention assumes added importance in patients with ischemic heart disease and specifically in patients with acute myocardial infarction in whom an increase in myocardial oxygen requirement may be extremely deleterious if not fatal.

To verify this additional advantageous therapeutic property, in pilot experiments, it was shown that when consecutive occlusions were compared, berberine (0.2 mg/kg/min) caused less myocardial injury (as reflected by epicardial ST segment elevations) than a control occlusion and much less than when isoproterenol was infused during an infusion. These changes were due to lower myocardial oxygen consumption during the occlusion with berberine treatment. In addition, the infusion of berberine in dogs without coronary artery occlusion resulted in a reduction in myocardial oxygen consumption despite the increase in contractility (dP/dt). This is quite an advantageous therapeutic combination of properties which further distinguish the compounds of the invention from the conventional drugs.

Likewise coreximine, tetrahydropalmatine and berberrubine administration to dogs (in varying dosages) will be observed to result in a reduction on myocardial oxygen consumption and less myocardial injury than the control. Other species of the preferred groups described above show similar behavior and therapeutic effect.

Table X shows hemodynamic change in a dog following repetitive infusions administered over a period of 5 minutes and the interval between the infusions was around 15 minutes. The infusion of this high dose of berberine shows the good therapeutic index of berberine and especially the fact that no arrhythmias occurred, that aortic flow continued to be augmented, that diastolic pressure (i.e. peripheral resistance) continue to be low, that left ventricular dP/dt and aortic dF/dt assessing ventricular contractility continued to be increased and that heart rate decreased. Therefore, these have no reversal of effects (biphasic response) when the drug was given.

This data also indicates that if the blood pressure would not have been maintained constant by blood infusion, there would have been a decrease in arterial systemic pressure. Therefore, the peripheral vasodilation can be appreciated by the fall of the diastolic arterial pressure which also is commonly expressed as the widening in the pulse-pressure (PP). PP is the value which is the difference between systolic and diastolic pressures.

It is noteworthy that the berberine-treated dogs did not develop any type of arrhythmias during the experimental period. Specifically the dogs did not exhibit premature ventricular beats or any degree of atrio ventricular blocks. Digitalis and other allied cardiac glycosides are known to stimulate arrhythmias of different types, as has been described above.

This work shows that berberine increases the classical indices of heart contractility such as dP/dt and dF/dt by at least 50% and increased considerably aortic flow. Berberine also reduced the heart rate, another desirable result. In addition, berberine decreased the calculated peripheral resistance. These results indicate that berberine is an important and potent positive inotropic agent and increases cardiac performance by both its positive inotropic effect and vasodilation.

The mechanism of berberine is dissimilar to that of beta-adrenergic agonists, which while increasing contractility, increase heart rate also. While berberine is similar from this point of view to digitalis type cardiac glycosides, it differs from digitalis for instance, since it does not provoke arrhythmias, a most undesirable toxic effect of digitalis. Berberine differs also from digitalis because it reduces peripheral resistance in the non-failing heart.

Table X shows the results of the administration of 0.7 mg/kg/min up to a dose of 56 mg/Kg, in one dog. It is noted that the dP/dt increased by 350% after the eighth dose and dF/dt by 450%. No arrhythmias were observed. This data confirmed by other data, suggests that berberine has an excellent therapeutic index, in contrast to digitalis.

When the corresponding experiments are run using coreximine like results are obtained. There is an increase in dP/dt, peak blood blow, acceleration of blood flow and a decrease in the heart rate and diastolic pressure.

Equivalent results are obtained when tetrahydropalmatine is used.

When berberubine is used in the preceeding experiments like results are obtained.

Likewise, typical compounds which come within the generic formula of the compounds of the invention as disclosed above, produce like therapeutic effects in the preceeding experiments.

The compounds of the invention have, as has been shown above, positive inotropic effects and an improved performance by increasing aortic blood flow. Furthermore, it was shown that they produce a distinct systemic prolonged and continuous arterial hypotension. This hypotensive effect is due to peripheral vasodilation and obviously not to a negative inotropic effect. Compounds of the invention are therefore of significant utility.

In the treatment of heart failure, the reduction in afterload is an important and frequently used therapy in the treatment of patients with heart failure. Afterload has been defined, when applied to the intact ventricle, as the tension, force, or stress (force per unit cross-sectional area) in the ventricular wall, after the onset of shortening, and it is a key determinant of the quantity of blood ejected by the ventricle. The two main parameters that change afterload in accordance with Laplace's Law are left ventricular wall tension and arterial pressure, the former being a function of its diameter, wall width and shape. See Braunwald, page 438-439.

The following tables report the experiments showing the effects of the berberine on systemic arterial pressure, when this parameter is permitted to vary.

Table XI shows systolic pressure; and
Table XII shows diastolic pressure.

The protocol was the same as described above except that in these dogs, contrary to the previously reported series, the systolic arterial pressure was not maintained constant. Also, the dogs were instrumented only with an electrocardiogram (with lead aVF being constantly recorded), and polyethylene cannula in aorta introduced through the carotid artery to measure aortic pressures, and another cannula in the jugular vein for drug administration. Average heart rate (measured by continuously monitored electrocardiographic lead aVF) was reduced from $146\pm4$ (mean$\pm1$ S.E.M.) to $132\pm7$ mmHg ($p<0.1$) after the first 45 minutes. After the second 45 minutes heart beat rate was further reduced to $124\pm6$ mmHg ($p<0.01$).

Mean systemic arterial pressure fell significantly from $114\pm7$ mmHg to $87\pm5$ mmHg ($p<0.005$) at 5 minutes to return to and stabilize in the 90's and 100's. It was after 10, 15, 30 and 45 minutes, respectively, $93\pm4$, $92\pm5$, $101\pm7$ and $101\pm7$ mmHg. After the second dose, the pressure fell significantly to $94\pm4$ ($p<0.025$) mmHg at 5 minutes, to stabilize thereafter in the mid 90's. It was respectively at 10, 15, 30 and 45 minutes $95\pm6$, $95\pm5$, $97\pm5$ and $97\pm5$ mmHg, respectively. Thus after 90 minutes the mean pressure fell significantly from $114\pm7$ to $96\pm5$ mmHg ($p<0.025$).

In Table XI, the systolic and in Table XII, the diastolic pressure respectively changed in the same direction to the mean arterial pressure. The most marked decrease was in the diastolic pressure. The pulse pressure (systolic minus diastolic pressure) increased from an average of 28 before berberine administration to 35 mmHg at the end of the experiment. This increase in pulse pressure is attributable to the reduction in peripheral resistance and/or increase in contractility.

These experiments show the beneficial effect of repeated dose of berberine given intravenously on systemic arterial pressure and heart rate. In the experiments described earlier (Tables I-X) the arterial pressure was maintained constant in order to verify the effect of berberine on dP/dt. The present data (Tables XI-XII) show that in addition to the positive inotropic effects (increase in dP/dt and dF/dt) that aortic pressure (mean, systolic and diastolic) were reduced when blood pressure was not maintained constant. This hypotensive effect was accompanied by another favorable effect which is a reduction in heart rate.

In 4 groups of dogs instrumented as in the last series of experiments (Protocol RK) the effects of increasing dose response on systemic arterial pressure was examined. The only difference from that protocol was that only one dose of berberine (as opposed to two) was administered.

The effects on the measured parameters is dose responsive. In four groups of dogs, the changes in blood pressure were analyzed. The dosage administered was 7.5, 15, 30 and 70 mg/Kg. It was observed that generally blood pressure drop was most marked in the first 5 minutes. After 90 minutes following the injection (when the experiment was discontinued), the average fall in mean arterial pressure in the group which received 15 mg/Kg was 19 mmHg; in the group that received 30 mg/Kg it was 37 mmHg and in the group that received 70 mg/Kg it was 63 mmHg. This shows the gradual response with increase of dosage of the drug. No primary arrhythmias were observed in the dogs over the time and dosage administered.

Heart rate was also dose-dependent decreasing after administration of 7.5, 15, 35 and 70 mg/Kg off berberine by 20, 16, 40 and 103 beats/min., respectively.

In conclusion, it was demonstrated that both changes, that is, decrease in heart rate and blood pressure, are proportional to the dose of berberine administered.

In one dog using protocol M simile, 240 mg/Kg of berberine HCl was administered and dP/dt increased by 75%, aortic flow by 67%, heart rate fell from 150 to 114 beats/min., diastolic aortic pressure fell from 92 to 67 mmHg, and left atrial pressure fell from 8.5 to 7.5 mmHg. No arrhythmias were noted, even at that higher concentration. This data shows that higher doses of berberine also favorably affect the dP/dt and aortic blood flow and other characteristics without induction of arrhythmia. This shows the good therapeutic index of this compound and shows the lack of biphasic response of LV dP/dt.

When this type of experiment was repeated with tetrahydropalmatine, a first dose of 3.5 mg/Kg was given without maintaining the pressure constant and arterial pressure fell from 142/115 to 118/90 mmHg. When the second infusion was given with constant pressure, dP/dt increased by 17%.

Tetrahydropalmatine has, like other compounds of the invention a favorable effect on the contractility of the heart and on aortic blood flow.

Likewise comparable results are obtained when the experiments are repeated using coreximine.

Similar values are obtained when berberine, representative compounds which come within the generic formula groups listed herein and disclosed above produce like beneficial therapeutic effect.

Berberine is well tolerated and no noteworthy side effects were noted in the various experiments done in dogs. The $LD_{50}$ for rats when injected intravenously in a bolus was about 55 mg/Kg. In cats the $LD_{50}$ was about 55 mg/Kg. It is noted though that higher dosages are administerable depending on the method (and speed) of administration and the particular species of the compounds of the invention some of which have even or expected to have even a lower $LD_{50}$. It is also known that certain animals, like the equine species or swine species will tolerate higher dosages without undue adverse effects.

To examine the effect of varying doses of protoberberine on the hemodynamic parameters, the following protocol (Protocol Z) was carried out:

Mongrel dogs weighing between 15 and 25 kg were anesthetized with intravenous sodium thiamylal (20 mg/kg initially with additional doses given as needed). The dogs were intubated endotracheally, and respiration was maintained by a Harvard respirator. The chest was then opened in the fourth left intercostal space and the heart suspended temporarily in a pericardial cradle.

Aortic pressures were recorded through a polyethylene cannula introduced through the carotid artery (Statham P23 Db pressure transducer) and electrocardiogram (lead aVF) were recorded throughout the experiment on a polygraph (Gould Instruments). Another polyethylene cannula was placed in the left atrium for measurement of atrial pressure (Statham P23 Db pressure transducer). An electromagnetic flowmeter (Biotonix Laboratories) was placed around the ascending aorta and the aortic flow was recorded on a polygraph. Two catheters were inserted into the left ventricle through a femoral artery.

The first ("pigtail") served as a reference, while the second (Millar microtip transducer catheter) was connected through a Millar transducer (Millar Instruments, Houston, Tex.) to the polygraph, where both left ventricular pressure curves were recorded simultaneously. The left ventricular end diastolic pressure was recorded separately through a Millar catheter. The first derivative of the left ventricular pressure (dP/dt) was obtained by electronic differentiation of the left ventricular pulse recorded through the Millar catheter.

A reservoir of blood was connected with the femoral artery in order to maintain constant left ventricular pressure during the experiment. In this protocol, similarly to protocol M, systemic arterial pressure was maintained constant in order to have accurate measurements of dP/dt which represent well left ventricular contractility when the systolic pressure is maintained constant. However, calculated total peripheral resistance will be higher (an underestimation of the fall). After stabilization of hemodynamics as reflected by continuously monitored parameters for 15 minutes, the substances to be studies were infused intravenously using a Harvard infusion pump. Registrations were made every 5 minutes at a paper speed of 200 mm/second, while all the parameters were recorded constantly at a speed of 2 mm/second. The dogs were randomly assigned to several groups:

Group (a) Control—in these dogs a solution of 5% dextrose in water was infused in the same quantity as in the berberine treated animals (n=7).

In all berberine, berberrubine coreximine and tetrahydropalmatine groups the compounds were infused at constant rate for 35 minutes and the data analyzed at 5 minute intervals.

Group (b) Berberine 0.7 mg/Kg/min (n=10).
Group (c) Berberine 0.2 mg/Kg/min (n=7).
Group (d) Berberine 0.02 mg/Kg/min (n=7).
Group (e) Berberrubine 0.2 mg/Kg/min (n=7).
Group (f) Tetrahydropalmatine 0.2 mg/Kg/min (n=4).
Group (g( Coreximine 0.2 mg/Kg/min (n=8).

Therefore, group B, c and d were used to analyze the various effects of continuous infusion of berberine and its dose response and groups e and f and g used to examine the effects of these three other protoberberines. Moreover, their effects were compared to the berberine treated dogs with the same dose (i.e. Group c).

FIGS. I, II, III and IV show that left ventricular maximal dP/dt, aortic pulse pressure, aortic blood flow and heart rate did not change significantly in the control dogs (group a).

The effect of the infusion of 0.7 mg/Kg/min of berberine (group b) is shown in comparison to control (group a) as well in comparison to dogs that received 0.2 (group c) and 0.02 (group d) mg/Kg/min in the same figures (I-IV). These findings will be discussed below.

FIG. V, however, summarizes specifically the effects of the infusion of berberine 0.7 mg/Kg/min during the 35 minute period of the experiments. The data are presented as a percent change from before infusion. It shows that berberine infusion resulted in an increase in LV dp/dt of 35% after 5 minutes and that thereafter the increments in LV dP/dt were smaller being the increase at 35 minutes of $43.2\pm7.0\%$ ($P<0.001$). Thus, it seems that when a continuous infusion of 0.7 mg/Kg/min is given, the dose in the first 5 minutes is responsible for most of the increase and thereafter it reaches nearly a plateau. The plateau may be due to the progressive fall in heart rate; otherwise, it may be expected that dP/dt would have increased further. The aortic pulse-pressure (i.e. systolic minus diastolic pressures) widened (i.e. increased) progressively throughout the experiment and is directly and linearly proportional to time (and to the dose infused). After 35 minutes it increased significantly by $125\pm19\%$ ($P<0.001$). This remarkable increase in pulse pressure is due to the fall in the diastolic pressure since the systolic pressure was maintained constant. Thus, it shows the intense and progressive effect of the compound as an agent reducing afterload and a peripheral vasodilator.

Peak aortic blood flow, measured in the ascending aorta increases progressively and is linearly proportional to time (and total dose injected). After 35 minutes flow increased significantly by 73%. The increase in stroke volume (calculated by planimetry) was of $169\pm36\%$ ($P<0.005$) over the control and the increase in cardiac output was $75\pm29\%$ ($P<0.005$) over the control. Calculated total peripheral resistance after 35 minutes decreased by $468\pm9.3\%$ ($P<0.001$). Thus, it became apparent that berberine (0.7 mg/Kg/min) acted very favorably because it increased contractility and reduced peripheral resistance and consequently augmented markedly the aortic blood flow.

Moreover, heart rate was reduced by $32\pm3\%$ ($P<0.001$). This is, per se, a favorable effect since it renders the heart performance more efficient especially when tachycardia is initially present as in many patients with heart failure. The fall in heart rate decreases myocardial oxygen consumption which benefits the balance of oxygen of the myocardium. It shows also that the increase in contractility is probably even greater than reported here since the fall in heart rate, per se, has a negative inotropic effect in the anesthetized dog. Finally, the fall in heart rate suggests that the effect of berberine is not similar to that of a beat-adrenergic agonist.

All these effects (increase in contractility, decrease in afterload, peripheral vasodilation, increase in aortic blood flow and reduction in heart rate) are beneficial in the treatment of any condition requiring the improvement of performance of the heart and especially if that has to be done with a minimum increase in expenditure of energy (i.e. of oxygen).

As shown in FIG. I, the effects of 0.2 and of 0.02 mg/Kg/min of berberine are also statistically highly significant in increasing contractility (LV dP/dt). When all curves (group b, c, and d) are analyzed together there is a clear dose response with dP/dt increasing proportionally and linearly to dose given. With the higher there is a tendency to reach a plateau when the increase reaches 40%. It is very important to note that even the low dose of 0.02 mg/Kg/min resulted in a highly significant increase in dP/dt which was $35.8\pm8.2\%$ ($P<0.0005$) after 35 minutes. This also shows again the very good therapeutic ratio. In one additional dog, berberine was infused in even a small concentration of 0.002 mg/Kg/min and dP/dt increased by 20%.

The increase in pulse-pressure indicates the fall in diastolic aortic pressure which signify peripheral vasodilation and afterload reduction. The dose response here is also evident and again even the infusion of 0.02 mg/Kg/min (group d) increased pulse pressure by $18.5\pm10\%$.

The increase in stroke volume was also dose dependent. Again, this reflection of better cardiac performance was elicited even with the dose of 0.2 mg/Kg/min (group c) increasing significantly aortic flow by $53.6\pm17.7\%$ ($p<0.01$).

Finally, the fall in heart rate was also dose dependent. However, at the smaller doses there was no significant fall in heart rate.

From these experiments it can be concluded that berberine acts very favorably on the measured hemodynamic parameters with the view of its application in patients in whom heart performance should be improved such as chronic congestive heart failure, acute heart failure in all its types of manifestations such as cardiogenic shock and pulmonary edema, in low cardiac output syndromes and in non-cardiogenic shock syndromes or diseases in which it is clinically advantageous to augment cardiac output, increase cardiac contractility especially when this property and peripheral vasodilation may be sought after such as in shocks of non-cardiogenic origin.

Moreover, it shows that the effect of berberine on the different favorable parameters occurs at different doses and is differently dose related. Thus, the fall in heart rate occurs later (i.e. in the higher dose) than increases in LV dP/dt, increases in aortic flow or fall in aortic diastolic pressure. Also the fall in peripheral resistance, the increase in pulse-pressure and the increase in aortic flow continue to change even in the highest doses that were given in these experiments while LV dP/dt at the higher doses but not in the smaller doses tends to reach a plateau. Thus, it may be possible to tailor the amount of berberine to the specific condition of the patient. The same is done with coreximine, tetrahydropalmatine and berberubine. Likewise with other representative species of the compounds of the invention, like "tailoring" is attractive therapeutically.

The comparison of berberine, berberrubine, tetrahydropalmatine and coreximine is shown in table XIII, where all were given at a dose of 0.2 mg/Kg/min (group c, e, f and g). The results show that berberine, and berberrubine, tetrahydropalmatine and coreximine all increased the dP/dt values in similar magnitude (from 32 to 44%). Berberine did increase it mildly more than the others. The fall in diastolic arterial pressure (as reflected by widening in the pulse-pressure ("PP") was shown in all drugs. It was noted to be more than twice as large with berberine than with the other three drugs. Heart rate ("HR") dropped with all compounds; it fell approximately 16-17% with berberine, berberrubine and coreximine and by 5.5% with tetrahydropalmatine. Stroke volume ("SV") increased significantly with berberine, tetrahydropalmatine and coreximine; just slightly (and not statistically significantly) with berberrubine. With a larger dosage of 0.5 and 0.7 mg/Kg/min., stroke volume increase will be noticeable with berberrubine.

Consequently, calculated peripheral resistance was reduced significantly by over 30% with berberine and tetrahydropalmatine, while coreximine and berberine did not show that property to that pronounced degree.

Thus, when it is desired to maximize increase in contractility without vasodilation, the compounds of choice are coreximine and berberrubine, whereas berberine and tetrahydropalmatine are the compounds of choice when vasodilation and contractility both are desired concurrently.

This analysis shows that in all of the measured parameters the changes were directionally the same, though of different magnitude. Thus, for example tetrahydropalmatine is a compound of choice when decrease in heart rate is not as necessary; berberrubine and coreximine will be compounds of choice when lesser effect on pulse pressure is desired.

Traditional drugs for the treatment of acute heart failure such as the cathecholamines and other sympathomemetic amines which are known to exert a positive inotropic effect by interacting with myocardial (beta 1) adrenergic receptors such as dopamine, dobutamine or isoproterenol are traditionally administered not only in cradiogenic shock but in "low output syndrome" situations such as by infusion during and after cardiac surgery. Braunwald, pages 553/557.

To determine further the effects of berberine on patients, experiments were carried out on conscious dogs (Protocol F) and the measurement of left ventricular performance was assessed atraumatically using the multiple gated radionuclide ventriculography (MUGR) similarly to what is done in patients. The multiple gated radionuclide ventriculography is used in patients to assess their cardiac (i.e. left ventricular) performance by analyzing in an atraumatic manner, the ejection fraction (EF) of the left ventricle. This technique substituted the analysis of ejection fraction by contrast angiography since the latter can be done only in the catheterization laboratory with the patient submitted to the introduction of catheters into his arteries and left ventricular cavity as well as an injection of a radio-opaque dye. MUGR consists in using red blood cells labelled with stannous radioactive technetium. These red blood cells can be labelled either in vivo or in vitro prior to injection. The blood that is now emitting gamma radiation can be detected by an external gamma camera. This device can sum many cycles of the heart beat obtaining an average cycle. Then this cycle is divided in time intervals so that, as an example, the end systolic and end diastolic frames can be identified.

Ejection fraction is the end distolic minus the end systolic volumes divided by the end diastolic volume. It indicates therefore the pumping effectiveness of the left ventricle since it measures the fraction (or the percent if multiplied by 100) of the volume of blood that is expelled from the left ventricular cavity.

Experiments were carried out in trained conscious dogs. 40 mCi of pertechnatate were used to label red blood cells that were then injected intravenously. MUGR was done during infusion of placebo (5% dextrose in water) and during berberine intravenous infusion (0.7 mg/Kg/min during 5 minutes). The images were acquired using fixed density of the left ventricle. They were measured in quadruplicate and averaged. The external gamma camera used was Ohio Nuclear (model VIP 560).

Table XIV is an example of one such dog. The ejection fraction (EF) was 31.5, before any treatment. After the 5, 15, 30 and 45 minutes of infusion of dextrose (in control) it was 39, 34, 34 and 28%, respectively. Thus, before the infusion of berberine it averaged 33±2%. After the infusion of 0.7 mg/Kg/min of berberine for 5 minutes, the EF was 46, 47, 44 and 38%, respectively; averaging, therefore, 44±2%. This increase was statistically significant ($p<0.01$). It was an increase by 33% versus the pre-berberine period. A second infusion of the same dose of berberine resulted in EF of 46, 37, 40 and 38%, being on the average 40±2% which is also different from the pre-berberine period ($p<0.05$).

Another example is shown graphically (FIG. VI). This dog received an infusion of 5% dextrose in water for 15 minutes during which time the ejection fraction was stable around 50%. Thereafter, an infusion of berberine 0.7 mg/Kg/min was started and continued for the next 15 minutes. The ejection fraction increased continuously from 50 to 54 to 65 and finally to 70% after 15 minutes; i.e. an increase of 40%.

These two dogs are excellent examples of the potency of berberine that increased ejection fraction in these 2 dogs by 33% and by 40%, respectively. These increases are remarkable under any circumstance but more so since they were obtained (a) in the conscious dog and therefore with its reflexes intact and without any possible cardiodepressant effect of anesthesia and (b) because they were obtained in a dog without failing heart. In the non-failing heart situation, here shown, a drug has to be much more potent in order to increase ejection fraction than in a situation of heart failure.

Nevertheless, to verify the response of dogs with acute heart failure with this sophisticated technique, this condition was provoked by previous embolization into the left coronary artery (as described below in protocol HV). Thereafter, the effect of berberine infusion was analyzed after embolization. Thus, in one dog before embolization (i.e. before acute left ventricular failure) EF was 47%. After embolization and before berberine administration EF fell to 27%. Berberine was infused in a rate of 0.2 mg/Kg/min for 30 minutes and MUGR was repeated after 2, 15, 22 and 28 minutes of infusion. EF improved clearly from 27% to 35, 37, 39 and 38% respectively. In another dog EF before embolization was 55% after emboilization it fell to 39%. The administration of berberine 0.2 mg/Kg/min restored EF to 60, 62, 55, 55% at 2, 15, 20 and 30 respectively.

Six dogs were studied using this technique (Table XV). Their average left ventricular ejection fraction (EF) fell from 55±% to 27±%2 ($p<0.001$) after embolization showing that they had now left ventricuar failure. The thirty minute infusion of berberine (0.2 mg/kg/min) was administered. During this period four radionuclide ventriculographies were obtained and averaged. After discontinuation of the infusion again four radionuclide ventriculographies were obtained in the next thirty minutes and averaged. Berberine infusion significantly increased EF in the dogs with acute left ventricular failure from 27±3% to 40±3% ($p<0.001$). This increase of nearly 50% showed a very potent effect of this drug. After the discontinuation of berberine infusion EF fell somewhat but continued to be significantly elevated for the next half an hour when the experiment was terminated.

These results demonstrate the highly significant improvement both biologically and statistically of the heart failure by the administration of berberine in a conscious dog.

When these experiments are repeated with other representative series of the invention, like improvements on EF are observed. With tetrahydropalmatine, coreximine and berberrubine like results will be observed.

This date (together with other reported and developed data) supports the conclusion that berberine is useful in congestive heart failure since EF is a sophisticated and commonly used clinical parameter to evaluate performance of the heart which is the main goal of treatment of patients with heart failure. The increase in EF, which was done without heart failure, strongly suggests the effect to be even more marked with patients with heart failure. Finally, the experiments with acute left ventricular failure confirm its usefulness.

It has been further discovered that berberine is an ideal agent for scanning the heart. This is performed in a known manner by attaching a gamma ray-emitting marker such as iodine, bromine or technitium to berberine. In that respect, berberine has the advantages of such known scanning agents such as thallium (or potassium analogs) commonly used today.

It is known in the field of cardiac examination that to obtain a scan of a cardiac silhouette after intravenous injection of a radioisotope (such as in this case the gamma ray-emitting marked berberine), the area of the cardiac silhouette occupied by the labelled intracardiac blood pool is comparable with the cardiac silhouette on the chest roentgenogram (the difference being the wall thickness). This property can be used for the detection of the pericardial infusion in which case the X-ray films will show a much wider silhouette. The intravenous injection of a small bolus of a gamma emitter such as 99mTc pertechnetate permits rapid visualization of the heart, great vessels and other vessels by an angiocintillation camera. This technique is used in a variety of acquired or congenital cardiac lesions. Such radioisotopes are used for myocardial imaging. Typical radioactive substances as 43K (potassium), 81Rb (rubidium) or 201Tl (thallium) concentrate in normal myocardium. Such myocardial imaging is known and is described for instance in Harrison's, Chapter 234, pages. 1153 and seq. which is incorporated herein by reference.

This property of berberine differentiates it and is another advantage over digitalis since digitalis is not a suitable marker for the heart but rather for the liver.

Preferential concentration of berberine in the heart rather than in other thoracic organs or the liver is a sine qua non for a good imaging agent. Berberine level measurements were done spectrophotometrically. The experiment consisted of injecting 3.5 mg/Kg of berberine (SO4) intravenously and killing the rats after 15 minutes, 90 minutes, 6 hours, 24 hours, 48 hours and 1 week. Each group consisted of 5-6 rats. A control group (no berberine administration) was used to determine the absorbance of the different organs at that wave length. The data showed that the concentration in the tissue of rat heart was 16±2, 19±3 and 13±3 ug/g of berberine at 15 min, 90 min and 6 hours respectively, falling to zero thereafter. It was released rapidly from the heart thus showing no significant tendency to accumulate in that organ. Its concentrate was 1, 1 and 3 ug/g on the lungs and 0.2 and 0 in the skeletal muscles or in the blood at the same time intervals. Also in the liver it was 0, 6, and 2 ug/g showing an excellent ratio of concentration between the heart and each one of the above-mentioned tissues.

To verify the effects of berberine in the situation of an acute left ventricular failure (Protocol HV) the following was carried out.

Experiments were carried out in 21 mongrel dogs of either sex with body weight between 19 and 39 kg. Anesthesia was induced with sodium pentobarital, 25 mg/kg of body weight intravenously, and small supplementary doses were given as necessary to maintain a constant level of anesthesia. The dogs were placed in the left lateral position and ventilation was maintained through a cuffed endotracheal tube with a volume-controlled respirator (Harvard Apparatus Co., Millis, Mass.). Polyethylene cannulae were placed into the jugular and femoral veins for intravenous infusions and drug administration. Electrocardiograms (lead aVF) were monitored continuously throughout the experiments.

A polyethylene cannula was introduced into the aorta through the left carotid artery to record arterial pressure. (Statham P23 ID transducer, Statham Instruments, Inc. Oxnard, Calif.). A miller microtip transducer catheter (Millar Instruments, Inc., Houston, Tex.) was introduced into the left ventricular cavity through the femoral artery to measure left ventricular pressures. For adjustment of zero level, left ventricular pressure was also measured through the fluid-filled lumen in the Millar catheter (Statham P23 ID transducer). The maximal rate of rise of left ventricular pressure, LV dP/dt, was recorded by means of a differentiator. All these parameters were recorded continuously on a polygraph (Gould 2800, Gould Instruments, Cleveland, Ohio). Cardiac output was determined by the thermodilution technique, using a thermistor catheter in the pulmonary artery and calculated by a cardiac output computer (Elecath, Electro-catheter Corp., Rahway, N.J.). The coefficient of variation for duplicate CO measurements was 5%. In addition to the parameters directly obtained, total peripheral vascular resistance was calculated from the ratio of aortic diastolic pressure and cardiac output. Stroke volume was calculated by dividing cardiac output by heart rate. Heparin (Invendex) (5000 IU) was administered to avoid clotting of the catheters.

To induce acute left ventricular failure, initially the left main coronary artery was catheterized with a Judkin coronary artery catheter (7F, ISCI Cardiology and Radiology Products, Billerica, Mass.) under fluoroscopic control. It was introduced through a femoral artery, and polystyrene microspheres (3M Company, St. Paul, Minn.) with a diameter of 52. 5±4.0 um (mean±SD) were injected into the cornary artery. The microspheres were used in a concentration of 1 mg (i.e., 12,000) per ml saline. The first dose of microsphere solution was 0.5 ml/kg body weight, and all subsequent doses were 0.25 ml/kg body weight, administered every 5 minutes. Administration of microspheres was discontinued when LV dP/dt had been reduced by 30% or more when measured 4 minutes after the last dose. All dogs received prophylactic antiarrhytmic treatment with intravenous lidocaine, 1.5 mg/kg body weight as a bolus 20 min after the end of embolization, followed by a continuous infusion of 45 ug/kg/min.

Forty-five minutes were allowed to elapse to verify the stability of the preparation. If LV dP/dt or left ventricular end diastolic pressure had changed by 20% or more between 30 and 45 minutes after embolization, the dogs were excluded from this study and not randomized. Forty-five minutes after the end of embolization, the dogs were assigned randomly to three groups: (a) Berberine-treated group, 0.2 mg/kg/min, dissolved in 60 ml of a solution of 5% dextrose in water administered in a constant infusion during 30 minutes; (b) ouabain-treated group, 0.03 mg/kg was administered in 60 ml of a 5% solution of dextrose in water during 30 minutes; and (c) Control group, administration of 60 ml of a 5% solution of dextrose in water during 30 min.

A paired Student t test (two-tailed) was used for statistical analysis of changes in hemodynamic variables within each treatment group, and a Student t test for group observations (two-tailed) was used for statistical analysis of differences between treatment groups. All data are presented as mean ±1 standard error.

The successive injections of microspheres into the left main coronary artery caused a gradual reduction in LV dP/dt and increase in left ventricular end diastolic pressure. The average number of doses used for induction of acute heart failure was 7.7±0.4 which corresponds to about $6.3 \times 10^5$ microspheres. The embolization was terminated when LV dP/dt was reduced by 37±3% from 2988±152 mmHg/sec to 1823±65 mmHg/sec (p<0.01, n=21), left ventricular end diastolic pressure increased by 145±16% from 5.5±0.2 mmHg to 12.5±0.6 mmHg (p<0.001, n=21), means systemic arterial pressure decreased by 15±3% from 126±5 mmHg to 106±4 mmHg (p<0.001, n=21), heart rate decreased by 27±5 beats/min, from 163±5 beats/min to 135±6 beats/min (p<0.001, n=21), cardiac output decreased by 23±2% from 3.24 L/min to 2.41±0.10 L/min (P<0.01, n=21), and total peripheral vascular resistance increased by 15±5% from 3228±153 $dyn.sec.cm^{-5}$ to 3702±270 $dyn.sec.cm^{-5}$ (p<0.01, n=21).

The cornary artery embolization induced ST segment elevation and T wave changes consistent with acute global myocardial ischemic injury. After the end of embolization, LV dP/dt and left ventricular end diastolic pressure did not change significantly and were completely stable in all but three dogs after 30 minutes.

Twenty one dogs were randomly assigned to berberine-treated (n=7), ouabain-treated (n=7), or control (n=7) groups. No significant differences were found for any of the hemodynamic variables among the three randomized groups (Table XVI). The infusion of berberine increased LVdP/dt and reduced left ventricular end diastolic pressure within 2.5 minutes. At the end of the 30-minute infusion, LVdP/dt increased by 28±8% from 1572±80 mmHg to 2012±95 mmHg (p<0.005, Table XVI), and was significantly higher than in the control group (FIG. VII). Left ventricular end diastolic pressure decreased by 38±4% from 13.3±0.8 mmHg to 8.1±0.5 mmHg (p<0.001, Table XVI), and was significantly lower than in the control group (FIG. VIII). Systolic arterial pressure was not significantly changed by berberine (Table XVI). Diastolic and mean arterial pressure were significantly although only slightly reduced by berberine (Table XVI). There was an increase in pulse pressure from 28±2 mmHg to 33±4 mmHg. Heart rate fell by 8 beats/min. (Table XVI). Total peripheral vascular resistance increased in the control group, but in contrast it decreased by 19±2% from 4915±559 dyn.sec.cm$^{-5}$ to 4004±496 dyn.sec.cm$^{-5}$ in the berberine-treated group (Table XVI). Thus it was significantly lower than in the control group (FIG. IX, p<0.05). In the control group, cardiac output and stroke volume fell from 1.77±0.28 liters/min to 1.54±0.24 liters/min and from 12.9±1.82 ml/beat to 11.9±1.7 ml/beat, respectively. In contrast, in the berberine-treated group, cardiac output changed from 1.76±0.15 liters/min to 1.93±0.16 liters/min and stroke volume from 14.6±1.9 ml/min to 17.3±2.7 ml/min. Thus, cardiac output and stroke volume were significantly higher at the end of infusion in the berberine-treated dogs (FIGS. X, XI).

In the control experiments, the left ventricular function curves (see Abnormalities of Circulatory Function) are shifted downwards to the right, indicating further deterioration of left ventricular function. The relationship between changes in left ventricular end diastolic pressure and changes in cardiac output and stroke volume from before to 30 min after the start of berberine infusion are shown in FIGS. XII and XIII in the form of ventricular function diagrams. In contrast to the control group, during berberine infusion left ventricular end diastolic pressure is reduced simultaneously with an increase in both cardiac output and stroke volume, shifting the curves upwards and to the left, indicating improvement in ventricular function.

Protocol HV was performed in accordance with that published in Smiseth, Mjos and Refsum,: Hemodynamic effects of the B-adrenergic Receptor Agonist Pirbuterol during Acute Ischemic Left Ventricular Failure in Dogs. *Acta Pharmacol. Toxicol. Scand.* (Suppl. IV) pg. 53, 1981.

Ouabain did not change any of the hemodynamic parameters from before to 30 minutes after the start of drug administration (Table XV).

FIGURE LEGENDS

FIG. VII. Changes in Left Ventricular dP/dt (LVdP/dt). Comparison between berberine control groups. (**=p<0.01 for comparison between the groups).

FIG. VIII. Changes in Left Ventricular End Diastolic Pressure (LV EDP) by berberine Hcl. (**=p<0.01 for comparison between the groups).

FIG. IX. Changes in Total Peripheral Vascular Resistance (TPR). (**=p<0.05 for comparison between the groups).

Figure 4:
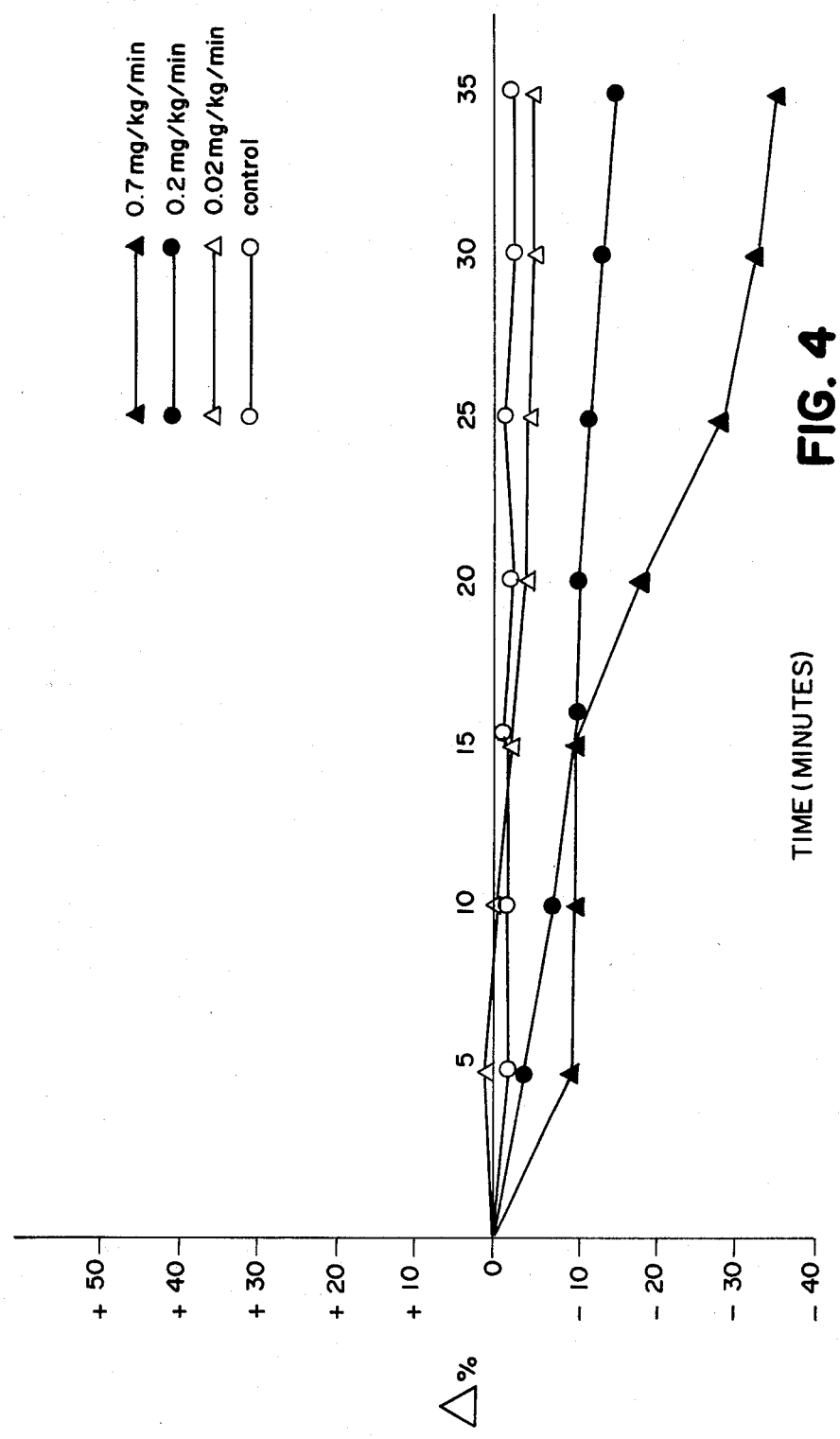
Figure 5:
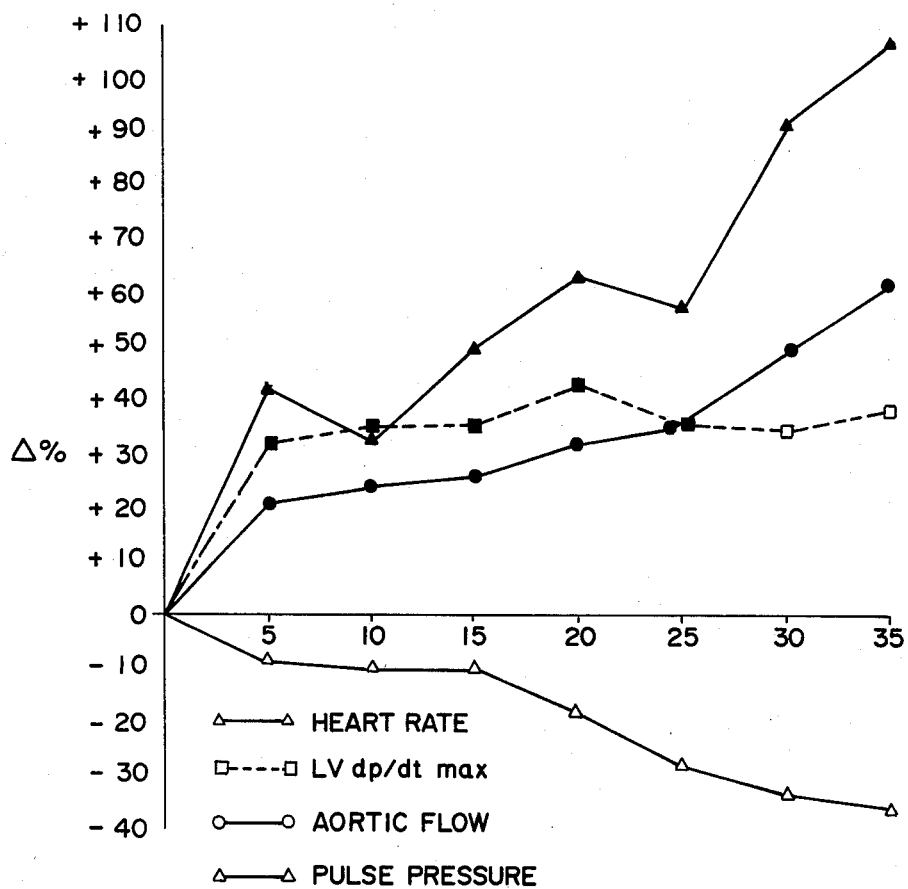
Figure 6:
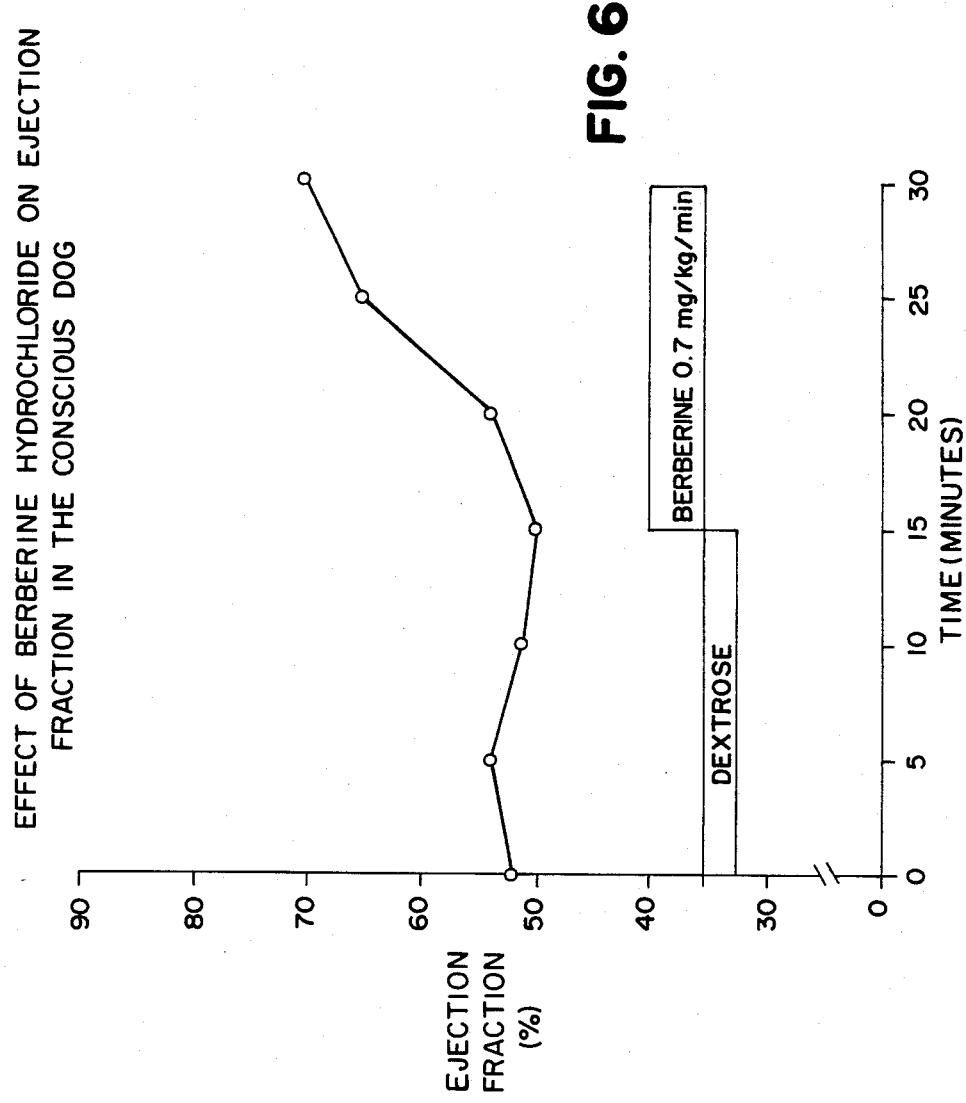
Figure 7:
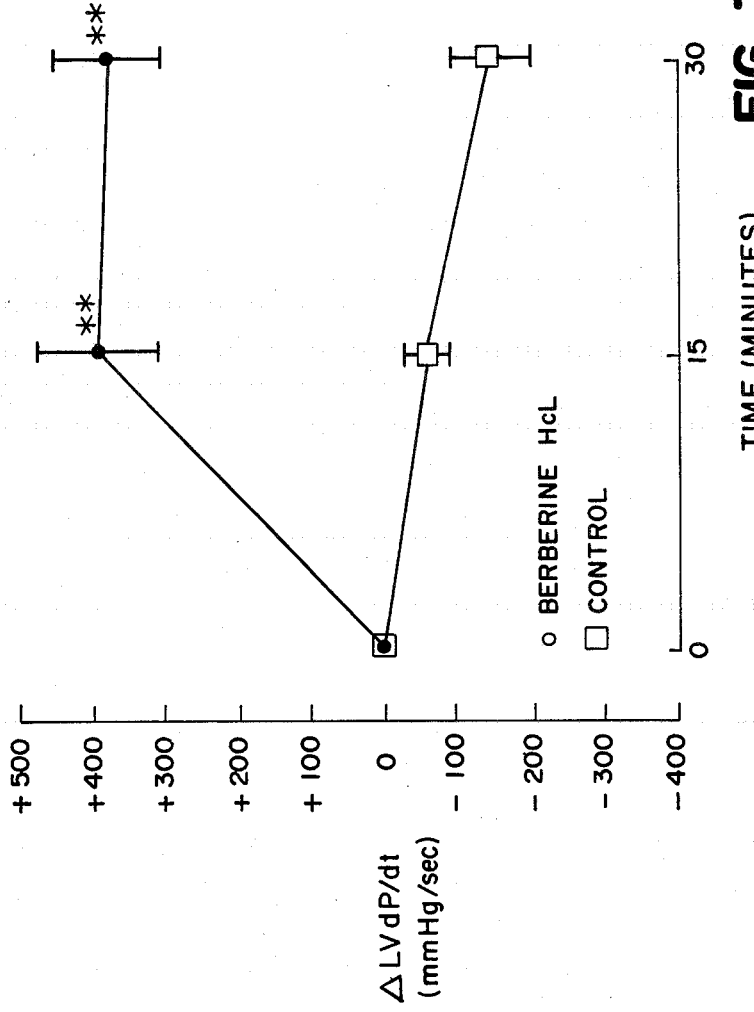
Figure 8:
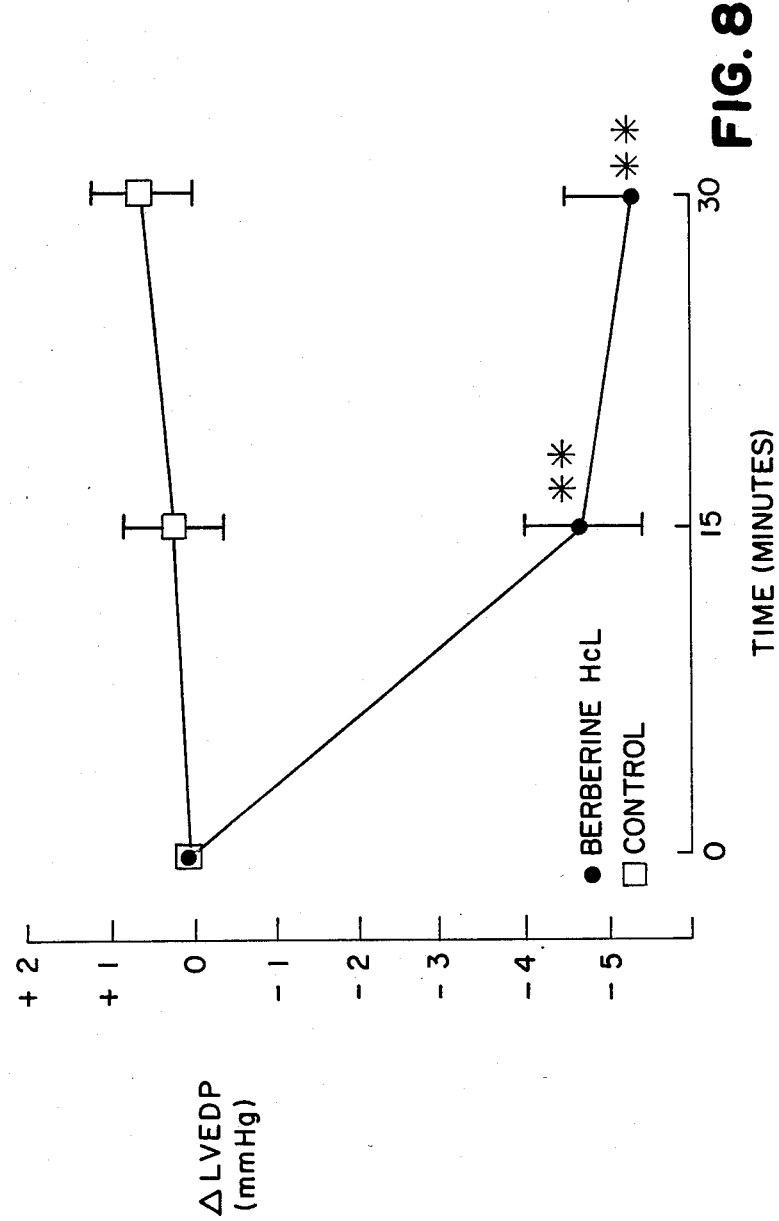
Figure 9:
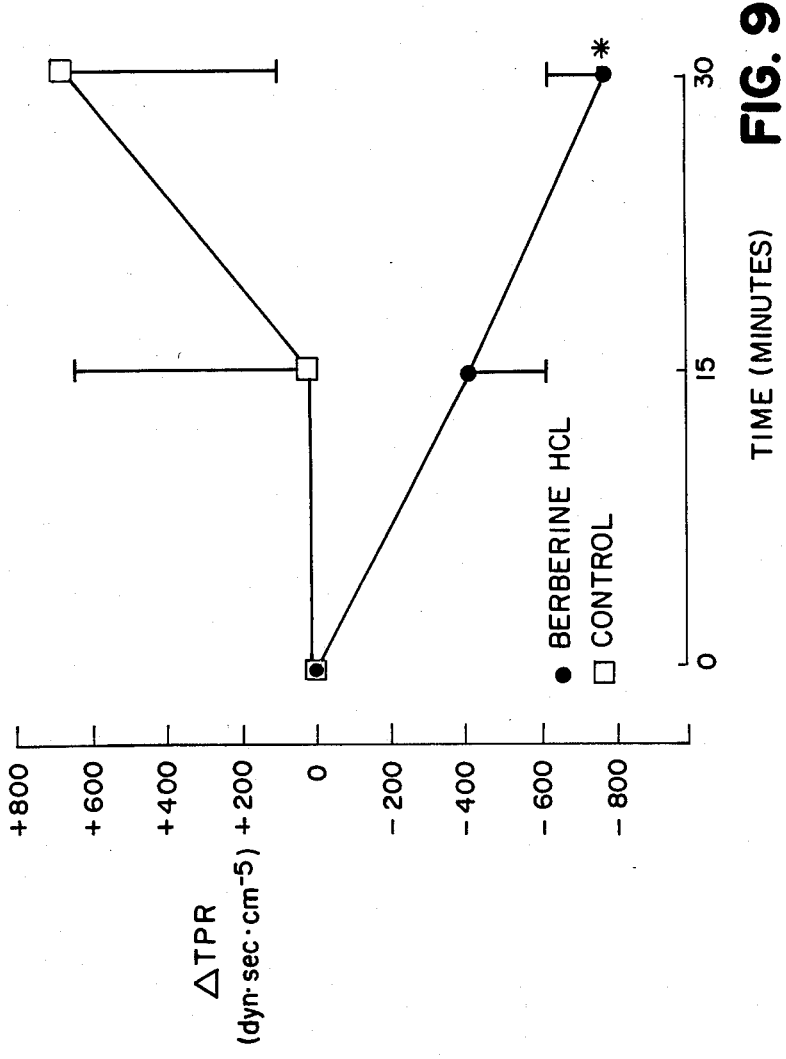
Figure 10:
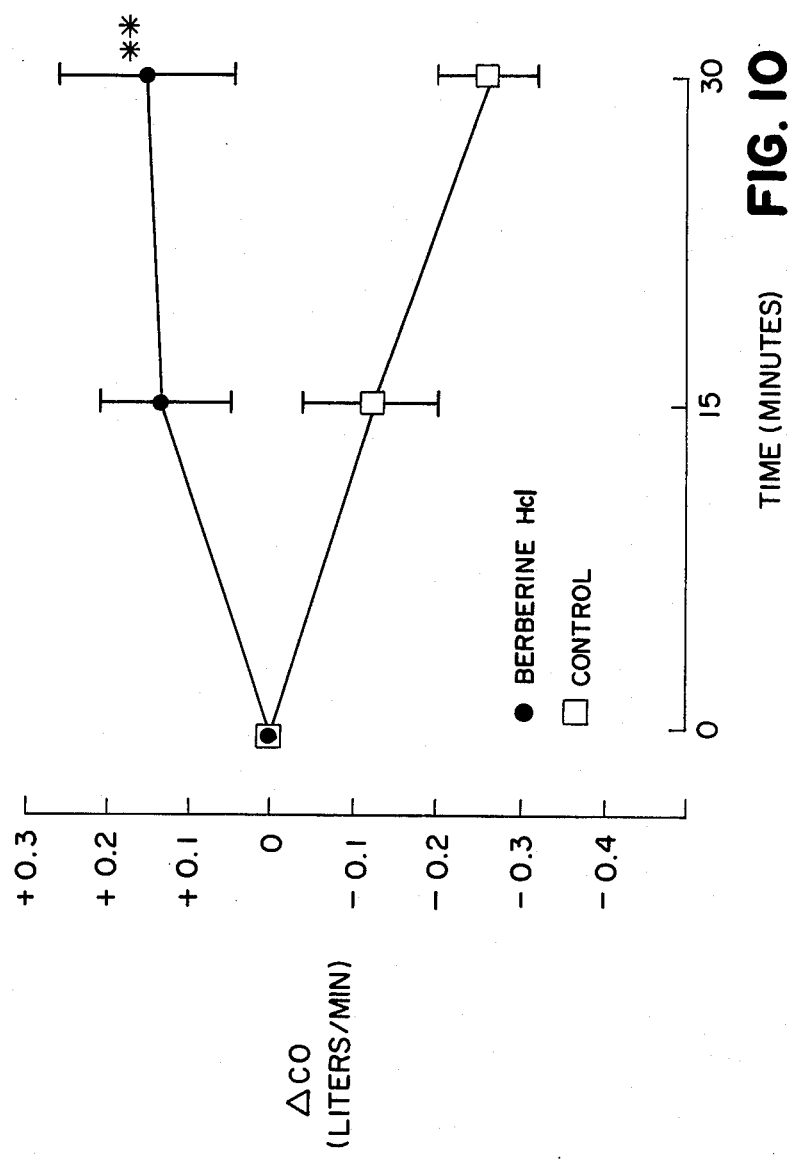
Figure 11:
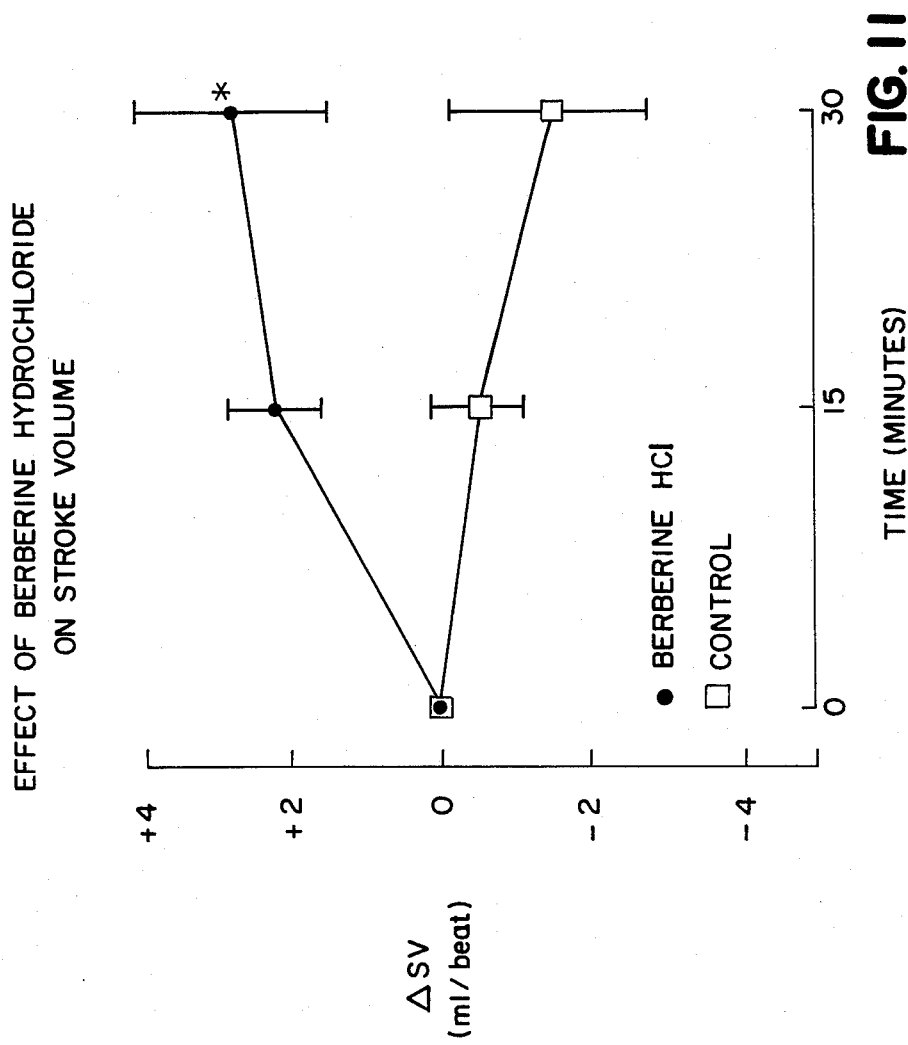
Figure 12:
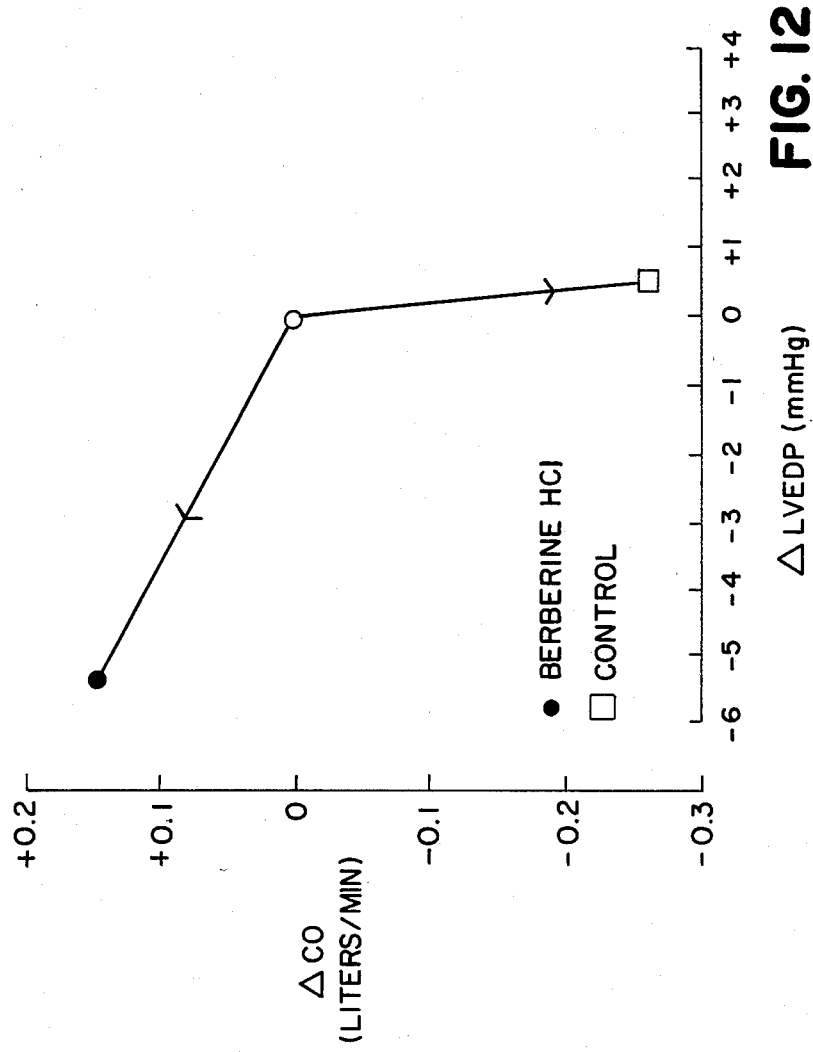
Figure 13:
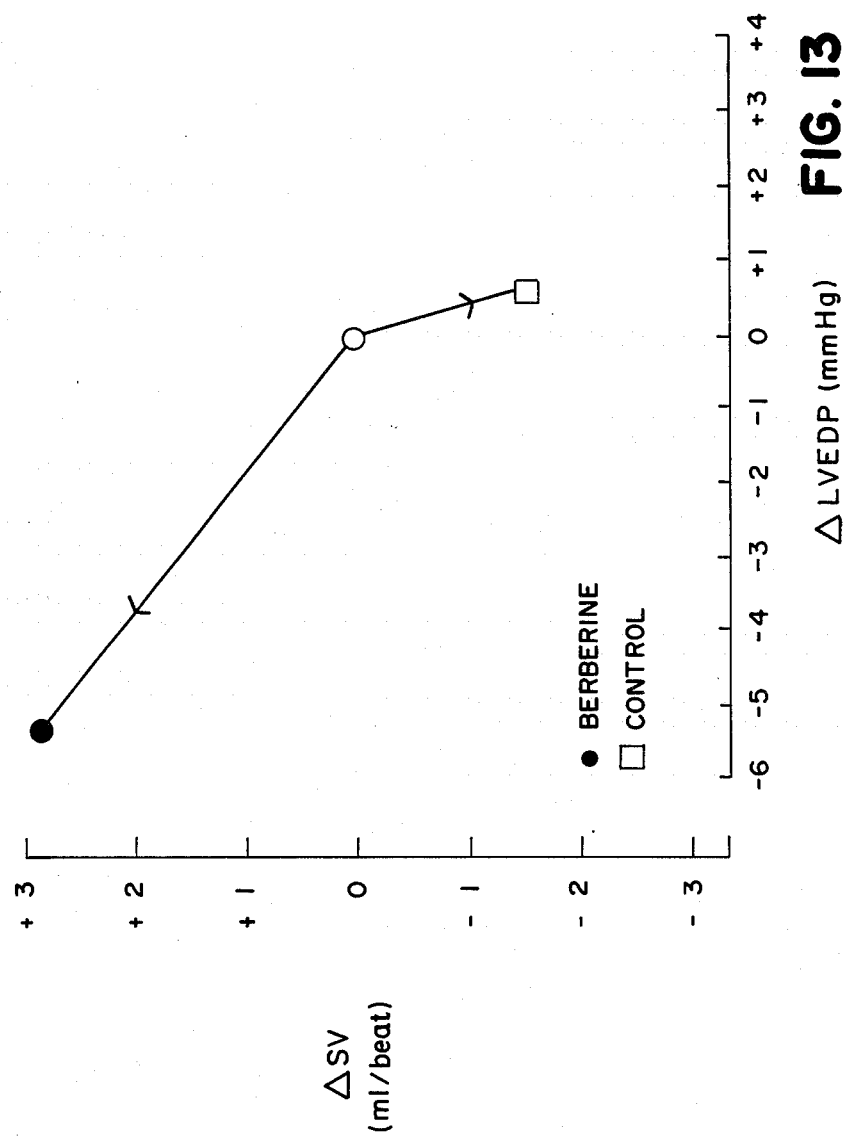
Figure 14:
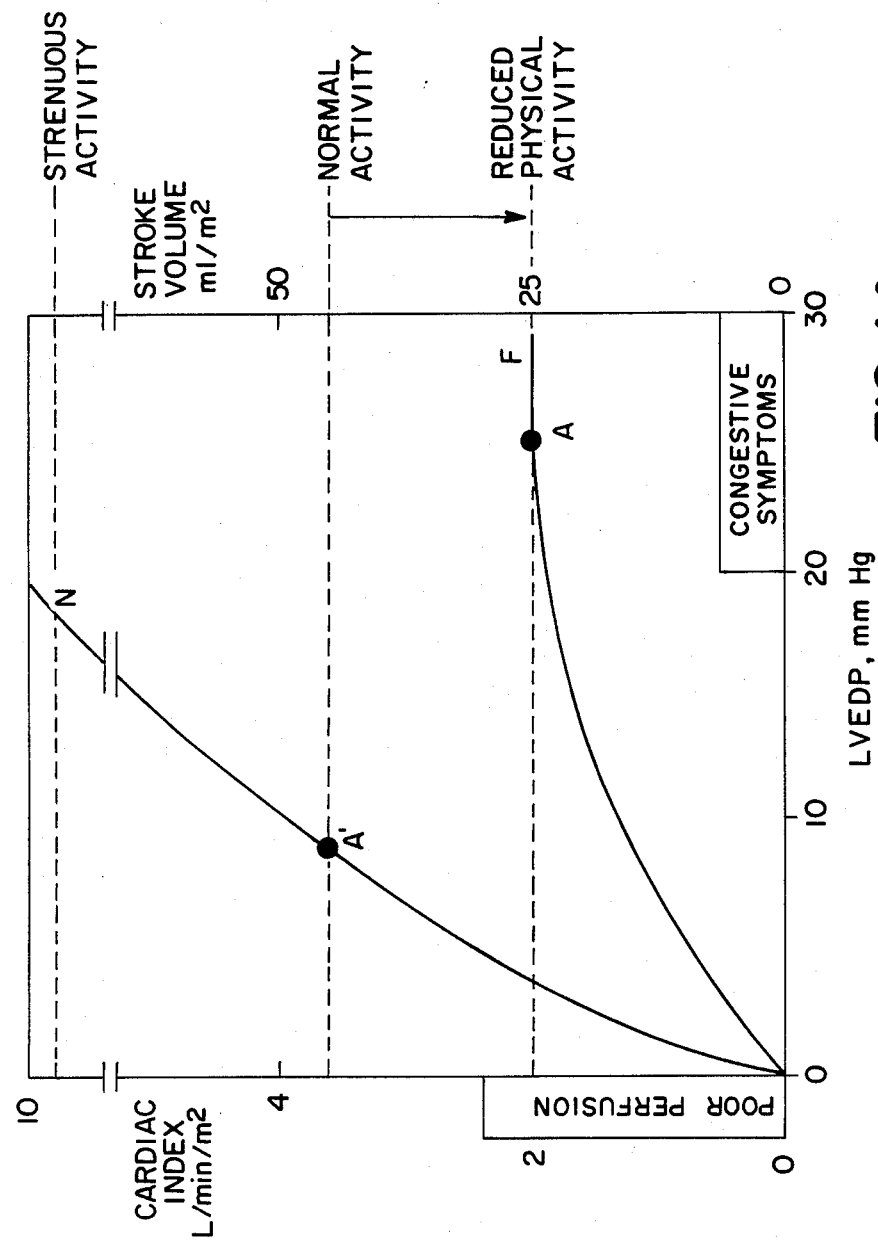
Figure 15:
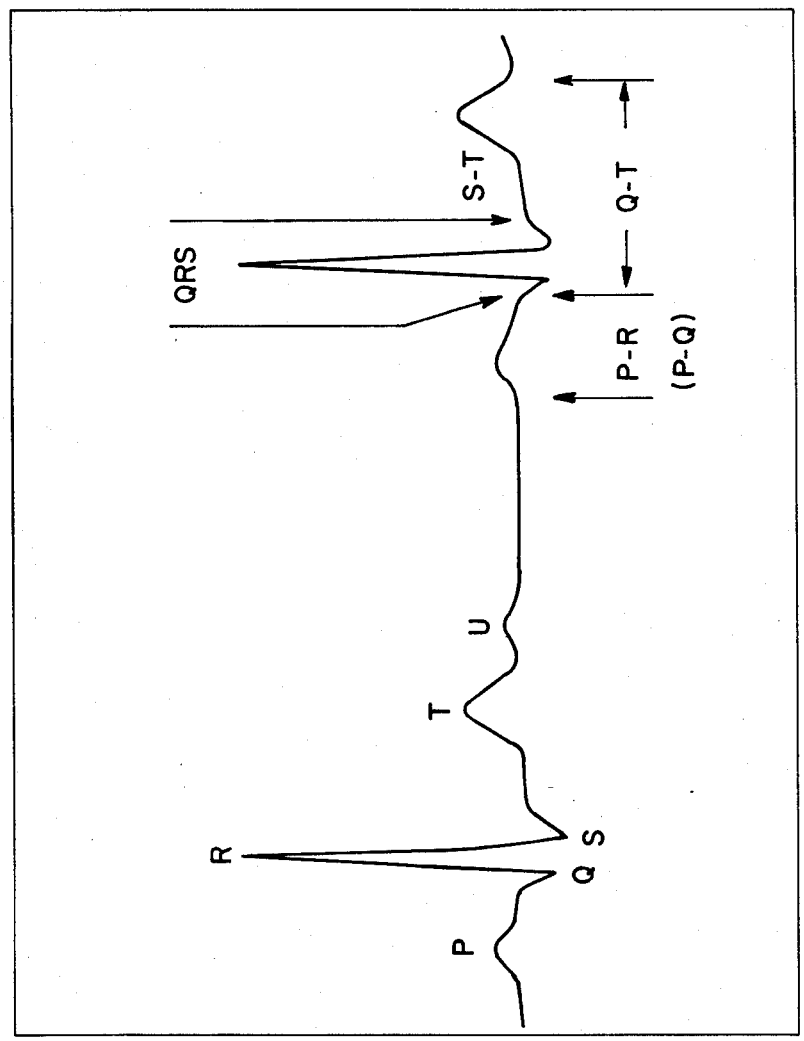

FIG. X. Changes in Cardiac Output (CO) by Berberine HCL. See test, FIG. 4. (**=p<0.01 for comparison between the groups).

FIG. XI. Changes in Stroke Volume (SV). (**=p<0.05 for comparison between the groups).

FIG. XII. Relationship Between Mean Changes in Cardia Output (CO) and left ventricular end diastolic pressure (LV EDP) from before to 30 min after berberine HCL infusion. Comparison with a control group.

FIG. XIII. Relationship between Mean Changes in Stroke Volume (SV) and Left Ventricular End Diastolic Pressure (LV EDP) from before to 30 min after Berberine HCl Infusions. Comparison with a control group.

Thus, while berberine increased left ventricular contractility (LVdP/dt), decreased left ventricular end diastolic pressure, decreased peripheral resistance and clearly improved left ventricular function, digitalis (ouabain) was completely ineffective. This indicates that berberine can be given successfully in such circumstances when digitalis is not effective such as in acute heart failure. In the cases in which cardiogenic shock is the most typical example, berberine similarly to beta adrenergic agonists was very effective. Moreover, it was reasonable to assume that when berberine improves left ventricular function to the same extent as beta adrenergic agonists, this improvement occurs with a smaller expenditure of oxygen, i.e., with smaller elevation of myocardial oxygen consumption, or even with a decrease in oxygen consumption. This was confirmed for berberine as shown above. Contributing, but not solely responsible for this property, will be (in the case of berberine), the lack of tachycardia, the decrease in afterload (lower arterial pressure), and the decrease in preload (lower left ventricular end diastolic pressure) and the probable reduction in left ventricular cavity dimensions. It should be emphasized that the fall in LVEDP due to the infusion of berberine was quite marked which is of great importance in the clinical situation of heart failure. These results indicate therefore that beside its effect of increasing contractility, of decrease afterload and peripheral resistance and of increasing cardiac output, berberine is also a potent preload reducing agent.

Other typical compounds of the invention perform in the same way. Coreximine, tetrahydropalmatine, berberrubine with certain variations also shown are comparable preload reduction.

These experiments (which were conducted in closed chest animals) show that berberine is not only effective in the non-failing heart but that indeed it is also very effective in the acute left ventricular failure situation which is the most crucially intense and life threatening circumstance in the gamut of cardiac failures. It shows that its effect is clearly superior to ouabain and probably comparable to beta adrenergic agonists over which it may have the advantage of influencing the determinant of oxygen consumption in such a way as to consume less oxygen. This last property may be of great advantage in patients in whom the shock syndrome or any other form of acute or chronic heart failure is due to ischemic heart disease and more particularly acute myocardial infarction. In these circumstances the increase in myocardial oxygen consumption may cause a worsening of the balance between oxygen supply and demand provoking at its more extreme cases myocardial tissue injury and necrosis (see Maroko, P. R. and Braunwald, E., "Effects of Metabolic and Pharmacologic Intervention on Myocardial Infarct Size Following Coronary Occlusion, *Circulation* 53 (Suppl. I): 1-162-I-168, 1976, which is incorporated herein by reference).

In summary, these experiments in the model of acute left ventricular failure demonstrate the following sought out properties: (a) Lack of tachycardia. Indeed average heart rate was reduced by 8 beat/min. (b) Decrease in afterload and in calculated total peripheral resistance, showing that this compound is an afterload reducing agent and a peripheral vasodilator. (c) Decrease in preload showing that in addition berberine is a preload reducing agent. (d) Increase in left ventricular dP/dt showing that berberine increases left ventricular contractility. This result is more impressive in this set of circumstances because aortic pressure was permitted to change, there was a modest fall and lower pressures artificially underestimate contractility measured by maximum dP/dt. In other words, the real increase in contractility is more than assessed by maximal dP/dt which is here reported.

Other typical compounds of the invention give comparable results. Tetrahydropalmatine, coreximine and berberrubine perform in an equivalent manner.

Figure 2:
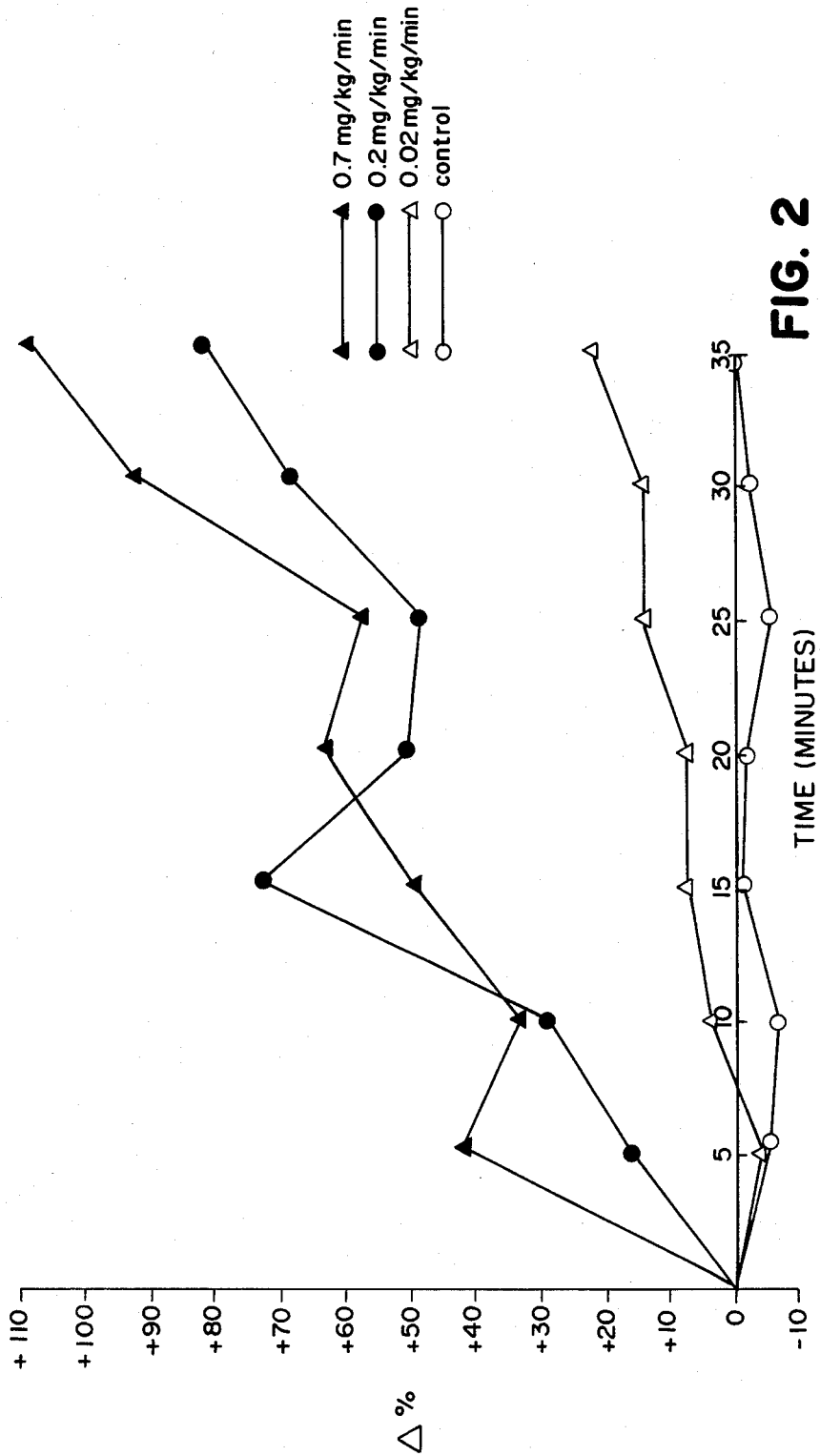
Figure 3:
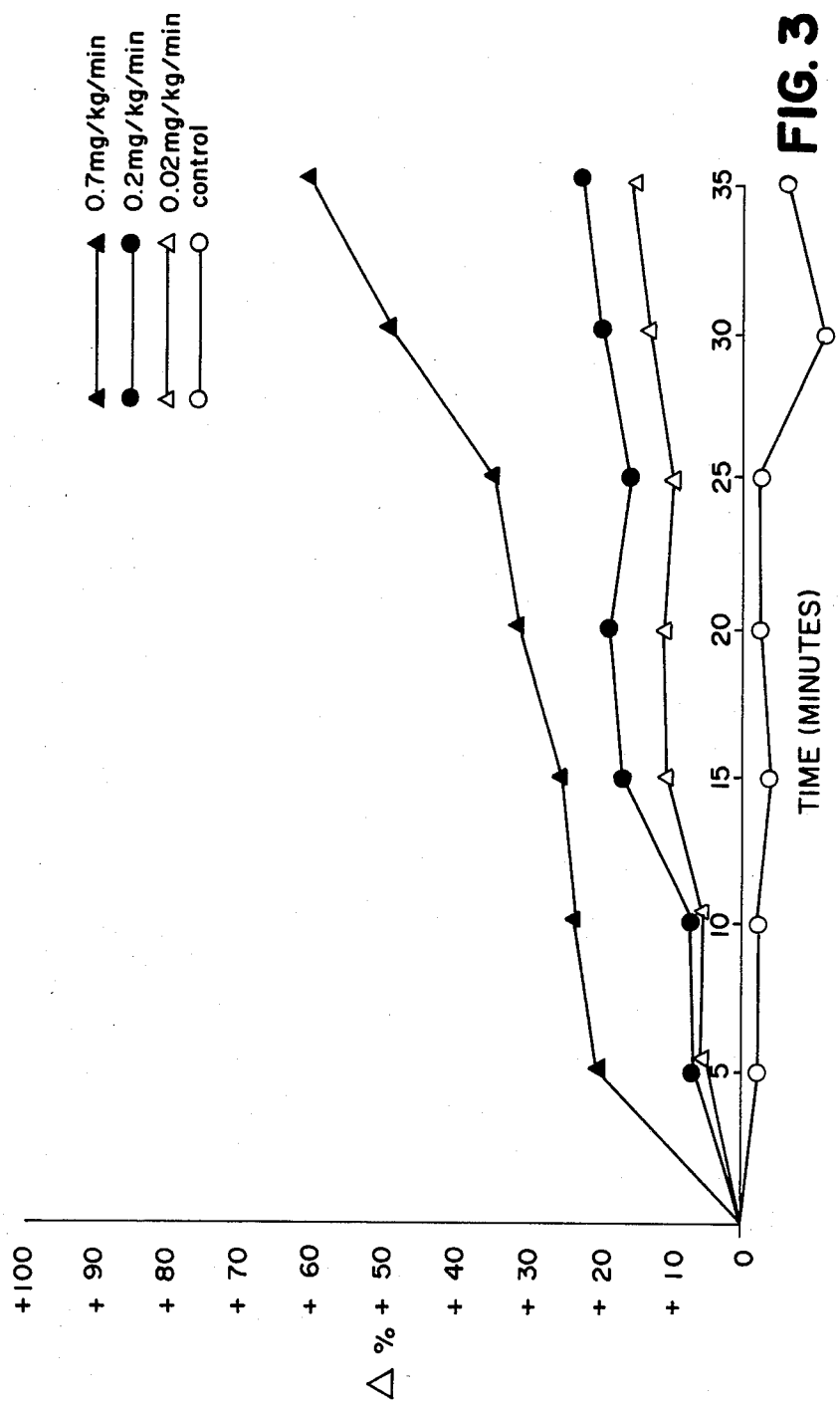
Figure 16:
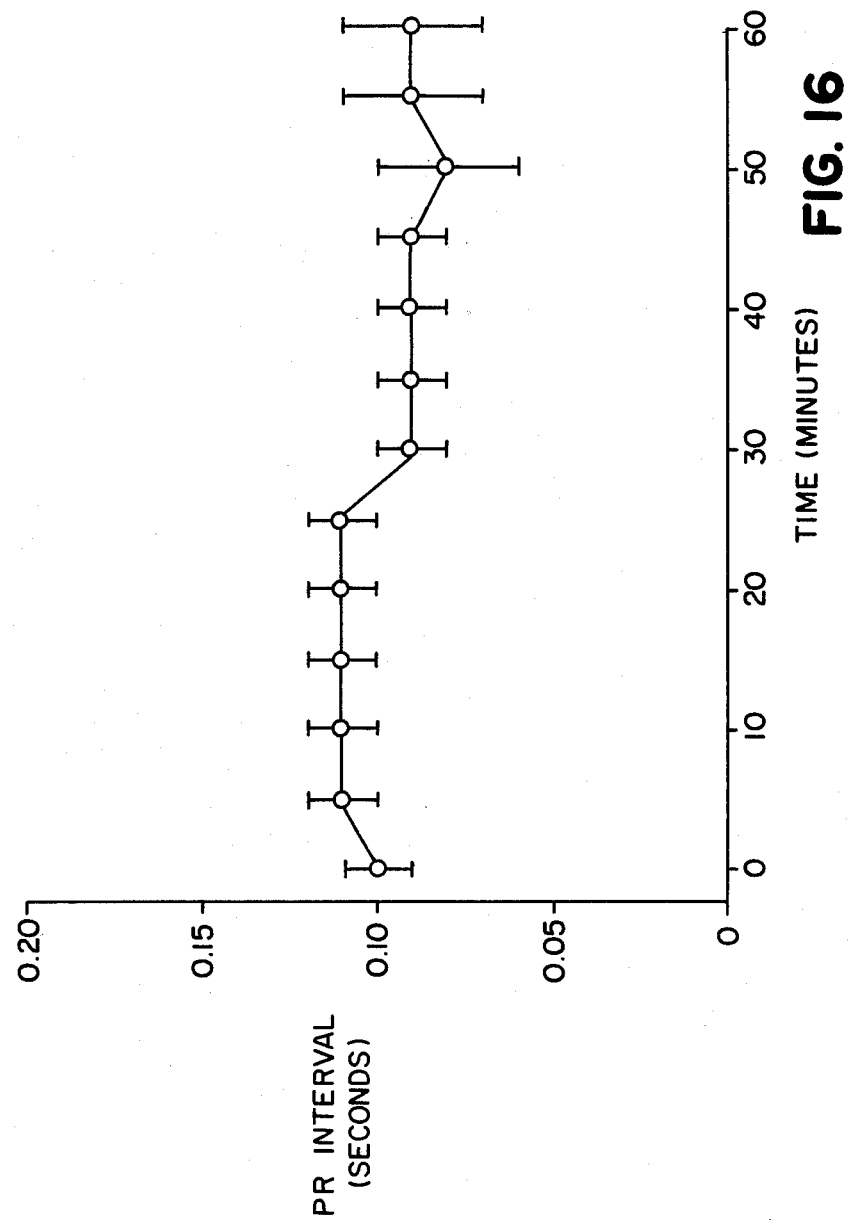
Figure 17:
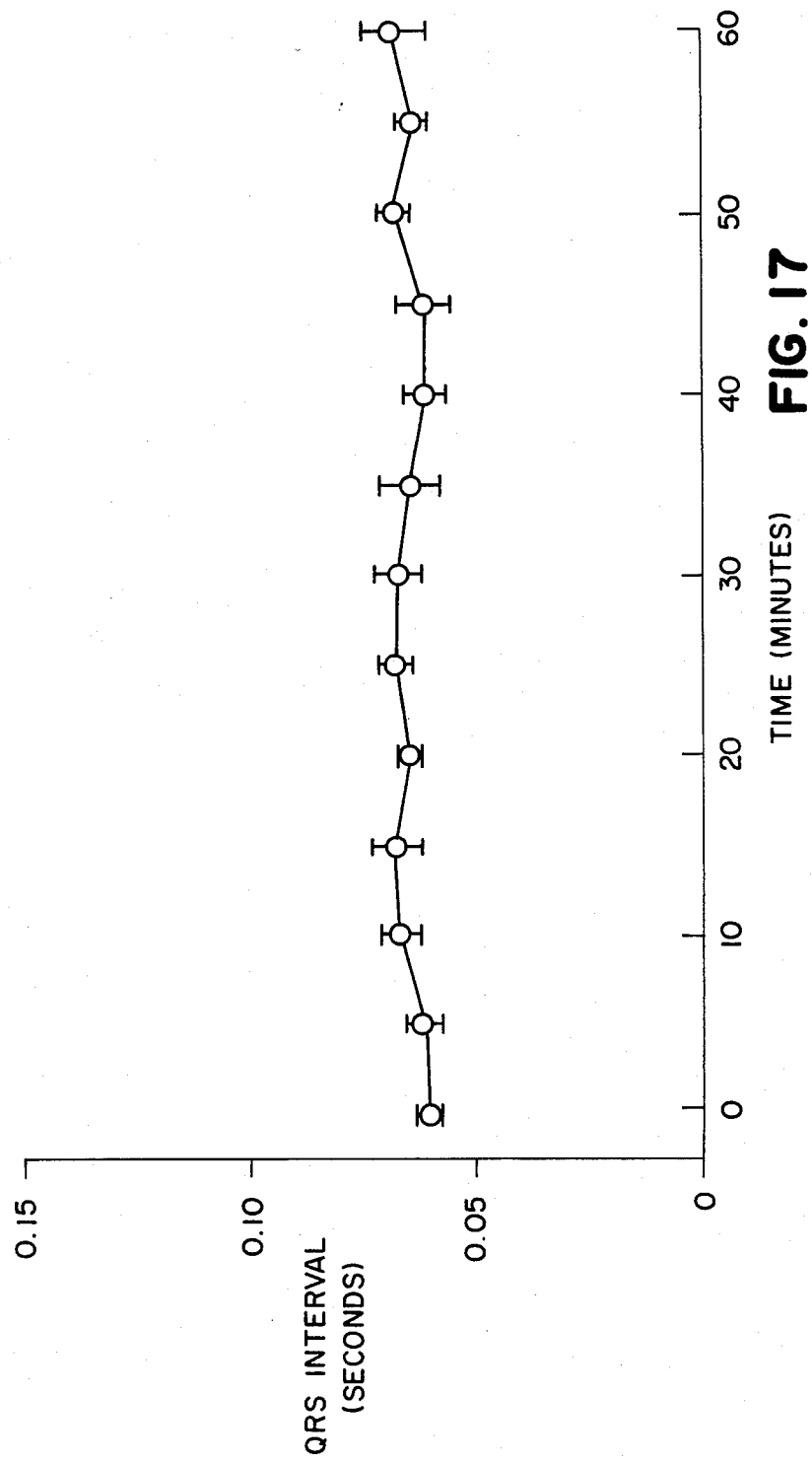

FIG. XIV (from Braunwald FIG. 16-2 page 512) shows the relationship between left ventricular end-diastolic pressure (LVEDP) and cardiac index (left ordinate) or stroke volume (right ordinate) in a normal (N) and a failing heart (F) of a man. The upper limit of normal of LVEDP (12 mm Hg) and lower limit of normal of CI (2.2—CI liters/min/m$^2$) are shown, as are the values associated with congestive symptoms (LVEDP 20 mm Hg) and with impaired perfusion (2.2 liters/min/m$^2$). A and A' represent the operating points at rest of a hypothetical patient with heart failure and of a normal person, respectively. Reduction of physical activity allows the failing heart to meet the demands of the metabolizing tissues.

This Fig. shows diagrammatically the relationship between LVEDP and cardiac index (left ordinate) or stroke volume (right ordinate) in a normal (N) and a failing heart (F). Viewed differently, the effect of berberine is to cause curve O through A of FIG. XIV (failing heart) to return to normal to the curve shown by OA' (normal). This result with berberine on the LVEDP is particularly significant.

The analysis of the "Starling Curve" in our previous related experiment in protocol HV (FIGS. XII and XIII and table XIII) that berberine and the other compounds of the invention improve left ventricular function and that this improvement is markedly superior to that achieved by digitalis. This is also demonstrated in FIG. XIV.

For a more complete understanding of the electrocardiographic data and findings, especially on waveforms, durations and intervals, the following may be informative.

The P wave of atrial depolarization is normally the initial wave of activity during the cardiac cycle. Ventricular muscle depolarization is represented by the QRS complex. A Q wave is an initial negative wave; an R wave is an initial positive wave or a positive wave following a Q wave; and an S wave is a negative deflection following an R wave. A QRS complex having a Q wave which returns to the base line but does not produce a positive wave is labeled a QS complex, and a second positive wave is labeled R'. The T wave represents ventricular muscle repolarization, and is sometimes followed by a small wave, the U wave. Repolarization of atrial muscle is represented by the $T_a$ (or $T_p$) wave, which occurs during the P-R interval and QRS complex. The interval between the end of the QRS complex and the onset of the T wave is the S-T segment. The interval between the P wave and the QRS complex is the P-R (or P-Q) interval, measured from the onset of atrial depolarization (P) to the onset of ventricular depolarization (Q). The duration is 0.12 to 0.20 s in the adult. Since AV nodal activation begins before the end of depolarization of atrial muscle, the P-R interval may be used as a rough approximation of AV conduction time.

The duration of the QRS complex (0.04 to 0.10 s) reflects the time required for depolarization of ventricular muscle. Block in a bundle branch prolongs it. An approximation of the refractory period of the ventricles may be obtained by measuring the Q-T interval (from the onset of the QRS to the end of the T wave). The Q-T interval is rate dependent and may be affected by numerous pathophysiologic influences. See FIG. XV.

In FIG. XV, the waves of the electrocardiogram—P, QRS, T, and U—are indicated. The measurements of the P-R interval, QRS complex, S-T segment, and QT interval are identified on the right.

It has been found in accordance with the invention following protocol Z, that berberine does not increase the P-R interval (FIG. XVI). This was so even when administered i.v. for 60' (0.7 mg/Kg/min) or a total of 42 mg/Kg. No manifestation of toxicity were observed.

In contrast, digitalis is known to increase the P-R interval. This is known to be related to causing atrio ventricular blocks. Braunwald, page 249 and Harrison's, page 1209, Goodman, pages 665–666.

FIG. XVII shows that the QRS complex or interval is not increased (i.e. virtually remains unchanged) over the period of i.v. administration. Antiarrhythmic drugs like quinidine and procainamide may prolong the QRS interval, which is not a desirable effect.

Berberine causes an overall increase in QTc interval, This effect is similar to quinidine and procainamide. This indicates an antiarrhythmic effect for berberine. Digitalis is known to shorten the QTc interval.

Thus, the data showed that berberine, while increasing the QTc, does not prolong the QRS interval. It shows also that in the dosage used, the drug is not toxic. In contrast, digitalis is known to increase P-R and to decrease QTc.

When dP/dt is increased by 43% (in experiment in protocol Z) QTc is increased by an average of 16%.

The antiarrhythmic properties of the compunds of the invention are further illustrated below.

Experiments were carried out to analyze the electrophysiologic properties of berberine (protocol TE). In this protocol closed-chest dogs were anesthetized with intravenous pentobarbital (30 mg/Kg). Electrode catheters were placed, under fluoroscopy, in the high right atrium, right ventricle, and in the aorta near the noncoronary aortic cusp to record His bundle potential. In addition aortic pressure (Statham gauge) and surface ECG were obtained. All parameters were recorded on an Electronic for Medicine polygraph (Model DR 8), with a paper speed of 100 mm/sec. The recordings were obtained before berberine treatment and after five successive five minute infusions of 0.2 mg/Kg/min of berberine in each one of the dogs. At each one of these time intervals recordings were done with the "spontaneous" normal sinus rhythm and with atrial and ventricular extrastimuli were given during the normal sinus as well as during the pacing phases of the experiment to determine the refractory period of the atria, atrio-ventricular node and of the His-Purkinje system and ventricle. Moreover, sinus node recovery time was measured.

The results showed that berberine in this dose did not chanbge the A-H, H-V and QRS intervals and that atrial refractory period did not change. Ventricular effective refractory period was increased by 11%. Sinus node recovery did not change. QTc changed by 13%; heart rate decreased by 8%. These experiments show again the potential antiarrhytnnic properties of the compounds of the invention. When coreximine is substituted in the above experiments comparable results are shown; likewise for tetrahydropalmatine and berberrubine.

Thus the compounds of the invention have the property to reduce, arrest or interrupt arrhythmias. This property was studied in different ways in order to include arrhythmias produced by different causative agents like drugs known to cause arrhythmias. This, the antiarrhythmic effect of the compounds of the invention were studies in models where arrhythmias were productd by digitalis, by aconitine and by coronary artery ligation.

The effect of the compounds of the invention is quite unexpected in that a biologically active drug which is positive inotropic does not normally have an antiarrhythmogenic effect. The implications of this finding are quite significant. Without enumerating all of the implications (the others being apparent to one of average skill in the art), it will be seen that this use of the compounds of the invention significantly increases the possibilities of use of digitalis-type cardiac glycosides both in the human and veterinary field. The caridac glycoside can be used with the compounds of the invention in the dosage in which the cardiac glycoside are commonly used with the result that there is a decrease in the risk of arrhythmias attributable to the cardiac glycoside especially when they are administered over a longer period of time; or perhaps, more importantly, cardiac glycosides like digitalis can now be used in accordance with the invention in a dosage in which the cardiac glycoside normally is toxic (or likely to cause arryhthmia) or has other adverse cardio-vascular effects). Thus, the compounds of the invention significantly broaden the therapeutic index of cardiac glycosides. This is a new and unexpected utility which provides a real incentive and removes a serious concern which traditionally existed with the cardiac glycosides.

For instance, it is generally accepted that ouabain has an average digitalizing dose from 0.30 to 0.50 mg when administered i.v., deslanoside 0.80 mg i.v.; digoxin 1.25 to 1.50 mg orally and 0.75 to 100 mg i.v.; digitoxin 0.70 to 1.20 mg orally and about 1.0 mg i.v. Dosages in excess are generally considered exposing the human patient to risk. (see, Braunwald, page 523). Similarly, in veterinary medicine corresponding dosages are considered exposing the animal to risks of arrhythmias. Accordingly, an aspect of the invention encompasses a compound of the invention in conjunction with an arrhythmic-causing drug, even in a concentration where such drug would cause arrhythmia were it used alone on the mammal.

The term "in conjunction" means not only in a mixture with a compound of the invention but means any combination which when in the biological system of the mammal permits the compounds of the invention and the arrhythmic effect to take place causing the drug to act on and in the same biological environment.

In the therepeutic method sense, it is contemplated that all or any part of the compounds of the invention be administered to the mammal before, together with or after the arrhythmia-causing drug, or any variation thereof.

It should be noted in this conjunction that aconitine is a drug which is considered generally not acceptable any longer because of its pronounced arrhythmic effects. The fact that a compound of the invention effectively controlled or negated this objectionable effect is a clear demonstration of the effectiveness of an antiarrhythmogenic effect.

It should be noted that both in the digitalis model of arrhythmias and the aconitine model of arrhythmias in which the experiments were done with the compounds of the invention are classical models to study antiarrhythmic drugs. This, the observation that a drug prevents, interrupts, reduces or abolishes arrhythmias in these models is taken by the knowledgeable or one skilled in the field to which the invention pertains not only to show their specific effectiveness against these drugs, but as their overall anti-arrhythmic properties.

In the compositions (or mixture) of the invention discussed above, the amount of the compound of the invention issued is the smallest amount necessary to cause a positive inotropic effect and the amount of arrhythmia-causing drug can be any concentration (or proportion relative the composition of the invention) and either in a concentration generally acceptable without causing arrhythmia or in such an amount as normally are considered arrhythmogenic.

For instance digitalis is administered intravenously, typically incrementally; the protoberberine may be administered incrementally before, simultaneously or after the administration of digitalis or the protoberberine may be infused at a steady rate during the administration of the digitalis. The amount of digitalis thus administered may be less than is usual, the same amount or more than usual depending on the circumstances and condition of the patient.

For maintenance therapy it is in the range of about 0.001 to 50 mg/Kg, for the compounds of the invention depending on the judgement of the physician's recommendations.

A study was carried out to examine the effects of the simultaneous administration of berberine on digitalis (i.e. ouabain) produced arrhythmias. In dogs which were dosed simultaneously with berberine and ouabain (constant infusion) ventricular ectopic activity (VEA) and ventricular tachycardia (VT) appeared significantly later than in dogs which were dosed only with ouabain. This demonstrates that these ventricular arrhythmias appears only with a higher dose of ouabain and that berberine significantly and markedly reduces the occurrence of these life threatening ventricular arrhythmias. The data show that berberine protects the dogs from developing ventricular arrhythmias. This property may be of extreme clinical importance because it suggests that by giving berberine, the therapeutic ratio of digitalis-like drugs can be increased and that patients may be able to receive higher doses of digitalis with a lesser risk of having the most feared toxic effect, that of ventricular arrhythmias.

The experiments were conducted in closed-chest anesthetized dogs which were randomized in three groups. All received ouabain 0.03 mg/Kg as a bolus intravenously and thereafter a continuous infusion with a constant rate of 0.0006 mg/Kg/min until death. The first group did not receive any other intervention and served as control. The second group received simultaneously berberine 1 mg/Kg intravenously as a bolus and then 0.2 mg/Kg/min as a continous infusion. The third group received berberine only after the appearance of VEA in a frequency of 50% of more of all systoles.

In the controls, the time of appearance of 25% of VEA, 50% of VEA and VT was respectively 22±4.7 min, 23.9±4.7 min and 30.1±6.5 min and in the dogs treated simultaneously with berberine it was 66.5±14.6 min ($p<0.0005$), 66.7±15.3 min ($p<0.005$) and 96.1±15.1 min ($p<0.005$). This demonstrated that the simultaneous treatment with berberine prolonged the time of appearance of VEA and more importantly of VT by around 300% which is clinically extremely important and statistically highly significant.

This data was analyzed also from the point of view of how much digitalis has to be given before provoking the arrhythmia. Thus, for example, in the control situation it was necessary only to administer 0.04 mg/Kg of ouabain to provoke VT, while in the berberine treated dogs the dose was significantly higher, i.e. 0.088 mg/Kg.

Also in these experiments the frequency of occurrence of any arrhythmias was analyzed (VEA more than 25%, VT or death). It was found that at 30 minutes in the control, twelve dogs had arrhythmias and four did not, while in the berberine treated one had arrhythmia and eight did not. This is a highly significant difference ($p<0.005$) by Fisher Exact test). When analyzed at 45 minutes, in the control group fourteen had arrhythmias and two did not, while in the treated group three had arrhythmias and six had not. This is also highly significant ($p<0.02$ by Fisher Exact test). When analyzed after 60 minutes, all sixteen controls has arrhythmias while in a treated group three had arrhythmias and six did not. This is highly significant ($p<0.005$ by Fisher Exact test). Finally, when analyzed after 90 minutes, in the control group all had arrhythmias and in the treated group four had arrhythmias and five did not. This also is highly significant ($p<0.001$ by Fisher Exact test).

When berberine treatment started only after the appearance of 50% of VEA, the time of appearance of sustained VT was 30.1±6.5 minutes in the control group, and 84.5±13.8 minutes in the berberine treated group ($p<0.005$). This demonstrates that berberine when given when VEA are already frequent, will delay by more than 250% the appearance of sustained VT. Also when analyzed by the amount of ouabain that provoked VT it was 0.048 mg/Kg in the controls and 0.080 mg/Kg in the treated dogs.

Moreover, the effects of intravenous bolus injection of berberine (0.4 to 1 mg/Kg) was studied (in comparison to dextrose 5% injection). They were administered when the dogs exhibited VT and were considered effective if they succeeded to revert VT into sinus rhythm within five minutes. With the injection of placebo (dextrose) there was no effect in any of the twelve instances. With berberine injection 30 out of 41 were effective. This is statistically highly siginificant ($p<0.005$) and biologically (clinically) of extreme importance.

In the above experiment, other typical species of the compounds of the invention are tested and give comparable results. Berberrubine, tetrahydropalmatine and coreximine likewise gave satisfactory results showing their antiarrhythmic and antiarrhythmogenic properties.

It may also be noteworthy that in two berberine dogs ventricular fibrillation reverted without any other therapy. This is remarkable and suggests an increase in threshold for ventricular fibrillation.

Berberine can counteract the vasoconstrictor effect of digitalis on the peripheral vessels. This is shown by the observation that the diastolic pressure in the control group which received only digitalis rose after 10, 20, 30 and 60 minutes respectively by 31±9%, 16±11%, 34±15% and 16±7% while in the dogs that received berberine in addition to digitalis the diastolic pressure fell by −9±5%, −13±9%, −13±10% and −20±11%. All changes were statistically significant.

Since it was demonstrated above that the administration of digitalis and berberine has obvious advantages from an antiarrhythmic point of view, the effect of the association of ouabain and berberine on contractility (LV dP/dt) will be examined.

In anesthetized closed chest dogs the systolic arterial pressure was maintained constant with a reservoir full of heparinized blood (as in protocol "M" and "Z" described above) and a "pigtail" and Millar catheter were introduced into the left ventricular cavity (as in protocol "Z" and "HV", described above). All data was recorded on 8 channel polygraph (Gould Instruments) with a paper speed of 200 mm/sec when necessary and at 2 mm/sec constantly.

In seven dogs ouabain 0.03 mg/Kg given intravenously as a bolus, resulted in a progressive increase in dP/dt after 5, 10, 15, 20, 25 and 30 minutes by 17±2%, 24±3%, 34±4%, 36±4% and 44±6% and 49±7% of the initial value of peak LV dP/dt respectively. Then berberine (0.7 mg/Kg/min) was infused for the next 30 minutes and LV dP/dt further increased to 87±10%, 82±13%, 87±13%, 95±16%, 96±16% and 94±14% of the initial LV dP/dt respectively. The increases in dP/dt when only berberine (0.7 mg/Kg/min) without digitalis were given was at 5, 10, 15, 20, 25 and 30 minutes 3035 4%, 36±3%, 39±3%, 42±5%, 39±5% and 40±7%. Thus, the increase in maximal LV dP/dt was both statistically and biologically highly significant when the effect of the two drugs was compared to the effect of each one of them alone (Table XVII). It is noteworthy that the increase in contractility was more than the summation of the effects of both when given separately. This suggests that the effects are more than additive but synergistic.

Coreximine, tetrahydropalmatine or berberrubine perform in the same manner.

Other select compounds of the invention also performed markedly well as antiarrhythmias.

Therefore, the usefulness of the compounds of the invention is markedly increased because:

(1) Berberine, per se, (and the other compounds of the invention) increases contractility and cardiac performance with an excellent therapeutic ratio.

(2) Berberine (and other compounds of the invention) increases the therapeutic ratio of digitalis when the two compounds are given together, permitting the administration of digitalis type cardiacglycoside in an amount greater than ever given before with less toxic side effects (ventricular ectopic beats, ventricular tachycardia, ventricular fibrillation).

(3) The combination of drugs has additive or synergistic properties in the treatment of contractility.

(4) The compounds of the invention like berberine (and the other compounds of the invention) can counteract the undesired vasoconstrictor effect of digitalis type cardiacglycoside on the peripheral vessels.

(5) The compounds of the invention like berberine (and the other compounds of the invention) is an effective antiarrhythmic agent. It is effective in abolishing premature ventricular beats and in supressing established ventricular tachycardia, an extremely severe and life threatening arrhythmia, by administration before, during, or after administration of digitalis type cardiacglycoside, and is expected to reverse ventricular fibrillation.

Moss et al (Circulation 64, No. 6, 1981, p.<1150) suggests that digitalis therapy increases the early post hospital mortality of myocardial infarction patients with combined electrical and mechanical dysfunction. The antiarrhythmic activity of berberine (and the other compounds of the invention) and its synergistic activity with digitalis type cardiacglycoside shows that treatment with berberine (and the other compounds of the invention) or the combination of berberine (and the other compounds of the invention) and digitalis type cardiacglycoside is beneficial in such cases.

To examine the effects of berberine on arrhythmias produced by intravenous infusion of aconitine in fifteen dogs after development of VEA, of at least 50% of the beats or more, the dogs were given berberine intravenously as a bolus (1-5 mg/Kg) or 5% dextrose in water. In the treated group, regression of the arrhythmias to normal sinus or supraventricular rhythm occurred in 78% of the dogs, but in the controls it occurred only in 20% which is statistically ($p<0.05$) and biologically significant. It is noteworthy that in all but one of these successful experiments, there was a regression of VT to normal sinus rhythm and that in two cases ventricular fibrillation reverted to normal sinus rhythm. Thus, berberine was effective also in this model of ventricular arrhythmias. When berberine is substituted by other typical species of the compounds of the invention, comparable results are obtained.

To verify the effect of berberine on supraventricular arrhythmias in another group of dogs, the topical application of aconitine (0.04%) solution to the atria provoked either atrial ecotopic beats, atrial tachycardia or atrial fibrillation. The injection of intravenous berberine in a bolus (1-5 mg/Kg) was effective in abolishing these arrhythmias in contrast to the injections of placebo (5% dextrose in water). This shows that besides being effective in abolishing the most severe and life threatening ventricular arrhythmias, is also abolished atrial ectopics, atrial tachycardia and interrupted atrial fibrillation which are frequently of clinical importance to the well-being of the patients and when abolished can improve the hemodynamics and decrease the risk of embolization. The other typical species of the compounds of the invention performed in like manner.

Another series of experiments were done using the rat model of acute coronary artery occlusion. In these experiments the effect of berberine was examined on mortality. Thus, Sprague-Daley rats (Charles River) weighing over 300 grams were anesthetized with ether, their chest opened in the 5th left intercostal space their heart everted and the left main coronary occluded with a surgical stitch. Thereafter the heart was repositioned and the thorax closed with a purse string suture, as described in more detail by us previously (Maclean, Fishbein, M. C., Braunwald, E. and Maroko, P. R., Long Term Presentation of Ischemic Myocardium After Experimental Coronary Artery Occlusion. *J. Clin. Inv.* 61, pages 541-551, 1978 and also in Maclean, D., Fishbein, M. D., Maroko, P. R. and Braunwald, Hyaluronidase-Induced Reductions In Myocardial Infarct Size. *Science*, 194, pages 199-200 (1976)). The mortality in rats weighing over 300 mg was greater than in smaller rats.

After finishing the surgical procedure, the rats were randomized into controls (injection of 5% dextrose in water) and berberine treated (1 mg/Kg intravenously as a bolus). In the controls seventeen out of twenty-four rats died within the first fifteen minutes, while in the berberine treated group only six out of twenty-two rats died which is biologically and statistically highly significant ($x^2=8.7$, $p<0.01$).

This experiment demonstrated the effectiveness of berberine in preventing arrhythmic death after coronary artery occlusion when the arrhythmias are cased by the ischemic insult or injury to the myocardium.

This experiment shows that berberine is effective not only in "automatic" but also in the "re-entry" type of arrhythmias. The clinical application is to patients with ischemic heart disease and more specifically to those with acute myocardial infarction. The administration of the compounds of the invention is thus useful in patients prone to arrhythmias due to coronary artery obstruction or coronary spasm or myocardial infarction of any etiology as well as ischemic sudden death.

It was unexpected that 50% of the rats that were monitored by electrocardiography died due to ventricular fibrillation and 50% died with complete A-V blocks, which suggested that berberine did not only prevent death from fibrillation but also due to A-V blocks.

Whena specific species of the compounds of the invention are used individually in the above work, like performance was observed. With berberrubine, tetrahydropalmatine, and coreximine, like antiarrhythmic control is observable under the same experimental conditions.

Another embodiment of the invention is the use of the compounds of the invention in the control of mammal shock, such shock having its clinical symptom or manifestation, a decreased cardiac output. The most important consequence of shock is decrease of blood flow to the vital organs such as brain, heart and kidneys. Thus, commonly the most obvious result of treatment of shock are evaluated by urinary output.

Regardless of etiology, circulatory shock is a condition which has a manifestation diminished blood flow and insufficient tissue oxygenation resulting therefrom. Shock is related initially to reduced blood volume, decreased cardiac output or change in peripheral resistance.

The etiology of circulatory shock can be classified into several categories: hypovolemic shock, septicemic, anaphylactic, hemorrhagic, neurogenic vasculogenic shock, and cardiogenic shock and others, all of which are contemplated within the scope of the invention.

Hypovolemic shock results from a significant reduction in blood volume. The reduction frequently arises as a result of major tissue trauma such as ruptures of the liver or spleen or severance of a major artery.

Vasculogenic shock results from vascular changes frequently caused by bacterial infection and bacterial toxins associated therewith. Endotoxins (such as LPS) are especially capable of inducing shock.

Cardiogenic shock results from abnormalites in cardiac pumping capacity. The compounds of the inventions are effective in relieving, preventing or controlling (to varying degrees) and arresting these various forms on non-cardiogenic shocks in addition to their value in the control of cardiogenic shock.

For a discussion of circulatory shock in veterinary and human medicine, attention is invited to Jones et al, pages 583 to 593, and to Braunwald, chapter 18, both of which are incorporated by reference.

In noncardiogenic shocks the goal of the therapy is to restore systemic arterial pressure with adequate blood flow to the important organs. In many shock syndromes especially when they progress for several hours, a peripheral vasoconstriction appears which aggrevates the shock syndrome by reducing blood and oxygen supply to the tissues distal to the constriction. (See Rushmer, Van Citters and D. Franklin-DeFiuitia and classification of various forms of shock, Shock Pathology and Therapy, Bock, K. D. Academic Press 1962, pgs. 1–22) by R. C. Hehei, R. H. Ditzman, G. J. Motsay, C. B. Beckman, C. H. Shafney, "Growth of the Concept of Shock and Review of Status and Knowledge", pages 377–409, Steroids and Shock. J. T. Glenn, University Park Press, 1974.

Moreover, there is a depression in myocardial contractility. (See, *Myocardial Depressant Factor and Circulatory Shock*, A. M. Lefer, Klinische Wochenschrift 52: 358–370, 1974 and see *Left Ventricular Performance in Endotoxic Shock in Dogs*, W. G. Guntheroth, J. P. Jacky, S. Kawabori, J. G. Stevenson, A. H. Moreno, Amer. J. Physical 242: H172–H176, 1982).

Accordingly, the effects of berberine were studied in the model of endotoxic shock in dogs, in which the endotoxic shock correspond to that provoked by gram negative bacteria with injection of lipo polysacharides (LPS).

The usefulness of the compounds of the invention in controlling shock is illustrated further as follows.

Intravenous administration of endotoxin (LPS), 5 mg produced an immediate and precipitous fall in arterial pressure. In dogs which had been given endotoxin treatment with berberine increased pulse pressure, systolic pressure and dP/dt resulted. No cardiac arrhythmias or conduction defect was observed. In contrast, the control dogs showed a gradual decrease of dP/dt, systolic pressure and pulse pressure. ECG showed sinus bradycardia followed by idioventricular rhythm.

The response to the following 5% dextrose in water infusion in the berberine treated dogs was much more marked as far as increase in systemic arterial pressure and left ventricular dP/dt.

Nineteen closed-chest barbiturate anesthetized with artificial respiration dogs were studied. All measurements were done by the technique described before LPS. 5 mg was given and resulted in a precipitous fall of arterial systolic pressure to $56\pm4$ mmHg and diastolic pressure to $33\pm4$ mmHg from their original $138\pm8/106\pm8$ mmHg. After two hours the dogs were randomized to controls (given as placebo 5% of dextrose in water) and berberine treated dogs which were treated to the minimal dose that will result in an elevation of systemic systolic arterial pressure by at least 5 mmHg. This small dose $0.053\pm0.008$ mg/Kg/min was then used throughout the experiments. In the dogs that received placebo within fifteen minutes systolic pressure continued to fall and decreased further to $50\pm6$ mmHg while in the berberine treated it rose to $66\pm4$ mmHg. This is statistically highly significant. At the same time peak left ventricular dP/dt fell in the control dogs to $1050\pm145$ mmHg/sec while it increased to $2062\pm204$ mmHg/sec in the berberine treated group which is statistically highly significant. The pulse pressure (systolic minus diastolic pressures) did not change in the control group but increased significantly from $24\pm2$ to $32\pm2$ mmHg ($p<0.005$) in the treated group. Thus, it was demonstrated that in the endotoxic shock, the infusion of very low doses of berberine resulted in a very marked increase in contractility and improvement in hemodynamics.

At this time, i.e., two hours and fifteen minutes after administration of LPS, 1000 ml of 5% of dextrose in water was administered to all dogs during the next forty-five minutes. This was done since in the treatment of all hypovolemic shocks (which include the endotoxic shock) the treatment has to include augmentation of intravascular volume with infused fluids.

The systemic systolic arterial pressure increased to $107\pm5$ mmHg in the controls, but increase more to $127\pm6$ mmHg in the berberine treated dogs ($p<0.02$). Thus, while in the control dogs the final systolic pressure was significantly lower than initial (i.e., before LPS infusion) pressure $140\pm7$ vs $107\pm5$ mmHg ($p<0.001$), in berberine treated dogs the systolic pressure after treatment was not statistically different from that before shock $136\pm10$ and $127\pm6$ mmHg ($T=1.01$, $p<0.40$). Thus the treatment with berberine and 5% dextrose in water restored the systolic arterial pressure while this treatment without berberine did not do so.

Peak left ventricular dP/dt was in the treated group $3742\pm305$ mmHg which is significantly higher ($p<0.001$) by approximately 50% than its dP/dt before shock, $2565\pm166$ mmHg. This shows that whey systolic arterial pressure (and systolic LV pressures) were restored the dP/dt was 50% more than in the normal, before shock state, which indicates on the one hand again, the positive inotropic properties of berberine and, on the other hand, that the complete restoration of the systolic pressure that occurred in treated dogs (but not in the controls) should be credited this positive inotropic effect of berberine.

Urinary output during the second hour of shock (before berberine or placebo treatments) and the third hour of shock (when the dogs were treated with either berberine or placebo) were compared in each dog. This analysis is of crucial importance since it would indicate the restoration of effective organ perfusion which in the case of the kidneys results in urinary output. In the control dogs the urinary output continued to decrease and in the third hour urinary output was less by approximately 50 ml than in the second hour, i.e. 31 $51.7\pm32.9$ ml/hour. In contrast, the berberine treated dogs urinary output increased from the second (pre-treatment) to the third (treatment) by $30.5\pm14.3$ ml. This difference is biologically important and statistically significant (p 0.025). When the dosage is increased to twice as much, even faster and more pronounced improvements are observed.

The series of experiments is repeated using tetrahydropalmataine and comparing it with LPS. Like positive results are obtained and the endotoxic shock cause by LPS is controlled. Parallel experiments with representative series of the compounds of the invention gives comparable results, including the berberrubine and coreximine.

When the dosage is increased to twice as much, even faster and more pronounced improvements are observed.

The embodiment of the invention wherein the compounds of the invention are useful in the treatment of hypovolemic shock (including endotoxic shock) in a mammal is very noteworthy. That the compouds of the invention are also capable of restoring systolic arterial pressure after shock underscores the potency and effect even of their positive inotropic effect. A compound which is a positive inotrope is not necessarily a compound which corrects or alleviates shock, nor for that matter restores systolic pressure after shock.

In conclusion, berberine treatment was highly beneficial in treatment of this type of shock syndrome by increasing contractility, imposing (or restoring normal) arterial pressure and ameliorating organ perfusion as reflexted by urinary output. There were also no noticeable toxic side effects such as arrhythmias.

When given orally in variable doses (200-1000 mg/Kg) to rabbits and cats improvements in systemic arterial pressure and left ventricular dP/dt comparable to those obtained when the compounds of the invention were given intravenously. The effects were observed after approximately thirty minutes. Like results are obtained when the compounds of the invention are administered in the dosage necessary for the desired effects to dogs.

From this and other data, there is indirect evidence that berberine typically is quite effectively utilized during the first 24 hours and yet that its effect is not transient but extends over several hours. This utilization of berberine and other compounds of the invention has favorable implications for oral administration. It is a akin to a retard effect. It means that the administration of the compounds of the invention need not be as frequent, under appropriate circumstances.

The protoberine alkaloids of the invention are administered in the manner most appropriate under the circumstances. Administration may be oral, subcutaneous or intramuscular injection. The compounds may be administered by intravenous route, parenterally. It has been noted that berberine is soluble (among others) in sugar solutions so that it may be often well-administered by intravenous route.

Preferred is oral administration to patient in need of cardiac therapy whether it is in the non-failing or failing heart.

The dose in which the compounds of the invention are to be administered depends of course as discussed above on the circumstances of the patient, in particular, whether or not it is a situation where cardiac arrest or failing heart is occurring or whether it is in a non-failing heart situation for therapeutic purposes. In either situation, the dose is that minimum dose which shows a beneficial effect. This may be observed by the measurement of the symptoms which are clinically significant.

Thereafter the dose may be such as to sustain the beneficial effect on an hourly or daily basis such as follows. Under appropriate circumstances where sustaining therapy is desired, as little as 0.001 mg/kg or even less may be administered. Generally amounts over 5 g/kg are not necessary since they may be uneconomical unless very fast action is necessary in emergency situations. In those cases a theraputically sufficient amount should be administered. Where severe cardiac decompensation is present and the patient has not yet received any protoberberine alkaloid of the invention it may be given immediately followed by treatment at the appropriate rate. Optimal benefit dosage is maintained and the maintainence dose can be adjusted correspondingly, that is usually from 0.01 to 0.2 mg/kg per day. When an adequate level of improvement is observed the dosage may be reduced.

When it is desired by the physician that beneficial results be obtained in minutes rather than in hours, intravenous medication is indicated. The compound of the invention may be dissolved in sterile water or some other sterile medium such as 5 percent dextrose in water or saline. The administration may be all at once or alternatively infused gradually over the period of an hour or so. Continuous monitoring is maintained so that the infusion may be stopped when the desired effect is achieved. Thereafter a maintenance dosage is administered or whatever dosage is advisable to maintain an adequate level of improvement which may be administered orally or by injection. These therapeutic measures are known to one skilled in the art and need not be detailed more here.

As shown from the data above and elsewhere, the compounds of the inventions have a therapeutic index significantly broader than that of digitalis. Digitalis has a therapeutic dose approximately 50 to 60% of the toxic dose.

Variations in onset of action or speed of action and duration is likely to be observed between the various compounds of the invention.

The invention also as discussed above contemplates the use of the compounds of the invention in veterinary applications. What has been disclosed herein above and hereinafter is in accordance with the invention applicable to the veterinary field, e.g the treatment of animals as well as to humans. To amplify more specifically to those knowledgable in the veterinary arts it will be noted that cardiac glucosides are also useful in the therapy of animals for congestive heart failure. See *Veterinary Pharmaceutical and Biologicals* 1980/1981, Horwal Publishing Company for instance pages 16 16/120, 122, 176, 177, ("VPCB"), which is incorporated herein by reference and *Veterinary Pharmacology and Therapeutics*, Jones, et al., Iowa State University Press., 4th Ed. 1977, pp. 519-527 ("Jones et al").

The compounds of the invention therefore are valuable in animal species treatment. e.g. equine, bovine, pigs and swine, feline, canine and aviano as well as others to replace, or to be used in conjunction with (as described in accordance with the invention), cardiac glycosides commonly used in veterinary therapy, like digitoxin, gitoxin, gitalin, ouabain, and others.

The dosages in which they are used are described elsewhere herein. For other details, one skilled in the art is referred to Jones et al. which is incorporated herein by reference, especially chapter 24, Cardiac Drugs.

The compounds of the invention are also useful as arryhythmic drugs, as described herein above, to replace or supplement those like quinidine, procainamide or propanolol, lidocaine, and diphenylhydantoin, conventionally used in veterinary sciences. For other drugs which alleviate or suppress arryhythmia, see VPCB, page 527. The compounds of the invention are therefore useful to replace or in conjunction with such antiarrhythmia compounds like the phenothiazines such as promazine, chlorpromazine and promazine (acetylpromazine) and others which are known to reduce arrhythmias in animals. However these drugs, because of their narrow therapeutic index or low effectiveness or objectionable side effects, have not been adequately satisfactory.

Cardio-stimulatory and vasoactive drugs are used in the treatment of circulatory shock in animals. Drugs commonly used like sympathetic agonists (norepinephrine, epinephrine or isoproterenol) levarterenol, steroids and others described in Booth et al.) have shortcomings. The compounds of the invention provide valuable new therapeutic agents in that respect. A particular malignant form of circulatory shock observed in horses afflicted with the acute colitis (colitis X) syndrome lends itself to treatment with the compound of the invention particularly well.

All of the uses, including controlling various forms of shock like hypovolemic or vasculogenic shock described above, are of course equally applicable for the various compounds of the invention or the various animal species.

Animal health care and the use of drugs for such care, maintenance and therapeutic purposes have and are continuing to assume greater importance in the country. The scientific literature in veterinary sciences attests to the importance of animal care with drugs. The compounds of the invention are particularly useful as the user describes because of their wide spectrum of properties but especially in edible animals because of wide therapeutic range and low toxicity.

The treatment of these disorders in the veterinary field on animals species is especially important when the animal being treated is of great value as is the case with a thoroughbred horse or a valuable show animal.

The actual determination of the numerical therapeutic eg., cardiotonic dosage definitive or advisable for a particular compound of the invention is readily obtained according to the above-described standard test procedures by technicians versed in pharmacological test procedures, without any need for any extensive experimentation. The percentages of active component in the composition of the invention and method for increasing cardiac contractility and for the other beneficial effects obtained by the compounds of the invention, may be varied so that a suitable dosage is obtained. The dosage administered to a particular patient is variable, depending upon principally on the symptom or disease sought to be alleviated, the clinician's judgement, using as criteria: the route of administration, the duration of treatment, the size and condition of the patient, the potency of the active component and the patient's response thereto. The dosage administered depends, of course, also on whether or not the patient is suffering of congestive heart failure or acute heart failure or if the compound is given to interrupt or to prevent a certain type of arrhythmia. The higher dosages are of course preferred to interrupt or cause the cessation of the arrhythmias. An effective dosage amount of active component can thus be determined by the clinician, considering all traditional criteria and using of course, his best judgement on a patient's behalf. It will depend also what species is being treated humans or animal, and what species of animal is being treated.

It is important to note as is apparent from the above that the properties in the compounds of the invention are separable and not connected, i.e., there are compounds of the invention which possess one of the therapeutic or prophylactic properties disclosed and not the other properties, whereas in other compounds two or more properties will be present concurrently, though (as discussed and disclosed) not necessarily to the same degree or intensity. In short, the properties are not always associated and indeed should be considered disassociated from each other.

It is also within the spirit of the invention that the compounds of the invention be used together or not, in conjunction (as defined above) with each other or not.

As is evident from the disclosure, the invention describes and contemplates, of course, both the prophylactic and the therapeutic use of the compounds of the invention, illustratively, with respect to the antiarrhythmic properties.

The above illustrations are not intended to limit the invention thereto. Variations and changes of the parameters, the specific compounds of the invention used and other variables will become evident to those skilled in the art without departing from the spirit of the invention including its equivalents in all respects and terms including methods, compounds, compositions etc, which are all intended to be encompassed herein.

TABLE I (Protocol M)
LV dP/dt (mmHg/sec) (Control n = 6, Berberine n = 6)

| | | Baseline | 5 min | 15 min | 30 min | 45 min |
|---|---|---|---|---|---|---|
| $\overline{X}$ | Control | 1738.83 ± 65 | 1718.67 ± 77 | 1737.83 ± 93 | 1931.50 ± 69 | 1986.67 ± 91 |
| | Berberine | 1754.00 ± 227 | 2170.00 ± 247 | 2322.33 ± 276 | 2437.00 ± 276 | 2633.17 ± 207 |
| | t | .065 | 1.748 | 1.908 | 1.782 | 2.872 |
| | p | NS | NS | NS | NS | <.05 |
| $\overline{X}\Delta$ | Control | | −20.17 ± 32 | −1.00 ± 54 | 192.67 ± 57 | 247.83 ± 79 |
| | Berberine | | 416.00 ± 88 | 568.00 ± 81 | 638.00 ± 111 | 879.17 ± 102 |
| | t | | 4.650 | 5.876 | 3.954 | 4.908 |
| | p | | <.01 | <.005 | <.02 | <.005 |
| $\overline{X}\%$ | Control | | −1.22 ± 2 | −0.183 ± 3 | 11.42 ± 4 | 14.57 ± 5 |
| | Berberine | | 25.55 ± 7 | 32.67 ± 4 | 41.18 ± 8 | 58.62 ± 15 |
| | t | | 3.828 | 6.79 | 3.471 | 2.849 |
| | p | | <.02 | <.005 | <.02 | <.05 |
| paired | Control | | | | | |
| t | t | | −0.629 | −0.019 | 3.381 | 3.139 |
| | p | | NS | NS | <.02 | <.05 |
| | Berberine | | | | | |
| | t | | 4.719 | 7.050 | 6.202 | 8.657 |
| | p | | <.01 | <.001 | <.005 | <.001 |

TABLE II (Protocol M)
Aortic Flow (ml/min) (Control n = 6, Berberine n = 6)

| | | Baseline | 5 min | 15 min | 30 min | 45 min |
|---|---|---|---|---|---|---|
| $\overline{X}$ | Control | 1051.67 ± 268.81 | 1153.33 ± 345.99 | 1177.50 ± 406.30 | 1350.00 ± 631.48 | 1320.83 ± 639.98 |
| | Berberine | 887.50 ± 194.78 | 1109.17 ± 225.84 | 1160.83 ± 205.56 | 1123.33 ± 144.11 | 1196.67 ± 231.36 |

TABLE II-continued (Protocol M)
Aortic Flow (ml/min) (Control n = 6, Berberine n = 6)

|  |  | Baseline | 5 min | 15 min | 30 min | 45 min |
|---|---|---|---|---|---|---|
|  | t | 1.211 | 0.264 | 0.090 | 0.857 | 0.447 |
|  | p |  | NS | NS | NS | NS |
| $\overline{X}\Delta$ | Control |  | 101.67 ± 135.49 | 125.83 ± 204.71 | 298.33 ± 416.59 | 269.17 ± 440.27 |
|  | Berberine |  | 221.67 ± 83.47 | 273.33 ± 148.55 | 235.83 ± 150.68 | 309.17 ± 248.22 |
|  | t |  | 1.847 | 1.428 | 0.346 | 0.194 |
|  | p |  | NS | NS | NS | NS |
| $\overline{X}\Delta\%$ | Control |  | 9.42 ± 11.78 | 10.92 ± 19.09 | 24.45 ± 34.06 | 22.07 ± 37.87 |
|  | Berberine |  | 26.08 ± 11.82 | 33.98 ± 24.02 | 30.90 ± 28.92 | 39.10 ± 30.97 |
|  | t |  | 2.446 | 1.833 | 0.354 | 0.853 |
|  | p |  | NS | NS | NS | NS |
| paired t | Control |  |  |  |  |  |
|  | t |  | 1.838 | 1.506 | 1.754 | 1.498 |
|  | p |  | NS | NS | NS | NS |
|  | Berberine |  |  |  |  |  |
|  | t |  | 6.505 | 4.507 | 3.834 | 3.051 |
|  | p |  | <.005 | <.01 | <.02 | <.05 |

TABLE III (Protocol M)
dF/dt (ml/sec) (Control n = 6, Berberine n = 6)

|  |  | Baseline | 5 min | 15 min | 30 min | 45 min |
|---|---|---|---|---|---|---|
| $\overline{X}$ | Control | 410.02 ± 42 | 425.67 ± 38 | 425.05 ± 38 | 455.80 ± 57 | 494.40 ± 35 |
|  | Berberine | 331.85 ± 16 | 389.52 ± 32 | 409.14 ± 31 | 443.15 ± 34 | 463.88 ± 35 |
|  | t | 1.749 | 0.736 | 0.306 | 0.189 | 0.416 |
|  | p | NS | NS | NS | NS | NS |
| $\overline{X}\Delta$ | Control |  | 15.65 ± 27 | 15.03 ± 25 | 45.78 ± 36 | 84.38 ± 43 |
|  | Berberine |  | 57.67 ± 26 | 81.30 ± 22 | 111.50 ± 24 | 130.37 ± 37 |
|  | t |  | 1.130 | 1.886 | 1.515 | 0.813 |
|  | p |  | NS | NS | NS | NS |
| $\overline{X}\Delta\%$ | Control |  | 5.78 ± 6 | 5.67 ± 7 | 12.03 ± 10 | 21.48 ± 12 |
|  | Berberine |  | 17.45 ± 8 | 24.69 ± 7 | 33.31 ± 8 | 41.56 ± 13 |
|  | t |  | 1.175 | 1.851 | 1.698 | 1.135 |
|  | p |  | NS | NS | NS | NS |
| paired t | Control |  |  |  |  |  |
|  | t |  | 0.589 | 0.609 | 1.276 | 1.959 |
|  | p |  | NS | NS | NS | NS |
|  | Berberine |  |  |  |  |  |
|  | t |  | 2.216 | 3.368 | 4.573 | 3.507 |
|  | p |  | NS | <.02 | <.01 | <.02 |

TABLE IV (Protocol M)
Heart Rate (beats/min) (Control n = 6, Berberine n = 6)

|  |  | Baseline | 5 min | 15 min | 30 min | 45 min |
|---|---|---|---|---|---|---|
| $\overline{X}$ | Control | 121.00 ± 6 | 120.67 ± 6 | 119.00 ± 6 | 115.33 ± 5 | 114.33 ± 6 |
|  | Berberine | 110.00 ± 10 | 96.83 ± 11 | 96.33 ± 11 | 100.33 ± 9 | 99.33 ± 10 |
|  | t | .964 | 1.855 | 1.853 | 1.508 | 1.292 |
|  | p | NS | NS | NS | NS | NS |
| $\overline{X}\Delta$ | Control |  | −.33 ± 2 | −2.00 ± 2 | −5.500 ± 4 | −6.67 ± 4 |
|  | Berberine |  | −13.17 ± 3 | −13.67 ± 3 | −9.67 ± 4 | −10.67 ± 3 |
|  | t |  | 3.653 | 3.307 | .769 | .813 |
|  | p |  | <.02 | <.025 | NS | NS |
| $\overline{X}\Delta\%$ | Control |  | −.233 ± 2 | −1.517 ± 1 | −4.10 ± 3 | −5.22 ± 3 |
|  | Berberine |  | −13.12 ± 4 | −13.33 ± 4 | −8.20 ± 4 | −9.93 ± 3 |
|  | t |  | 3.045 | 3.094 | .835 | 1.044 |
|  | p |  | <.05 | <.05 | NS | NS |
| paired t | Control |  |  |  |  |  |
|  | t |  | −.200 | −1.225 | −1.477 | −1.800 |
|  | p |  | NS | NS | NS | NS |
|  | Berberine |  |  |  |  |  |
|  | t |  | −4.258 | −4.371 | −2.515 | −3.290 |
|  | p |  | <.01 | <.01 | NS | <.025 |

TABLE V (Protocol M)
Left Atrial Pressure (mmHg) (Control n = 6, Berberine n = 6)

|  |  | Baseline | 5 min | 15 min | 30 min | 45 min |
|---|---|---|---|---|---|---|
| $\overline{X}$ | Control | 1.83 ± 0.5 | 1.71 ± 0.5 | 1.67 ± 0.4 | 1.87 ± 0.5 | 1.92 ± 0.5 |
|  | Berberine | 2.25 ± 0.8 | 2.04 ± 0.4 | 1.54 ± 0.3 | 1.46 ± 0.3 | 1.29 ± 0.2 |

TABLE V-continued (Protocol M)
Left Atrial Pressure (mmHg) (Control n = 6, Berberine n = 6)

|  |  | Baseline | 5 min | 15 min | 30 min | 45 min |
|---|---|---|---|---|---|---|
|  | t | .467 | .530 | .263 | .735 | 1.096 |
|  | p | NS | NS | NS | NS | NS |
| $\overline{X}\Delta$ | Control |  | −.125 ± 0.1 | −.17 ± 0.2 | .042 ± 0.2 | .083 ± 0.2 |
|  | Berberine |  | −.208 ± 0.5 | −.71 ± 0.5 | −.792 ± 0.7 | −.96 ± 0.6 |
|  | t |  | .153 | .956 | 1.112 | 1.597 |
|  | p |  | NS | NS | NS | NS |
| $\overline{X}\Delta\%$ | Control |  | −4.17 ± 8 | 7.15 ± 19.3 | 15.08 ± 21.2 | 12.10 ± 18.5 |
|  | Berberine |  | 3.28 ± 19.9 | −22.2 ± 2.8 | −20.22 ± 18 | −31.27 ± 9.8 |
|  | t |  | .349 | 1.270 | 1.273 | 2.097 |
|  | p |  | NS | NS | NS | NS |

TABLE VI (Protocol M)
Left Ventricular End Diastolic Pressure (mmHg) (Control n = 6, Berberine n = 6)

|  |  | Baseline | 5 min | 15 min | 30 min | 45 min |
|---|---|---|---|---|---|---|
|  | Control | 3.42 ± 0.5 | 3.50 ± 0.5 | 3.50 ± 0.7 | 3.58 ± 0.8 | 3.67 ± 0.7 |
|  | Berberine | 3.83 ± 0.1 | 3.67 ± 0.3 | 3.50 ± 0.3 | 2.92 ± 0.3 | 3.33 ± 0.4 |
|  | t | .423 | .260 | 0.00 | .780 | .428 |
|  | p | NS | NS | NS | NS | NS |
| $\overline{X}\Delta$ | Control |  | .083 ± 0.2 | 0.83 ± 0.3 | .167 ± 0.4 | .25 ± 0.3 |
|  | Berberine |  | −.167 ± 0.7 | −.333 ± 0.8 | −.917 ± 1.02 | −.50 ± 0.9 |
|  | t |  | .353 | .510 | 1.002 | .792 |
|  | p |  | NS | NS | NS | NS |
| $\overline{X}\Delta\%$ | Control |  | 1.38 ± 5.5 | −.550 ± 9.6 | −1.12 ± 9.7 | 4.17 ± 6.7 |
|  | Berberine |  | 7.30 ± 11.2 | 4.17 ± 12.2 | −9.72 ± 13.4 | −.683 ± 13.1 |
|  | t |  | .475 | .305 | .521 | .332 |
|  | p |  | NS | NS | NS | NS |

TABLE VII (Protocol M)
Systolic Pressure (mmHg) (Control n = 6, Berberine n = 6)

|  |  | Baseline | 5 min | 15 min | 30 min | 45 min |
|---|---|---|---|---|---|---|
| $\overline{X}$ | Control | 108.2 ± 1.2 | 108.3 ± 1.6 | 108.5 ± 1.8 | 109.7 ± 2.25 | 109.8 ± 1.8 |
| (±SD) | Berberine | 108.3 ± 4.7 | 109.5 ± 4.5 | 107.8 ± 3.4 | 107.5 ± 3.8 | 110.0 ± 3.9 |
|  | t |  | 0.034 | 0.245 | 0.174 | 0.489 | 0.039 |
|  | p | NS | NS | NS | NS | NS |
| $\overline{X}\Delta$ | Control |  | 0.167 ± 0.7 | 0.33 ± 1.4 | 1.5 ± 1.4 | 1.67 ± 1.4 |
| (±SD) | Berberine |  | 1.17 ± 1.3 | 0.50 ± 1.6 | 0.83 ± 1.4 | 1.67 ± 1.8 |
|  | t |  | 0.697 | 0.402 | 1.16 | 0.0 |
|  | p |  | NS | NS | NS | NS |
| $\overline{X}\Delta\%$ | Control |  | 0.133 ± 0.6 | 0.283 ± 1.2 | 1.35 ± 1.3 | 1.55 ± 1.3 |
| (±SD) | Berberine |  | 1.17 ± 1.3 | −0.20 ± 1.3 | 0.933 ± 1.2 | 1.75 ± 1.7 |
|  | t |  | 0.739 | 0.275 | 0.235 | 0.095 |
|  | p |  | NS | NS | NS | NS |

TABLE VIII (Protocol M)
Diastolic Pressure (mmHg) (Control n = 6, Berberine n = 6)

|  |  | Baseline | 5 min | 15 min | 30 min | 45 min |
|---|---|---|---|---|---|---|
| $\overline{X}$ | Control | 84.50 ± 2.44 | 85.17 ± 2.1 | 84.17 ± 2.7 | 84.17 ± 2.4 | 83.83 ± 2.8 |
|  | Berberine | 84.33 ± 5.8 | 77.17 ± 4.5 | 74.67 ± 5.1 | 74.83 ± 2.7 | 71.17 ± 3.8 |
|  | t | 0.027 | 1.624 | 1.664 | 2.610 | 2.484 |
|  | p | NS | NS | NS | <.05 | NS |
| $\overline{X}\Delta$ | Control |  | 0.67 ± 0.9 | 0.33 ± 2.0 | −0.33 ± 1.7 | −1.67 ± 2.0 |
|  | Berberine |  | −7.17 ± 1.9 | −9.67 ± 4.2 | −9.50 ± 5 | −13.17 ± 3.2 |
|  | t |  | 3.704 | 2.001 | 1.734 | 3.066 |
|  | p |  | <.02 | NS | NS | <.05 |
| $\overline{X}\Delta\%$ | Control |  | 0.867 ± 1.04 | −0.300 ± 2.4 | −0.30 ± 2.0 | −1.90 ± 2.4 |
|  | Berberine |  | −8.150 ± 1.8 | −11.000 ± 4.5 | −9.93 ± 4.7 | −15.02 ± 3.0 |
|  | t |  | 4.285 | 2.107 | 1.912 | 3.417 |
|  | p |  | <.01 | NS | NS | <.02 |
| paired | Control |  |  |  |  |  |
| t | t |  | 0.756 | −0.164 | −0.2 | −0.82 |
|  | p |  | NS | NS | NS | .02 |
|  | Berberine |  |  |  |  |  |
|  | t |  | −3.729 | −2.301 | −1.893 | −4.158 |
|  | p |  | 0.025 | 0.10 | NS | 0.01 |

TABLE IX

Effect of Ouabain on Aortic Flow and Peripheral Resistance

|  | Diastolic arterial pressure (mmHg) | Aortic flow (ml/min) | Calculated total peripheral resistence (mmHg × min/ml) |
|---|---|---|---|
| Before | 73.18 ± 4.35 | 1194.55 ± 89.09 | 0.0670 ± 0.0094 |
| After | 75.18 ± 4.04 | 1017.73 ± 93.33 | .0836 ± 0.0123 |
| t | 0.88 | −3.4841 | 2.9126 |
| p | NS | <.01 | <.02 |

TABLE X

Multiple Infusion of Berberine in a Dog Prepared as in Protocol M

| Injection Time | Reading Time | df/dt | dp/dt | −dp/dt | flow | HR | LVP | S/D | AP |
|---|---|---|---|---|---|---|---|---|---|
| 11:10 | 11:09 | 2470 | 953 | 1524 | 1350 | 111 | 97 | 105/85 | 95 |
| 11:35 | 11:15 | 3458 | 1143 | 1524 | 1350 | 91 | 100 | 100/80 | 92 |
| 11:46 | 11:30 | 3458 | 1492 | 1524 | 1300 | 91 | 100 | 105/85 | 92 |
| 12:01 | 11:45 | 3952 | 1715 | 1524 | 1400 | 77 | 102 | 105/82 | 90 |
| 12:16 | 12:00 | 4693 | 1810 | 1334 | 1550 | 71 | 100 | 100/75 | 90 |
| 12:31 | 12:15 | 5681 | 2000 | 1334 | 1700 | 67 | 97 | 100/70 | 90 |
| 12:46 | 12:30 | 5187 | 2096 | 1334 | 1650 | 68 | 95 | 100/70 | 90 |
| 1:11 | 12:45 | 6422 | 2286 | 1143 | 2050 | 68 | 95 | 95/65 | 82 |
|  | 1:10 | 8645 | 2858 | 1143 | 2400 | 81 | 100 | 100/60 | 75 |
|  | 1:30 | 11609 | 3524 | 1143 | 3100 | 81 | 105 | 105/50 | 75 |

TABLE XI

(Protocol RK) Systolic Pressure (mmHg)

| Dog # | Baseline | 5' | 10' | 15' | 30' | 45' | 50' | 60' | 75' | 90' | 105' |
|---|---|---|---|---|---|---|---|---|---|---|---|
| 1178 | 132 | 100 | 115 | 120 | 105 | 105 | 100 | 90 | 105 | 110 | 132 |
| 1190 | 135 | 105 | 100 | 100 | 117 | 115 | 105 | 110 | 115 | 120 | 120 |
| 1200 | 145 | 105 | 100 | 105 | 142 | 137 | 120 | 130 | 125 | 125 | 125 |
| 1216 | 105 | 85 | 107 | 95 | 110 | 110 | 107 | 105 | 115 | 120 | 107 |
| 1232 | 127 | 115 | 117 | 120 | 115 | 120 | 110 | 110 | 105 | 110 | 105 |
| 1235 | 130 | 112 | 105 | 105 | 110 | 105 | 110 | 100 | 100 | 100 | 105 |
| $\bar{X}$ | 129 | 103 | 109 | 107.5 | 117 | 115 | 109 | 108 | 111 | 114 | 116 |
| S.E. | 5.42 | 14.9 | 2.60 | 4.57 | 5.38 | 4.94 | 2.73 | 544 | 3.74 | 3.74 | 4.74 |
| t |  | −5.9638 | −3.1076 | −3.7820 | −2.5998 | −2.6953 | −4.0363 | −3.6702 | −3.0961 | −2.3426 | −2.8186 |
| p |  | <.005 | <.025 | <.025 | <.05 | <.05 | <.010 | <.025 | <.05 | <.01 | <.05 |

TABLE XII

(Protocol RK) Diastolic Pressure (mmHg)

| Dog # | Baseline | 5' | 10' | 15' | 30' | 45' | 50' | 60' | 75' | 90' | 105' |
|---|---|---|---|---|---|---|---|---|---|---|---|
| 1178 | 102 | 75 | 90 | 90 | 80 | 80 | 75 | 65 | 80 | 85 | 85 |
| 1190 | 110 | 75 | 87 | 75 | 85 | 82 | 80 | 82 | 80 | 85 | 85 |
| 1200 | 120 | 90 | 70 | 80 | 120 | 101 | 100 | 100 | 100 | 97 | 92 |
| 1216 | 70 | 55 | 75 | 55 | 75 | 75 | 75 | 75 | 80 | 85 | 73 |
| 1232 | 107 | 90 | 95 | 95 | 92 | 100 | 85 | 87 | 85 | 85 | 80 |
| 1235 | 95 | 75 | 75 | 75 | 75 | 70 | 65 | 60 | 55 | 55 | 62 |
| $\bar{X}$ | 101 | 77 | 82 | 80 | 88 | 86 | 80 | 78 | 80 | 82 | 81 |
| S.E. | 7.01 | 5.27 | 4.08 | 4.47 | 6.95 | 5.96 | 4.83 | 6.01 | 5.91 | 5.74 | 5.03 |
| t |  | −7.4421 | −2.5160 | −3.6246 | −2.5317 | −2.9305 | −3.8260 | −3.6098 | −3.0195 | −2.5084 | −3.3716 |
| p |  | <.001 | <.1 | <.025 | <.1 | <.05 | <.025 | <.025 | <.05 | <.1 | <.025 |

TABLE XIII

Comparison between Berberine (n = 7), Tetrahydropalmatine (THP, n = 4), Berberubine (n = 7), and Coreximine (n = 8). (Numbers are expressed as percent increase and p value are relative to pre-treatment condition. Since there are only 4 dogs with THP no statistical analysis was performed).

|  | Berberine | THP | Berberubine | Coreximine |
|---|---|---|---|---|
| dP/dt | 44 | 32 | 36 | 32 |
|  | (p < 0.01) |  | (p < 0.001) | (p < 0.05) |
| PP | 69 | 28 | 24 | 31 |
|  | (p < 0.02) |  | (p < 0.02) | (p < 0.02) |
| HR | −16 | −5 | −17 | −17 |
|  | (p < 0.05) |  | (p < 0.01) | (p < 0.05) |

TABLE XIII-continued

Comparison between Berberine (n = 7), Tetrahydropalmatine (THP, n = 4), Berberubine (n = 7), and Coreximine (n = 8). (Numbers are expressed as percent increase and p value are relative to pre-treatment condition. Since there are only 4 dogs with THP no statistical analysis was performed).

|  | Berberine | THP | Berberubine | Coreximine |
|---|---|---|---|---|
| SV | 54 | 62 | 11 (NS) | 38 |
|  | (p < 0.01) |  |  | (p < 0.02) |
| TPR | −36 | −32 | 12 (NS) | 4 (NS) |

(p < 0.05)

TABLE XIV

Effect of Berberine on Ejection Fraction

|  |  | Ejection fraction (quadruplicate reading) |  |  |  | Mean | Average |
|---|---|---|---|---|---|---|---|
| Dextrose | Before | .35 | .30 | .32 | .29 | .315 | 0.33 ± 0.02 |
| % water | 5 min | .37 | .40 | .40 | .39 | .39 |  |
| 5 min | 15 min | .35 | .31 | .35 | .31 | .34 |  |
| infusion | 30 min | .34 | .34 | .36 | .31 | .34 |  |
|  | 45 min | .28 | .26 | .29 | .31 | .28 |  |
| Berberine | 5 min | .42 | .43 | .49 | .48 | .46 | 0.44 ± 2 |
| 0.7 mg/kg/min | 15 min | .48 | .45 | .48 | .48 | .47 | (p < 0.01) |

TABLE XIV-continued

Effect of Berberine on Ejection Fraction

| | | Ejection fraction (quadruplicate reading) | | | | Mean | Average |
|---|---|---|---|---|---|---|---|
| 5 min infusion | 30 min | .43 | .47 | .45 | .42 | .44 | |
| | 45 min | .35 | .39 | .37 | .39 | .38 | |
| Berberine 0.7 mg/kg/min | 5 min | .45 | .46 | .50 | .43 | .46 | 0.40 ± 2 |
| | 15 min | .37 | .39 | .37 | .35 | .37 | ($p < 0.05$) |
| | 30 min | .41 | .41 | .38 | .38 | .40 | |
| | 45 min | .36 | .39 | .42 | .35 | .38 | |

TABLE XV

Effect of Berberine (0.2 mg/kg/min) on Ejection Fraction (as done by MUGR) in Conscious Dogs with Acute Left Ventricular Failure (LVF).

| Dog # | Before LVF | LVF | During Berberine Infusion | 30 min after Berberine Infusion |
|---|---|---|---|---|
| 1 | 45 | 24 | 38 | 33 |
| 2 | 56 | 34 | 51 | 41 |
| 3 | 53 | 35 | 49 | 44 |
| 4 | 58 | 20 | 31 | 30 |
| 5 | 55 | 21 | 35 | 30 |
| 6 | 45 | 28 | 39 | 33 |
| Average ± SE | 55 ± 2 | 27 ± 2 | 40 ± 3 | 35 ± 2 |
| | $p < 0.001$ | $p < 0.001$ | | |
| | | | $p < 0.001$ | |

TABLE XVI

Effects of Berberine and Ouabain on Hemodynamics in Dogs with Acute Heart Failure

| | Control | | Oubain | | Berberine | |
|---|---|---|---|---|---|---|
| | Before | ΔChange | Before | ΔChange | Before | ΔChange |
| Heart rate (beats/min) | 136 ± 4 | 0 ± 3 | 124 ± 5 | −3 ± 1* | 126 ± 12 | −8 ± 2* |
| Systolic AP (mmHg) | 124 ± 9 | −1 ± 4 | 115 ± 6 | 1 ± 3 | 118 ± 7 | −4 ± 3 |
| Diastolic AP (mmHg) | 97 ± 9 | −1 ± 4 | 84 ± 7 | 3 ± 2 | 90 ± 7 | −9 ± 3* |
| Mean AP (mmHg) | 111 ± 9 | −3 ± 4 | 98 ± 7 | 0 ± 2 | 102 ± 7 | −6 ± 2* |
| Pulse pressure (mmHg) | 26 ± 1 | 0 ± 1 | 31 ± 3 | −1 ± 2 | 28 ± 2 | 5 ± 3 |
| LV dP/dt (mmHg/sec) | 1628 ± 132 | −72 ± 64 | 1700 ± 80 | 178 ± 61* | 1572 ± 80 | 440 ± 91 \|\| ** |
| LV EDP (mmHg) | 14.1 ± 0.5 | 0.4 ± 0.5 | 13.0 ± 1.8 | −2.0 ± 1.1 | 13.3 ± 0.8 | −5.0 ± 0.8 \|\| ** |
| Cardiac output (liter/min) | 1.77 ± 0.28 | −0.22 ± 0.08* | 1.84 ± 0.16 | −0.07 ± 0.18 | 1.76 ± 0.15 | 0.17 ± 0.06 ** |
| Stroke volume (ml/beat) | 12.9 ± 1.8 | −1.4 ± 0.5 | 14.8 ± 1.1 | −0.2 ± 1.4 | 14.6 ± 1.9 | 2.7 ± 1.1 * |
| TPR (dyn.sec.cm$^{-5}$) | 5943 ± 1124 | 601 ± 466 | 4495 ± 551 | 10 ± 491 | 4915 ± 559 | −852 ± 156 ** |

AP = Aortic pressure; LV dP/dt = Maximal rate of rise of left ventricular pressure; LV EDP = left ventricular end diastolic pressure; TPR = Total peripheral vascular resistance; * = $p < 0.05$ and ** = $p < 0.005$ for paired t-test between values before and after intervention; = $p < 0.05$ and = $p < 0.01$ for unpaired t-test between control group and treated groups; \|\| = $p < 0.05$ for unpaired t-test between berberine HCl and oubain treated groups.

TABLE XVII

Effect of Berberine, Oubain and the Combination of Both Peak LV dP/dt (numbers are percent increase compared to before treatment).

| Drug Intervention | Time after Treatment | | | | | |
|---|---|---|---|---|---|---|
| | 5 min | 10 min | 15 min | 20 min | 25 min | 30 min |
| Berberine alone | 30.2 ± 4.1 | 36.2 ± 3.5 | 39.2 ± 3.3 | 42.6 ± 4.9 | 38.8 ± 5.4 | 40.5 ± 6.7 |
| Ouabain alone | 17.1 ± 2.1 | 24.0 ± 2.8 | 33.8 ± 3.8 | 36.1 ± 4.3 | 44.0 ± 6.3 | 49.0 ± 7.3 |
| Ouabain and Berberine | xxx | xxx | xxx | xxxx | xxxx | xxxx |
| | 87.1 ± 10.0 | 82.0 ± 12.8 | 87.5 ± 13.3 | 95.4 ± 16.0 | 98.2 ± 16.5 | 97.6 ± 14.7 |
| | ooo | ooo | ooo | oooo | oooo | oooo |
| Ouabain and Berberine vs. Berberine alone | = $p < 0.005$ | ooo | | | | |
| | | $p < 0.000$ | oooo | | | |
| Ouabain and Berberine vs. Ouabain alone | = $p < 0.005$ | xxx | | | | |
| | | P $< 0.001$ | xxxx | | | |

I claim:

1. A therapeutic method for increasing contractility of the mammalian heart as shown by a positive inotropic effect which comprises administering to a mammal in need thereof in an amount effective to cause a positive inotropic effect, a composition which comprises a biologically acceptable carrier and a compound selected from the group consisting of berberrubine and the pharmaceutically acceptable salts thereof, causing a positive inotropic effect and discontinuing administration.

2. The therapeutic method of claim 1 wherein the compound is administered periodically.

3. A therapeutic method for increasing contractility of the mammalian heart as shown by a positive inotropic effect which comprises administering to a mammal in need thereof in an amount effective to cause a positive inotropic effect, a composition which comprises a biologically acceptable carrier and a compound selected from the group consisting of tetrahydropalmatine and its pharmaceutically acceptable salts thereof, causing a positive inotropic effect and discontinuing administration.

4. The therapeutic method of claim 3 wherein the compound is administered periodically.

5. A therapeutic method for increasing contractility of the mammalian heart as shown by a positive inotropic effect which comprises administering to a mammal in need thereof a composition which comprises a pharmaceutically acceptable carrier and a cardiac glycoside and in conjunction therewith, in an amount effective to cause a positive inotropic effect, a composition which comprises a pharmaceutically acceptable carrier and a compound selected from the group consisting of berberrubine, tetrahydropalmatine and the pharmaceutically acceptable salts thereof, causing a positive inotropic effect.

6. The therapeutic method of claim 5 wherein the compound is administered periodically.

7. The therapeutic method of claim 5 wherein the compound is berberrubine or its pharmaceutically acceptable salts.

8. The therapeutic method of claim 5 wherein the compound is tetrahydropalmatine or its pharmaceutically acceptable salts.

9. The therapeutic method of claim 5, 6, 7 or 8 wherein the cardiac glycoside is selected from the group consisting of ouabain, digoxin, digitoxin and delanoside.

10. A therapeutic method for increasing contractility of the mammalian heart as shown by a positive inotropic effect which comprises administering to a mammal in need thereof a composition which comprises a pharmaceutically acceptable carrier and a cardiac glycoside and in conjunction therewith, in an amount effective to cause a positive inotropic effect, a composition which comprises a pharmaceutically acceptable carrier and a compound selected from the group consisting of berberine and the pharmaceutically acceptable salts thereof, causing a positive inotropic effect and discontinuing the administration of the composition comprising the cardiac glycoside and the compositiion comprising the compound.

11. The therapeutic method of claim 10 wherein the compound is administered periodically.

12. The therapeutic method of claim 10 or 11 wherein the cardiac glycoside is selected from the group consisting of ouabain, digoxin, digitoxin and delanoside.

13. The method of claims 1, 2, 3 or 4 wherein the compound is administered in a dosage in the range of about 0.001 to about 50 mg/kg.

14. The method of claims 1, 2, 3 or 4 wherein the compound is administered in a dosage in the range of about 0.02 to 0.7 mg/kg.

15. The method of claim 5 wherein the compound is administered in a dosage in the range of about 0.001 to about 50 mg/kg.

16. The method of claim 5 wherein the compound is administered in a dosage in the range of about 0.02 to about 0.7 mg/kg.

17. The method of claim 10 wherein the compound is administered in a dosage in the range of about 0.001 to about 50 mg/kg.

18. The method of claim 10 wherein the compound is administered in a dosage in the range of about 0.02 to 0.7 mg/kg.